(12) United States Patent  (10) Patent No.: US 9,066,774 B2
Simons  (45) Date of Patent: *Jun. 30, 2015

(54) HOLDER FOR OBTURATION MATERIAL DELIVERY DEVICE

(71) Applicant: Wyatt Simons, San Clemente, CA (US)

(72) Inventor: Wyatt Simons, San Clemente, CA (US)

(73) Assignee: Endodontic Specialist's Advocate, LLC, Newport Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/715,045

(22) Filed: Dec. 14, 2012

(65) Prior Publication Data

US 2013/0122455 A1    May 16, 2013

Related U.S. Application Data

(63) Continuation of application No. PCT/US2012/033237, filed on Apr. 12, 2012.

(60) Provisional application No. 61/620,229, filed on Apr. 4, 2012, provisional application No. 61/476,100, filed on Apr. 15, 2011.

(51) Int. Cl.
    *A61C 3/00* (2006.01)
    *A61C 5/04* (2006.01)

(52) U.S. Cl.
    CPC .. *A61C 5/045* (2013.01); *A61C 5/04* (2013.01)

(58) Field of Classification Search
    CPC .................................. A61C 5/04; A61C 5/045
    USPC .......................... 433/27, 32, 81–83, 102, 224
    See application file for complete search history.

(56) References Cited

U.S. PATENT DOCUMENTS

| 3,772,791 A | 11/1973 | Malmin |
| 3,855,705 A | 12/1974 | Malmin |
| 3,899,830 A | 8/1975 | Malmin |
| 4,392,827 A | 7/1983 | Martin |
| 4,480,996 A | 11/1984 | Crovatto |
| 4,525,147 A | 6/1985 | Pitz et al. |
| 4,681,545 A | 7/1987 | Lapcevic |
| 4,962,765 A | 10/1990 | Kung et al. |
| 4,992,045 A | 2/1991 | Beisel |
| 5,051,093 A | 9/1991 | Fitzmorris |

(Continued)

FOREIGN PATENT DOCUMENTS

WO     2006104315 A1    10/2006

OTHER PUBLICATIONS

International Search Report from corresponding International Application No. PCT/US2012/033237 mailed Oct. 16, 2012.

(Continued)

*Primary Examiner* — Edward Moran
(74) *Attorney, Agent, or Firm* — Polster, Lieder, Woodruff & Lucchesi, L.C.

(57) ABSTRACT

A holder for a delivery device for delivering filler material into a prepared root canal comprises a body, a mounting portion adapted to removably receive the delivery device; and a heating circuit having a heating device wherein said heating device is positioned to be in thermal communication with said delivery device when the delivery device is mounted to the holder. The holder thus enables heating of the filling material in situ in the prepared root canal at the time of insertion of the filling material in to the canal and while the filler material is being packed into the prepared canal.

36 Claims, 19 Drawing Sheets

(56) References Cited

U.S. PATENT DOCUMENTS

| | | |
|---|---|---|
| 5,236,362 A | 8/1993 | Cohen et al. |
| 5,263,861 A | 11/1993 | Cohen et al. |
| 5,588,835 A | 12/1996 | Kert |
| 5,833,457 A | 11/1998 | Johnson |
| 5,893,713 A | 4/1999 | Garman et al. |
| 6,193,510 B1 * | 2/2001 | Tsimerman .................... 433/29 |
| 6,254,392 B1 | 7/2001 | Mannschedel et al. |
| 6,270,343 B1 | 8/2001 | Martin |
| 6,312,261 B1 | 11/2001 | Mays |
| 6,416,320 B1 | 7/2002 | Roffe et al. |
| 6,428,319 B1 | 8/2002 | Lopez et al. |
| 6,508,647 B2 | 1/2003 | Kusano |
| 6,513,254 B1 | 2/2003 | Lunn |
| 6,537,068 B2 | 3/2003 | Kusano |
| 6,644,972 B1 | 11/2003 | Mays |
| 7,090,499 B1 | 8/2006 | Mays et al. |
| 7,163,401 B2 | 1/2007 | Karmaker et al. |
| 7,168,952 B2 | 1/2007 | Karmaker et al. |
| 7,665,991 B1 | 2/2010 | Kert |
| 2002/0081548 A1 | 6/2002 | Lopez |
| 2003/0148247 A1 | 8/2003 | Sicurelli, Jr. et al. |
| 2003/0219699 A1 | 11/2003 | Martin |
| 2004/0009452 A1 | 1/2004 | Oh |
| 2004/0224282 A1 | 11/2004 | Kazen et al. |
| 2006/0154199 A1 | 7/2006 | Maxwell et al. |
| 2008/0038697 A1 | 2/2008 | Pavlov |
| 2008/0261167 A1 | 10/2008 | Maitre et al. |
| 2010/0063377 A1 | 3/2010 | Becker et al. |
| 2010/0124728 A1 | 5/2010 | Walia |
| 2010/0209867 A1 * | 8/2010 | Becker et al. .................... 433/32 |
| 2010/0297571 A1 | 11/2010 | Lee |

OTHER PUBLICATIONS

International Written Opinion from corresponding International Application No. PCT/US2012/033237 mailed Oct. 16, 2012.

* cited by examiner

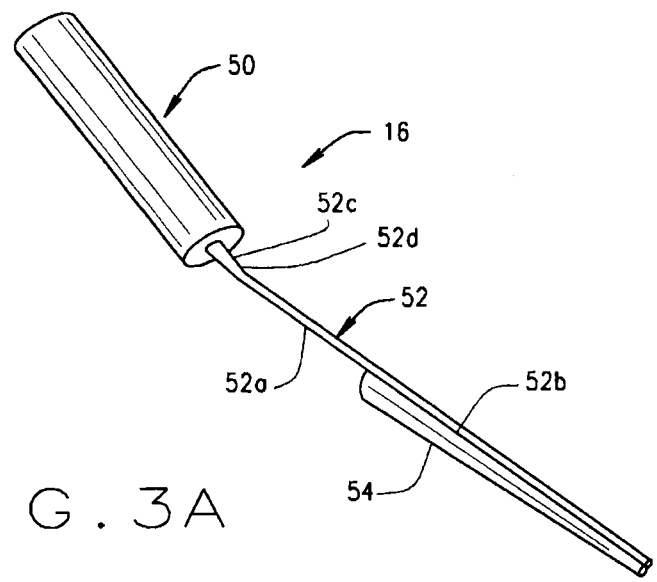
FIG. 3A
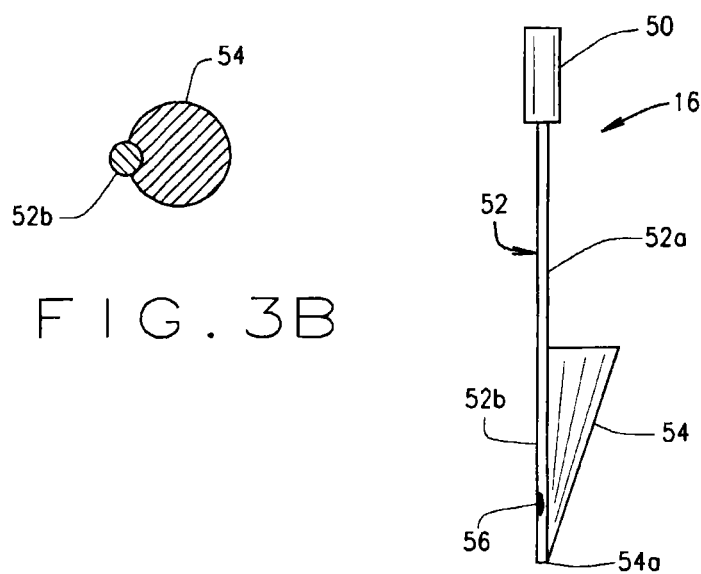
FIG. 3B
FIG. 3C

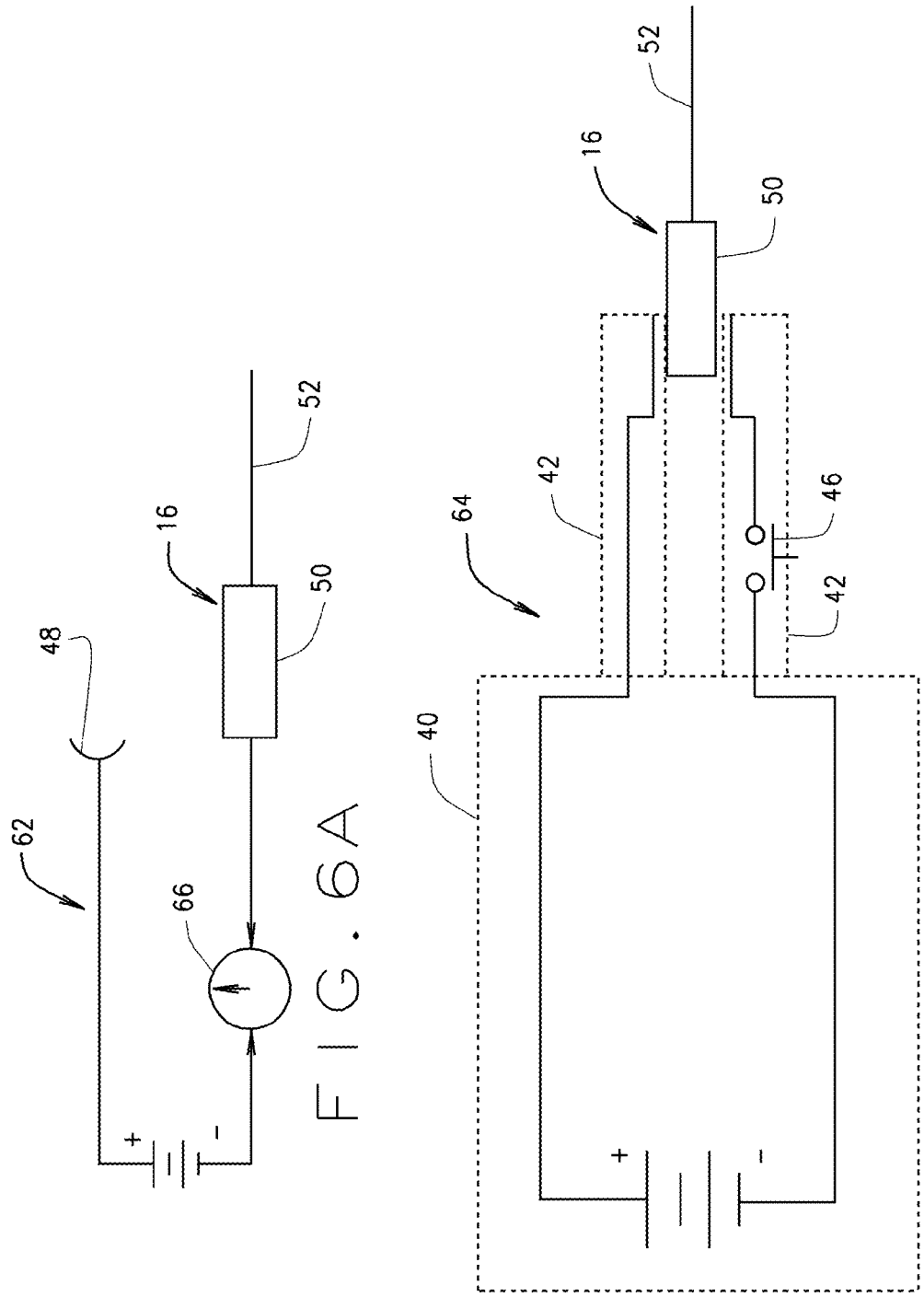

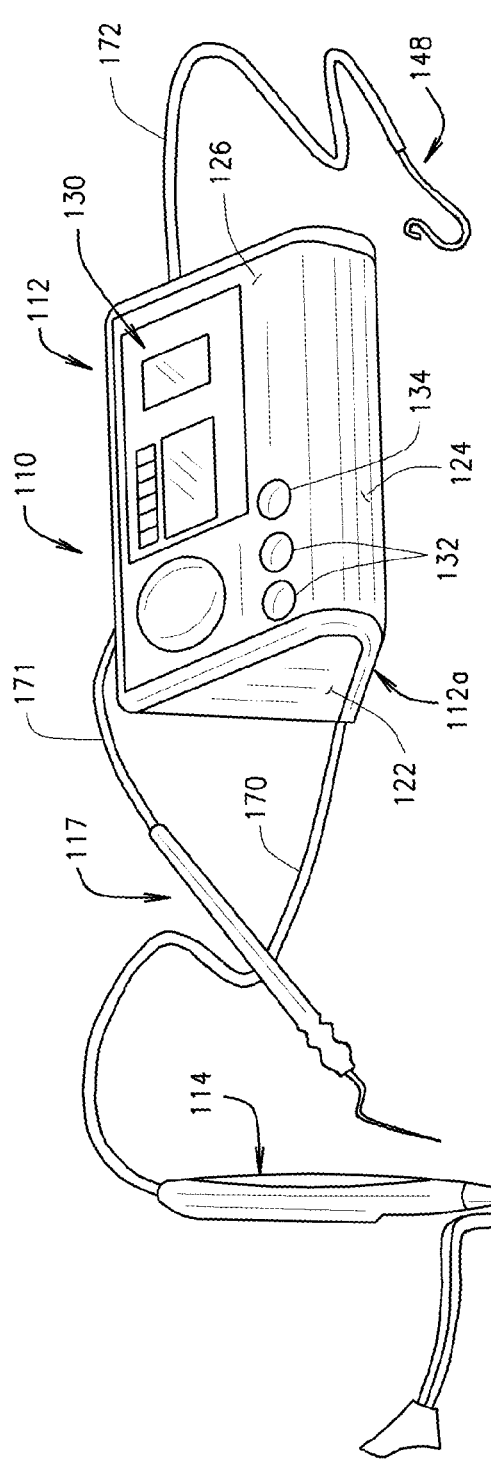
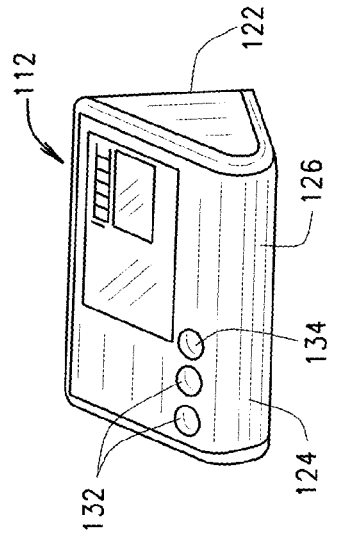
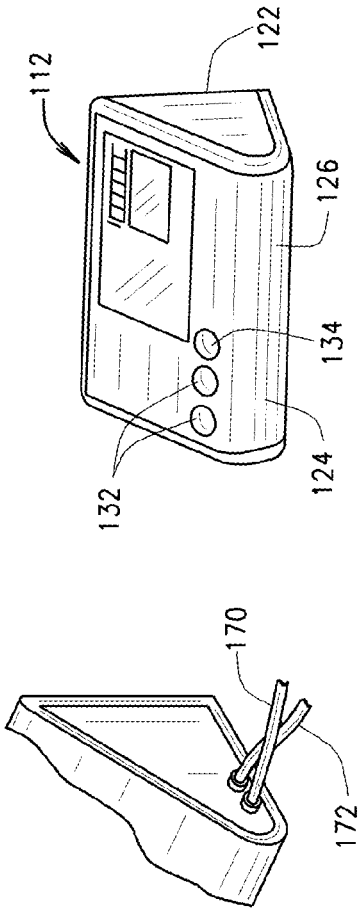

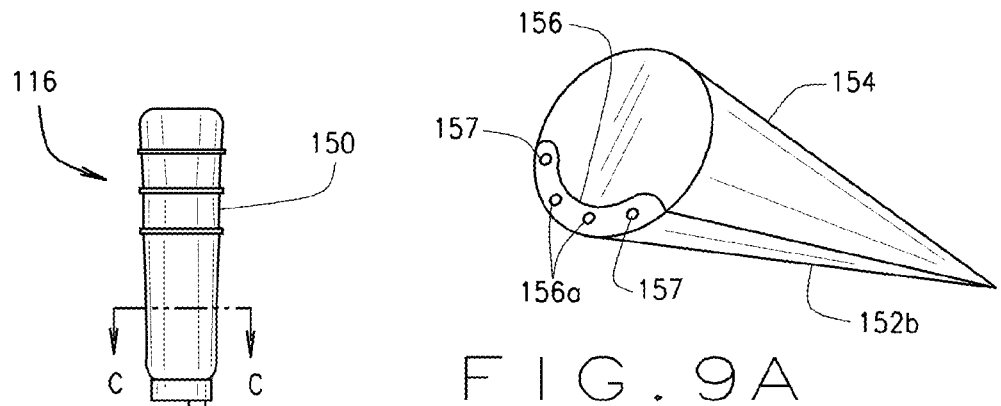
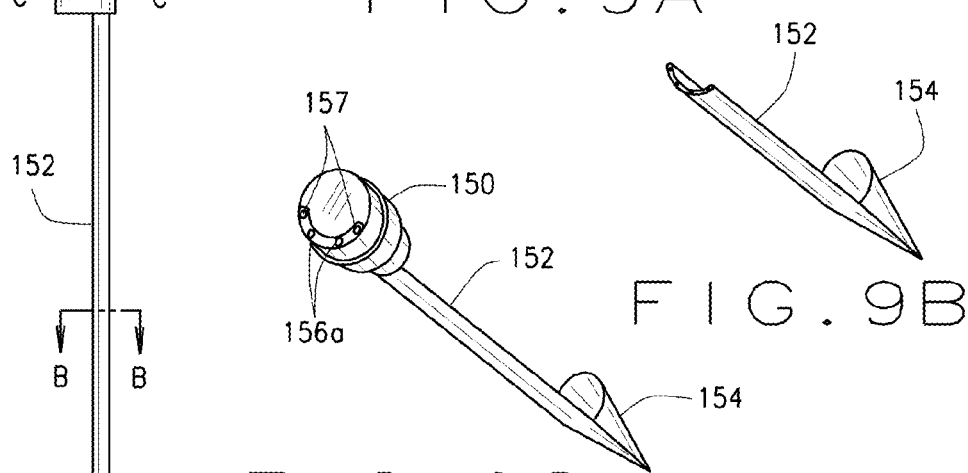
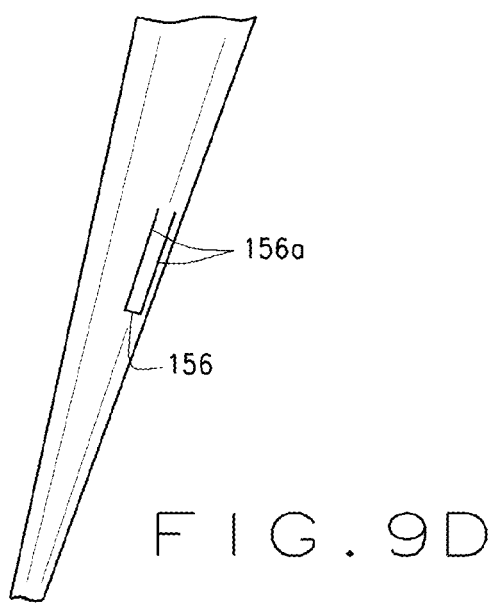

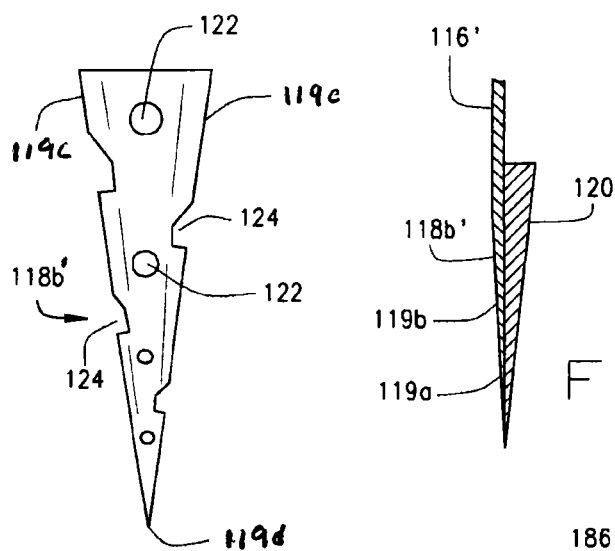
FIG. 12
FIG. 13
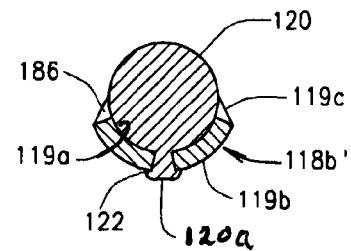
FIG. 14A
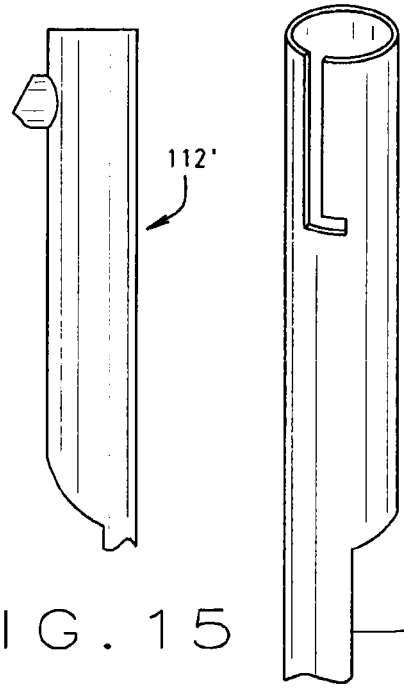
FIG. 15
FIG. 16
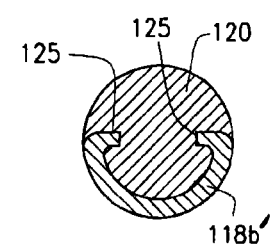
FIG. 14B

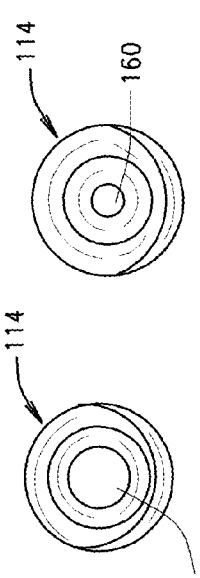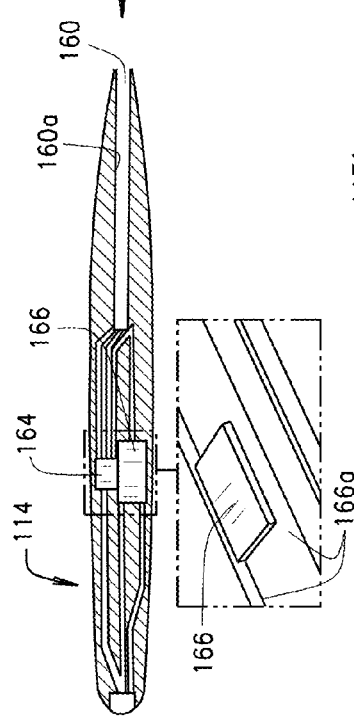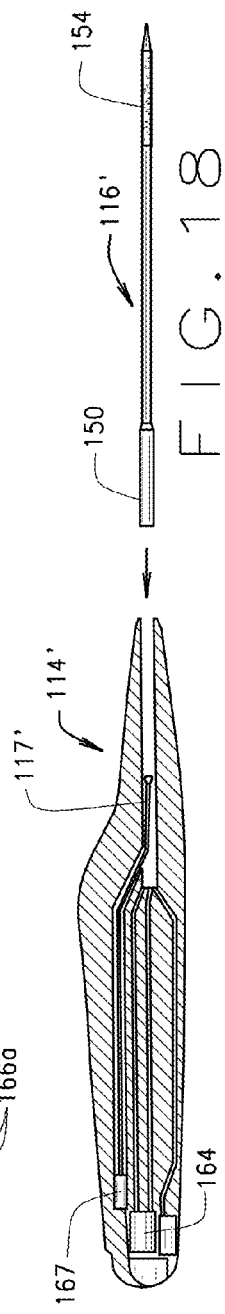

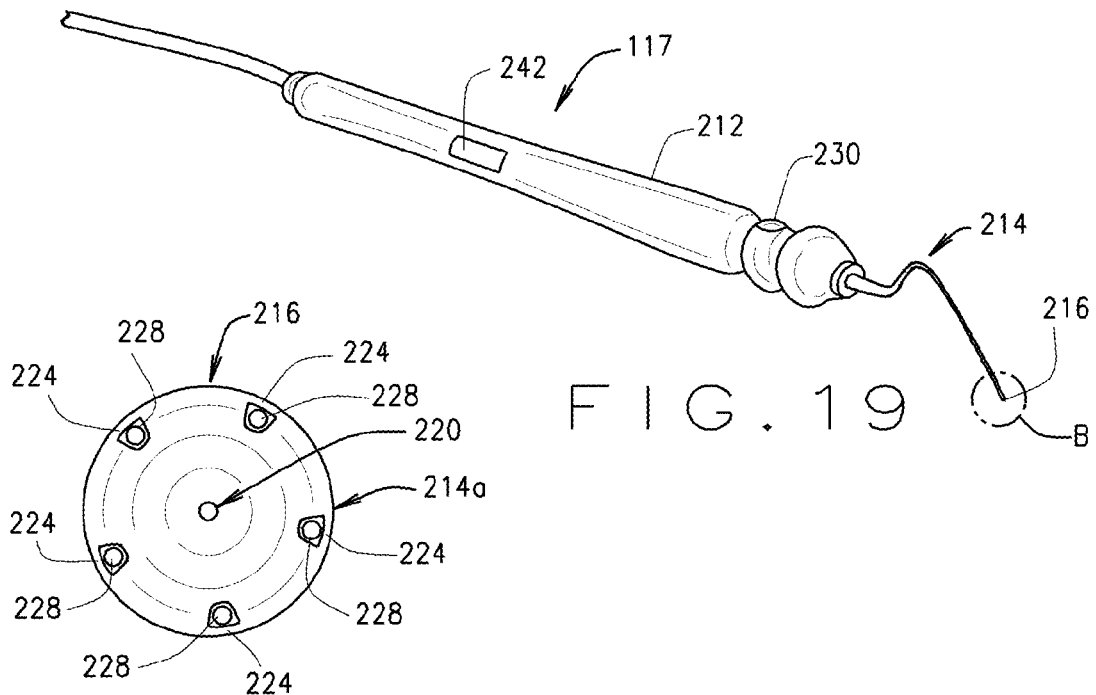
FIG. 19
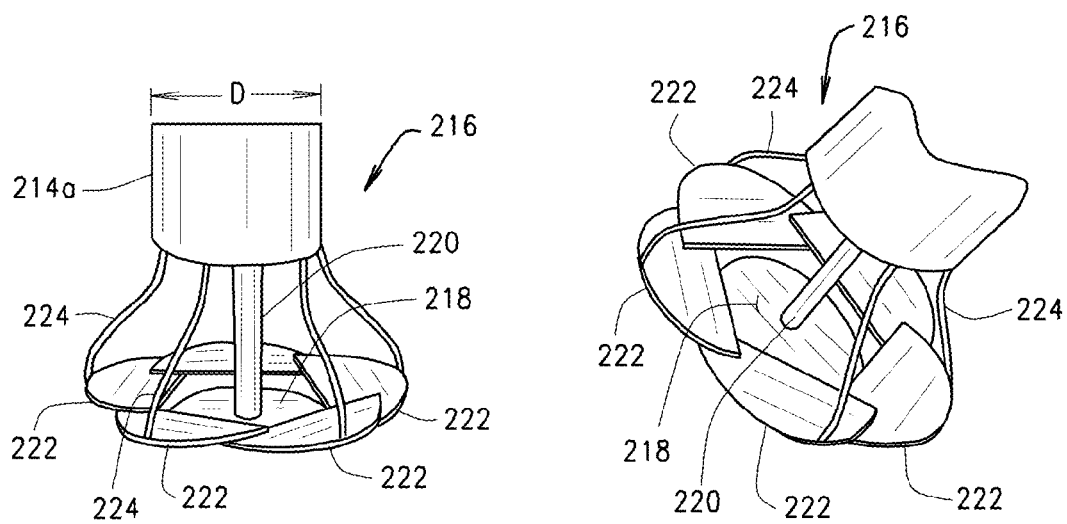
FIG. 20
FIG. 21
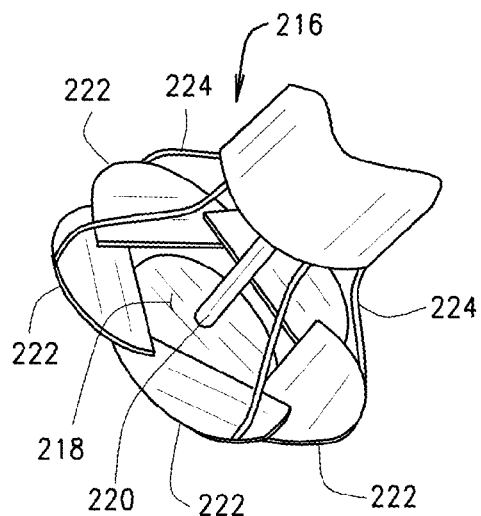
FIG. 22

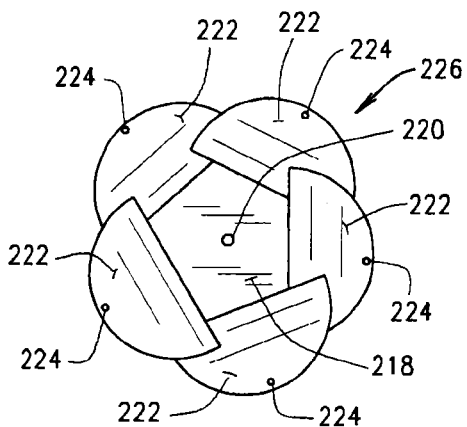
FIG. 23
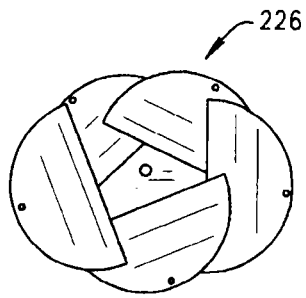
FIG. 24
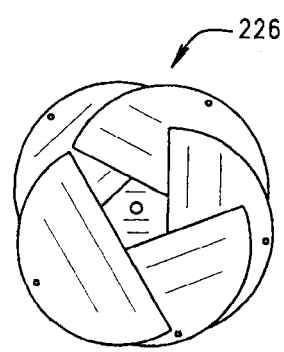
FIG. 25
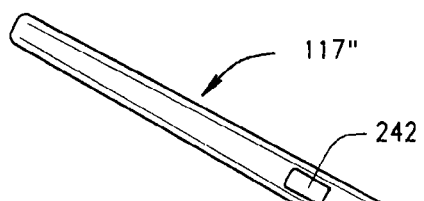
FIG. 27
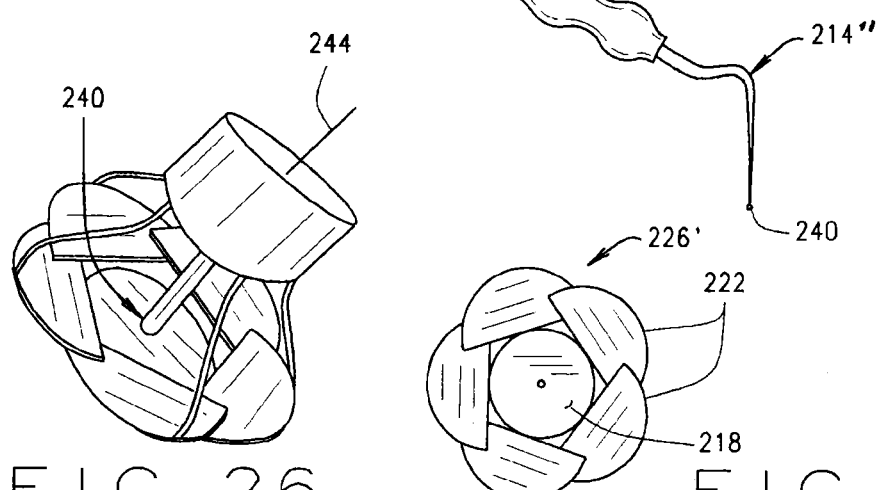
FIG. 26
FIG. 28

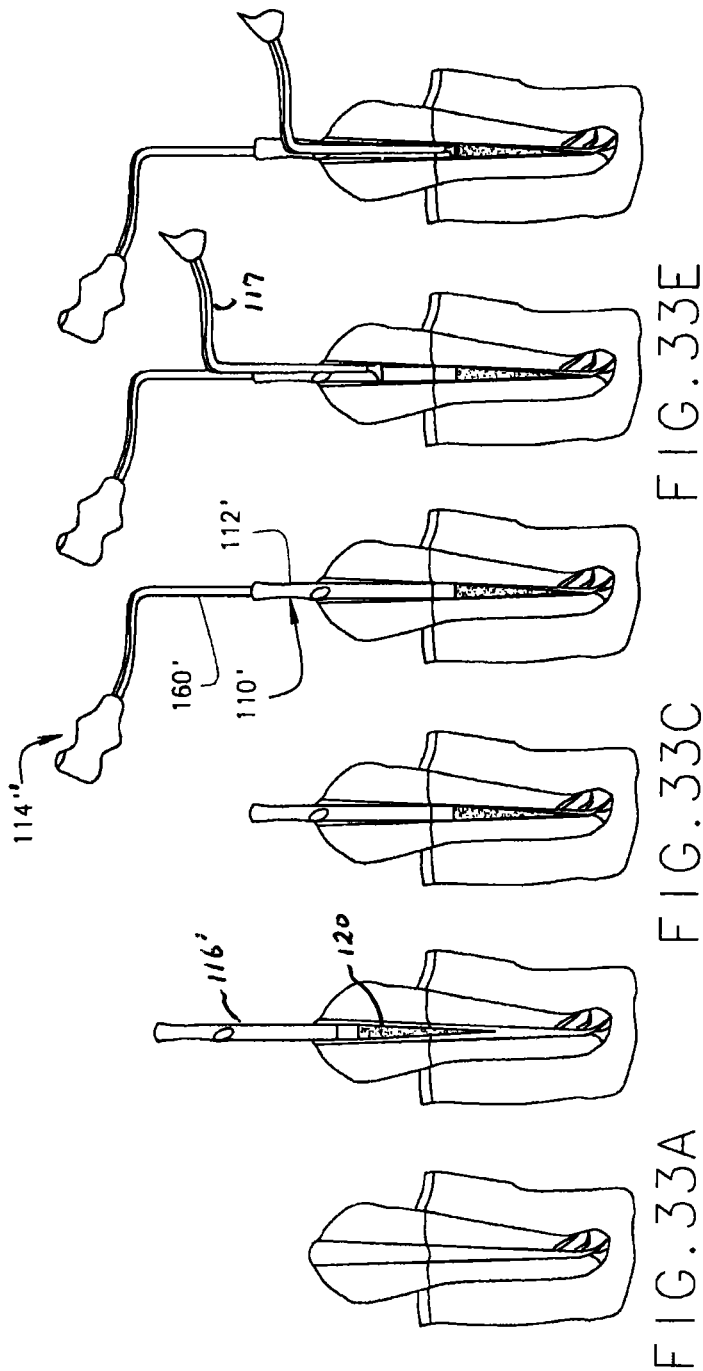

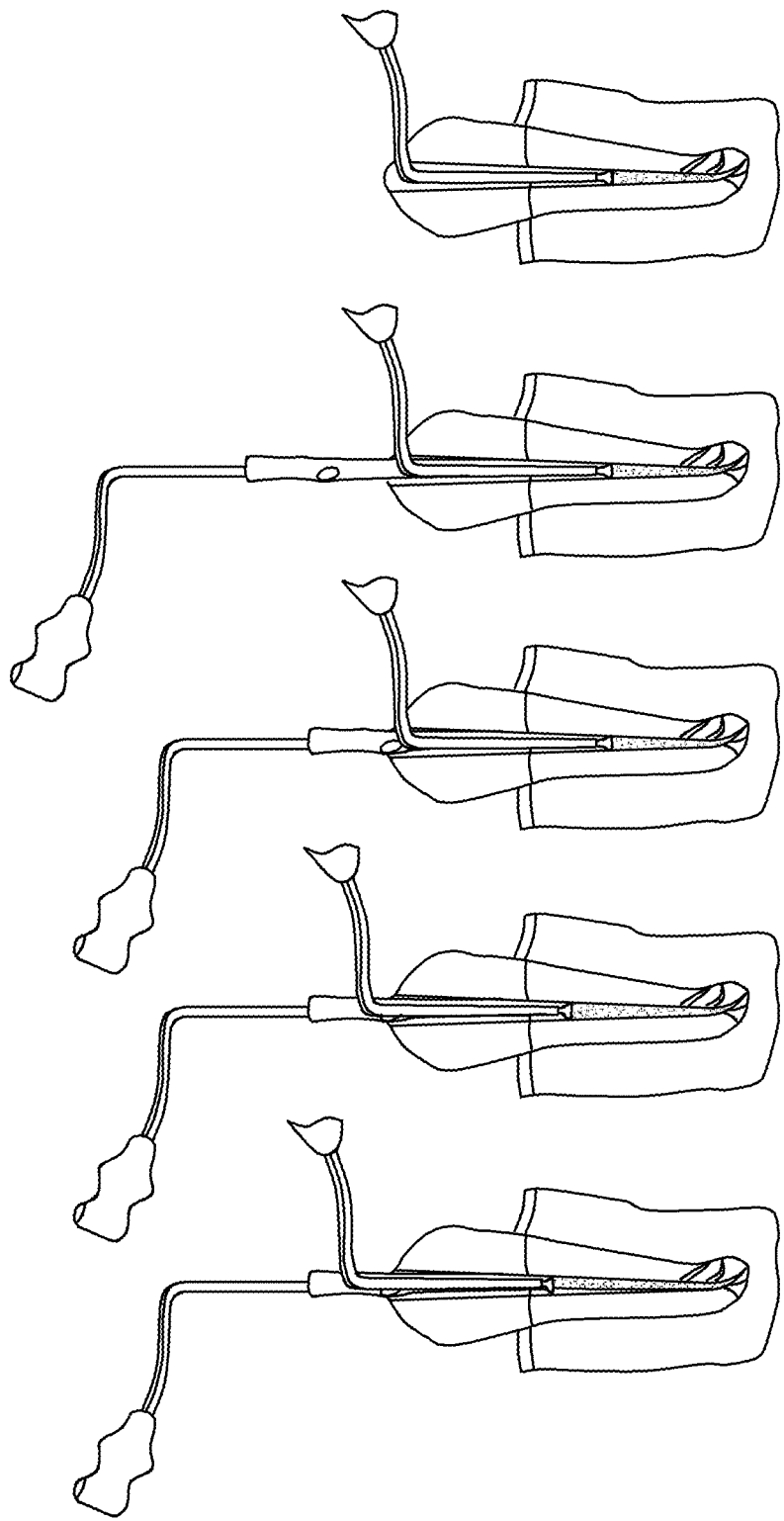

ical filing date of Apr. 12, 2012, and which claims priority to U.S. App. No. 61/476,100 filed Apr. 15, 2011 and U.S. App. No. 61/620,229 filed Apr. 4, 2012, all of which are entitled "Endodontic Obturation System" and all of which are incorporated herein by reference. In addition, this application is related to the following co-owned applications which are filed concurrently herewith: application Ser. No. 13/714,966, entitled Obturation Material Delivery Device, application Ser. No. 13/714,988, entitled Endodontic Plugger, and application Ser. No. 13/715,068, entitled "Endodontic Obturation System And Method", all of which are incorporated herein by reference.

HOLDER FOR OBTURATION MATERIAL DELIVERY DEVICE

CROSS-REFERENCE TO RELATED APPLICATIONS

This application is a continuation of International App. No. PCT/US2012/033237, having an international filing date of Apr. 12, 2012, and which claims priority to U.S. App. No. 61/476,100 filed Apr. 15, 2011 and U.S. App. No. 61/620,229 filed Apr. 4, 2012, all of which are entitled "Endodontic Obturation System" and all of which are incorporated herein by reference. In addition, this application is related to the following co-owned applications which are filed concurrently herewith: application Ser. No. 13/714,966, entitled Obturation Material Delivery Device, application Ser. No. 13/714,988, entitled Endodontic Plugger, and application Ser. No. 13/715,068, entitled "Endodontic Obturation System And Method", all of which are incorporated herein by reference.

STATEMENT REGARDING FEDERALLY SPONSORED RESEARCH OR DEVELOPMENT

Not Applicable.

BACKGROUND

1. Field

This application relates generally to obturation systems and methods for use during an endodontic (root canal) procedure to, for example, three-dimensionally seal and fill at least the apical end of a root canal after the root canal has been shaped, cleaned/disinfected, and dried.

2. Description of Related Art

A tooth comprises a crown, which is visible above the gum line, and one or more roots, which extend from the bottom of the crown. The tooth roots, and hence the tooth, are secured into bone by periodontal ligaments. Each root includes a canal that is filled with a living tissue, referred to as pulp. For a variety of reasons, the pulp can become diseased or otherwise become infected. Such infections adversely affect the tooth and its supporting structures. When the pulp in the root canals becomes infected, the tooth can be pulled (i.e., extracted).

Clinically, as an alternative to extraction, root canal treatment can be performed. Root canal treatment is directed toward preparing the root canal to eliminate the pulpal tissue, bacteria when present, and related irritants from the root canal system.

SUMMARY

Several embodiments of the invention are directed to facilitating successful outcomes for root canal procedures. Following root canal preparation and disinfection procedures, an objective for successful outcomes is for the root canal system to be three-dimensionally filled with an inert, biocompatible, dimensionally stable, obturation (filling/sealing) material, such as a gutta-percha, in an effort to eliminate space for bacteria to colonize. If bacteria are given space to form a colony in the root canal, the bacteria, their noxious by-products and toxins, and corresponding infection, can exit the root canal through the apex and other communications from the canal and spread into the surrounding tissues. Several embodiments of the invention are particularly advantageous because the obturation procedures will fill not just the main canal, but all or substantially all of the anatomy of the root canal system, including any fins, webs, cul-de-sacs and lateral canals present in the root canal system, and seal all the portals of exit between the root canal system and the tooth's attachment apparatus.

Briefly stated, the obturation system shown in the drawings and described below was designed for accurate sealing of at least the apical end of the root canal with a filler material (such as gutta-percha). The system can be configured to provide for near automatic sealing of the root canal. This is facilitated by, in some embodiments, a feedback system that includes location of the filler material's placement, direct heat delivery to the filler material for controlled transfer of heat and simultaneous three-dimensional forces of compaction. In one embodiment, the obturation system comprises a delivery device that at least partially wraps the filler material and extends to the tip (or with about 2 mm therefrom) of the filler material, a base unit, a holder which removably receives the delivery device and which is in communication with the base unit, a plugger, also with connection to the base unit, and a lip clip. As will become apparent, the disclosed plugger can be independent of the system or incorporated in the system. The plugger, or portions thereof, may be made of one or more the following materials: Nitinol (NiTi), memory wire or other materials which can withstand the forces to which the plugger will be exposed during use.

Briefly stated, according to one embodiment of the obturation system, a delivery device (e.g., a filler material delivery device) is provided for delivering a plug of filler material into a root canal. As described below, in one embodiment of the obturation system, the delivery device is operable to confirm that the plug of filler material is in position at the apex or working end of the prepared canal, and then to regulate the direct delivery of heat to the plug of filler material in the canal. The system then allows for a new three-dimensional form of molding of the filler material in the canal while the filler material is being heated, thus assuring that the filler material is at a moldable temperature while it is simultaneously molded into the root canal. Finally, the system will remove the delivery device while molding is completed, leaving only the filler material in the root canal.

In one embodiment, the delivery device comprises an elongate shaft extending from an upper gripping or connection portion. All or a portion of the delivery device comprises a material that has a thermal conductivity in the range of about 100 w/mK to about 2500 w/mK, e.g., between about 200-500 w/mK. In one embodiment, at least a portion of the delivery device comprises a material having a thermal conductivity sufficient to generate a temperature gradient of less than 20° C. (e.g., less than 15° C., less than 10° C., less than 5° C., etc.) from the proximal end of the filler material to the distal end of the filler material or a distance of about 5 mm to about 25 mm (e.g., about 5-10 mm, about 5-15 mm, about 5-20 mm). In one embodiment, at least a portion of the delivery device comprises one or more of a NiChrome alloy, silver or a silver alloy. The delivery device, or portions thereof, can comprise one or more of a solid sheet, a frame, mesh, struts, holes, pores, etc. In one embodiment, a bottom or distal portion of the shaft defines a bed portion to which a plug (e.g., a cone) of filler material (such as gutta-percha) is mounted. According to several embodiments, the delivery device extends to the tip of the filler material (or close to the tip) and wraps around part of the filler material at this distal end. One unique benefit of wrapping around the filler material is that this allows for the use of the plugger while the delivery device is in a root canal. By wrapping around the filler material, a portion of the delivery device can partially or fully wrap around the filler material. In other words, wrapping around the filler material does not necessarily mean that the filler material is entirely encapsulated. In some embodiments, the delivery device does not extend to the tip of the filler material, but is sufficiently proximate the tip of the filler material so as to deliver sufficient heat to the filler material. For example, in some embodiments, the delivery device extends from about 0.1 mm to about 2 mm from the tip of the filler material. The bed portion is heat conductive and/or includes a heating device, to allow for direct or indirect heating of the filler material along the length of the plug of filler material. The bed portion can be provided with one or more retentive features to help maintain the filler material on the bed portion until the filler material is heated. In accordance with one embodiment of the system, a temperature sensor can be placed on the bed portion, spaced from the apex or distal end of the plug of filler material. In accordance with another embodiment, a temperature sensor can be positioned on the plugger which is used in conjunction with the delivery device. The use of an optional temperature sensor allows for a temperature feedback loop, which allows for controlling of the temperature to which the filler material is heated.

In some embodiments, the delivery device is received within a holder. The holder, in some embodiments, is configured for compatibility with other devices (such as devices for heating the filler material and devices for plugging the filler material). The holder, in one embodiment, removably receives the delivery device. This can be manual or in accordance with one aspect of the system, the holder can be provided with a retraction device which is operable to axially move the delivery device relative to the holder. In one embodiment, when the delivery device is inserted in the holder, the delivery device is in an extended position. The retraction device is operable to retract (pull) the delivery member into the holder as part of the step of separating the delivery device from the filler material. Such a retraction device can comprise a linkage, a piston, an electromagnetic actuator, or any other device which can move the delivery device axially.

In accordance with another embodiment, the obturation system comprises a heating circuit and/or a temperature sensor, and a controller. The temperature sensor may be positioned to be in thermal communication with filler material during use and generates a signal indicative of the temperature of the filler material and/or the surrounding area. The heating circuit includes a heating member which is regulated by a controller to deliver heat to the filler material from the bed portion of the delivery device along, or substantially along, the full length of the filler material. Hence, the filler material is heated transversely along the filler material, rather than longitudinally (i.e., from the top down). This is particularly advantageous when heating filler materials that have limited ability to transfer heat, such as gutta-percha. Because the delivery device partially contacts the filler material along, or substantially along, its full length, it helps overcome the challenge of currently available heat delivery systems that attempt to transfer heat downwardly and through gutta-percha. In several embodiments, the invention is particularly advantageous over heat carriers that are placed in the center of the filler material and do not extend the length of the filler material. Although such designs may permit transfer of heat over systems that apply heat at the top of the filler material, they do not allow for simultaneous molding of the filler material as heat is applied. Additionally, confirmation of the position of the filler material is generally not viable, unless, as in several embodiments of the invention, the delivery device extends along the side and the full length, or substantially the full length, of the filler material. This feedback of the position of the filler material upon heat transfer and molding allows for controls to regulate precise conditions for ideal molding. In one embodiment, the controller is in communication with both the temperature sensor and the heating circuit to control the heating circuit, and hence the heating of the filler material, in response to the temperature output of the temperature sensor. If the temperature sensor is on the bed portion of the delivery device, the temperature sensor can be proximate the apex of the filler material. The controller controls the heating member to directly heat the filler material to a temperature at which the material becomes moldable.

In several embodiments, the controller system can be provided with a timer which is activated by the controller when the temperature sensor reaches the programmed, desired temperature. When the heat has been established and held for a predetermined time, the controller can either notify the practitioner for simultaneous manual molding or the holder can be provided with an automated plugger to mold the filler in place. As these functions are timed, sensed and regulated the controller can notify the practitioner to manually withdraw the delivery device or the holder can have a system to automatically withdraw the delivery device. The controller can also deactivate the heating circuit after the delivery device has been removed or after a predetermined time period (e.g., 2-10 seconds) has elapsed.

The system can also include an apex locating circuit which includes the delivery device, a lip clip and an impedance/resistance monitor. According to some embodiments, the apex locating circuit generates an output indicative of the position of the delivery device in the root canal. In the apex locating circuit, the delivery device can be the probe of the apex locating circuit. The delivery device can function as the probe for such a circuit because it is positioned along the side of the filler material and also because it extends the full length, or substantially the full length, of the filler material. In one embodiment, to enable the delivery device to be the probe of the apex locating circuit, the outer surface of the delivery device bed portion remains exposed when the filler material is mounted to the bed. In this manner, the outer surface of the delivery device will contact the wall of the root canal when the delivery device is in the root canal. Additionally, at least a portion of the outer surface of the bed portion is electrically conductive. The apex locating circuit generates an output indicative of the position of the end of the delivery device in a root canal based on the resistance/impedance of the apex locating circuit. In some embodiments of the system, the controller controls the heating circuit in response to the output of the apex location circuit as well. In particular, according to one embodiment, the controller will not activate the heating circuit unless the end of the bed portion, and hence the end of the filler material, is within a determined distance of the apical foramen of the root canal. Further, the controller can prevent activation of the heating circuit if it is determined that the apical end of the bed portion is in the tissue (e.g., extending through the apical foramen of the root canal).

In accordance with one embodiment, the plugger utilized for simultaneous molding can include one or more temperature sensors (such as a thermocouple) positioned at or near its working end so as to detect or sense the temperature of the material that is, for example, contacted by the plugger surface. The output of the temperature sensor of the plugger is received by the controller to enable the controller to regulate the temperature delivery along the device. In addition, the system can include an associated display which is in operative communication with the temperature sensor, such that the sensed temperature of the material which is contacted by the plugger surface is shown on the display. In one embodiment, the display is located on the handle of the plugger. In another embodiment, the display is remote from the plugger handle. In one embodiment, the plugger comprises a handle and a shaft extending from the handle. The shaft has a proximal end and a distal end, and the plugger defines a working end at the distal end of the shaft. The working end of the plugger comprises one or more central posts or stationary plates spaced from the distal end of the shaft by means of a post; and a plurality of movable plates which are movable relative to the stationary plate/post independently of each other. The movable plates can be connected to the shaft independently of the stationary plate/post and of each other. The moveable plates, in combination, at least in part, may surround the stationary plate/post. In one embodiment, the moveable plates and the stationary plate/post, in combination define a variable plugging surface that enables the circumferential size and/or shape of the plugging surface to be varied substantially instantaneously by contact with the wall of a root canal during an obturation procedure.

The movable plates can be connected to the distal end of the shaft by a connector which can be a wire, cable or the like. The connector, according to one embodiment, is made from a material which will deflect axially when horizontal forces are applied to allow the moveable plates to move in planes generally parallel to each other and to the stationary plate/post, and which will return to a normal position upon release of horizontal deflection forces.

The plugger post and connectors are selected to withstand typical compression forces to which they will be subject during an obturation procedure without buckling (for example, a load of up to about 7 lbs may be well tolerated).

In accordance with one aspect of the plugger, the moveable plates overlap each other at least in part and overlap the stationary plate/post at least in part. Illustratively, the moveable plates are generally parallel to each other and generally parallel to the stationary plate/post. As an example, the stationary plate/post can be generally circular, and the moveable plates can each have an arced outer edge.

In accordance with another aspect of the plugger, the plugger can be provided with a retraction button on the handle which is operably connected to the connectors, such that when the retraction button is pressed, the moveable plates will move toward the stationary plate and post such that the area of plugger surface is reduced. The retraction button can be used to reduce the effective size of the plugger's working surface to a smallest possible effective size.

In accordance with another aspect of the plugger, the plugger can be provided with a pressure transducer to monitor the forces being applied to mold the filler material. In accordance with one aspect, the applied force can be displayed for monitoring by a practitioner during obturation. In accordance with another aspect, the output of the pressure transducer can be received by the controller, and the controller can then control automatic molding of the filler material.

The obturation system can be provided with one or more displays. Displays can be provided on a base unit, and/or on the holder and/or on the plugger. The displays can be operated to display such things as the temperature of the filler material, the amount of time at such temperatures, the length of the heating period, when to mold manually or when automatic molding is occurring, the pressure or force applied to mold the filler material, when withdraw of the delivery device should be manually withdrawn or when automatically withdrawn, etc. In addition, the system can be provided with an input device (such as buttons) to enable the practitioner to adjust the set temperature to which the filler material is heated and to adjust the length of time the filler material is heated (e.g., the length of time the heating circuit is activated). The base unit can also be provided with a display the graphically shows the location of the delivery device (and hence the filler material) in the root canal.

In several embodiments, the main controller for the system can be located either in the holder or the base unit. Alternatively, the system can have a single controller for example, in the base unit, and the components can then communicate with the single controller. Such communication can be corded or wireless. Further, some components could be corded and others could be wireless.

In several embodiments, the obturation system has several advantages. First, the system delivers heat directly to the filler material along, or substantially along, the entire length of the filler material. This overcomes limitations that are present in systems that attempt to transfer heat longitudinally (i.e. through the filler material from top to bottom). This also allows for a more even heating of the filler material, and obviates the need for high temperature heating of the filler material. This is of clinical importance when using the filler material, such as gutta-percha, as temperature mediated phase changes occur at higher temperatures which lead to shrinkage when the material cools. By controlling the temperature of the filler material and not heating the filler material beyond its temperature mediated phase changes, the physical and mechanical properties of the filler material are able to be controlled and utilized. In particular, according to one embodiment, the ability to operate at temperatures below the temperature mediated phase transitions of the filler material reduces the possibility of the filler material shrinking as it cools, and thus reduces the potential for void formation between the filler and the root canal wall. Further, the system, according to one embodiment, advantageously allows for molding of the filler material while the filler material is being heated.

Another advantage of several embodiments is the location of the delivery device vis-à-vis the filler material. Since the delivery device is located along the side of the filler material in some embodiments, molding is allowed to occur simultaneously as heat is being delivered. In addition, in several embodiments, because the heat delivery device is on the outer surface of the filler material, it can be withdrawn after the heating period has ended and just prior to, or during molding.

Another advantage of several embodiments is the use of an apex locator. In some embodiments, the system utilizes apex location at the time of obturation or sealing. Apex location is facilitated by the position of the delivery device in some embodiments (e.g., extending along, or substantially along, the length of the filler material). The use of apex location at the time of obturation or sealing (as opposed to during shaping and disinfecting) enables the practitioner to be fairly certain that the filler material is properly positioned in the root canal prior to compaction or molding of the filler material. In addition, this additional feedback allows for controls to be placed within the overall system for a more precise and safe delivery of the filler material.

In several embodiments, a kit is provided. The kit comprises a delivery device according to any of the embodiments described herein, filler material according to any of the embodiments described herein, and instructions for coupling the filler material to the delivery device. Couplers may also be included (e.g., adhesive or other physical coupling mechanisms). In some embodiments, couplers are not needed because the filler material is configured to mate with the delivery device. In several embodiments, the delivery device may be disposable or reusable.

Briefly, and as discussed more fully below, an obturation system for facilitating filling of a root canal system, comprises, in one embodiment, a delivery device that comprises a shaft having a bed portion at a distal end thereof. The bed portion has an inner surface and an outer surface. A biocompatible filler material having an upper surface, a side surface, and a distal end is mounted to the inner surface of the bed. The delivery device has a greater thermal conductivity than the filler material, and is configured to transfer heat to the filler material such that the temperature difference along any two points on the filler material does not exceed more than 20° C. Additionally, the bed portion of the shaft wraps at least partially around the filler material and contacts the filler material substantially along the length of the filler material from the upper end of the filler material to at or proximate the distal end of the filler material to facilitate direct heat transfer to the distal end of the filler material, thereby facilitating heating of the filler material and delivery of the filler material to the root canal system. The filler material can comprise gutta-percha.

In accordance with an aspect of the system, the system can further comprise a heating device which is configured to deliver heat to the bed portion of the shaft, and thus to the filler material. Further the system can include a temperature sensor, and a controller. The temperature sensor is positionable to be in heat sensing contact with the filler material to transmit a temperature signal indicative of the temperature of the filler material. The controller is configured to be in communication with the temperature sensor to receive the temperature signal from the temperature sensor. The controller is further configured to be in communication with the heating device to control the heating device, and thus the heating of the filler material, in response to the output of the temperature sensor.

According to one embodiment, the system can be provided with a timer which is in communication with the controller. The controller activates the timer when the heating device is activated or upon the filler material reaching a predetermined temperature. The controller then deactivates the heating device after a predetermined period of time has elapsed. The predetermined period of time can be about 2 seconds to about 10 seconds.

The system, in one embodiment, can monitor the location of the delivery device in the root canal, and the controller prevents activation of the heating device unless the controller determines the apex of the filler material to be within a predetermined distance of an apex of a prepared root canal. In accordance with one aspect, the controller automatically activates the heating device to heat the filler material when it is determined that the apex of the filler material is at the apical end of a root canal or within about ¼ mm of the apical foramen of the root canal. Further, the controller can prevent activation of the heating device if it is determined that the delivery device extends through an apical foramen of the root canal.

The heating device is configured to deliver heat to the filler material to heat the filler material to a temperature of less than 75° C. to the upper surface of the filler material, e.g., between about 39° C. and about 65° C. or between about 42° C. and about 65° C., or between about 39° C. and about 60° C.

The system can include one or more temperature sensors located on the delivery device.

The system can, in an embodiment, comprise a plugger having a plugger surface configured to contact the filler material. The plugger can include a temperature sensor and/or a pressure transducer located on the plugger surface. Further, the plugger can be provided with a vibration generator positioned on the plugger to induce vibrations in the plugger surface.

A system as described above can further comprise an apex location confirming circuit. The apex location confirming circuit comprises the delivery device and a lip clip. The delivery device comprises an electrically conductive member extending along at least the outer surface of the delivery device bed portion and which will contact a surface of the root canal when the device is inserted in the root canal. The apex location confirming circuit generates a location signal indicative of the location of the delivery device in the root canal being treated. The controller is in operative communication with the apex location confirming circuit to receive the location signal.

In one embodiment, the system further comprises a holder adapted to removably receive the delivery device. In one embodiment, the holder includes the heating device to deliver heat to the delivery device and hence the filler material.

The holder can be provided with an axially movable retractor to which the delivery device is removably connectable. The retractor, in one embodiment, is operable to retract the delivery device from an extended portion to a retracted position and is being adapted to move the delivery device axially within the root canal a distance sufficient to withdraw the delivery device from the filler material. A controller is in operative communication with the retractor. The controller emitting a command to automatically activate the retractor after the filler material has been heated to a predetermined temperature for a predetermined period of time.

In an aspect of the system, the system comprises a plugger, a plugger driver and a controller. The controller is in operative communication with the plugger driver, and the plugger driver is controlled by the controller to axially move the plugger. The controller is configured to emit a command to activate the plugger driver to apply a molding pressure on the filler material while a heating device is activated. The plugger can be provided with a pressure transducer which generates a signal indicative of the pressure or force applied by the plugger on the filler material. The controller is in operative communication with the pressure transducer to control the plugger driver in response to the signals from the pressure transducer.

In accordance with another aspect of the system, the obturation system comprises a delivery device and a biocompatible filler material. The delivery device comprises a shaft having a bed portion at a distal end thereof, and which has an inner surface and an outer surface. The filler material comprises an upper surface, a tapered side surface and a distal end. The delivery device has a greater thermal conductivity than the filler material, and is configured to transfer heat to the filler material such that the temperature difference between any two points on the filler material does not exceed more than 20° C. The bed portion of the shaft extends along an outer surface of the filler material and contacts the filler material from the upper surface of the filler material to within about 2 mm from the distal end of the filler material to facilitate heat transfer to the distal end, thereby facilitating heating of the filler material and delivery of the filler material to the root canal system. The delivery device is comprised of platinum, silver, gold, copper, or aluminum or alloys thereof or other thermally conductive and/or electrically conductive metals or alloys. Alternatively, the delivery device can be coated, at least in part with platinum, silver, gold, copper, or aluminum or alloys thereof or other thermally conductive and/or electrically conductive metals or alloys. The filler material comprises a cone-shaped plug of gutta-percha.

The system, in one embodiment, further comprises a heating device which is configured to deliver heat to the bed portion of the shaft, and thus to the filler material.

The system further comprises a plugger and a controller, the controller being in operative communication with the plugger, and configured to emit a command to activate the plugger to apply a molding pressure on the filler material while a heating device is activated.

A method of facilitating filling of a prepared root canal system is disclosed in one embodiment and comprises the steps of confirming the position of filler material in the prepared root canal; activating a heating device to deliver heat to heat the filler material to a temperature in the range of about 39° C. to about 65° C. to heat the filler material in situ in the canal; and contacting the filler material with a plugger to facilitate molding of the filler material into the root canal system. The method can further include a step of maintaining the filler material at a temperature of about 39° C. to about 45° C. for a predetermined period of time.

A delivery device for delivering filler material to a prepared root canal as part of an obturation procedure is disclosed. In one embodiment, the delivery device comprises a shaft portion; and a bed portion at a distal end of the shaft portion. The bed portion comprises a filler material receiving surface and a pair of side edges. The filler material receiving surface is generally concave in shape. The side edges of the bed portion can slope downwardly and inwardly toward each other, such that the bed portion is generally triangular in shape. The bed portion can have a tapered outer surface. The generally concave shape of the bed defines a curvature; and this curvature can correspond generally to the curvature of a plug of filler material to be mounted on the bed.

The delivery device can comprise at least one retention feature to secure filler material to the bed. The retention feature can comprise (i) one or more holes which extend through the bed surface, and/or (ii) cutouts/indents formed in the side edges of the bed, and/or (iii) texturing of the bed surface, and/or (iv) bending of the side edges inwardly, and/or (v) flashing from the formation of the holes or cutouts/indents, and/or (vi) an adhesive and/or (vii) one or more rims.

The delivery device can include a connecting portion at a proximal end of the shaft portion. The connecting portion is adapted to connect the delivery device to a holder. The connecting portion can comprise a lock for removably securing the device to the holder. The lock can comprise one of a bayonet slot and a pin or one of a spring biased member and a groove which receives a spring biased member. The connecting portion can comprise a hollow tube.

According to one aspect, the delivery device is made from an electrically conductive material or has an electrically conductive coating on an outer surface of the device.

According to another aspect, the delivery device is made from a made a heat conductive material. The delivery can include a heating element located at the bed portion.

The delivery device can be provided with a plug of a filler material that is secured to the bed portion. The plug of filler material comprises an outer surface which is in contact with the receiving surface of the bed portion. The bed portion has an outer surface which remains exposed when the filler material is secured to the bed portion. A distal end of the bed is proximate the bottom of the plug of filler material. Alternatively, the practitioner can secure the plug of filler material to the bed of the delivery device prior to insertion of the delivery device and the filler material into the root canal. As a further alternative, during an endodontic (i.e., root canal) procedure, the practitioner can insert the delivery device into the prepared canal without the plug of filler material. The desired filler material plug can then be inserted into the canal. In this instance, the shape of the delivery device will act as a guide to facilitate insertion of the plug of filler material into the prepared root canal.

In accordance with another aspect, a system for filling and sealing an apical end of a prepared root canal is disclosed. The system comprises a delivery device and a heating circuit. The delivery device comprises a shaft portion and a bed portion at a distal end of the shaft portion. The bed portion has an inner surface and an outer surface. The inner surface is adapted receive filler material, and the outer surface remains exposed when the filler material is mounted to the inner surface. The bed has a length at least substantially equal to the length of the filler material to be mounted to the bed. The heating circuit comprises a heat device operable to deliver heat to at least the inner surface of the bed, such that the filler material is heated transversely substantially along the length of the filler material when the heating circuit is activated. At least the bed of the delivery device is made from a heat conductive material.

In accordance with an aspect of the system, the heating circuit can comprise a heating element located at the bed.

In accordance with an aspect of the system, the system further includes a controller which is in communication with the heating circuit to activate and deactivate the heating circuit. The controller, upon activation, activates the heating circuit for a predetermined period of time. The system can include a temperature sensor in communication with the controller and which is in heat transfer relationship with the filler material when in use. The temperature sensor transmits to the controller a signal indicative of the temperature of the filler material being heated, and the controller controls the heating circuit in response to the signal from the temperature sensor.

In accordance with an aspect of the system, the system can include an apex locating circuit which is in communication with the controller. The apex locating circuit transmits a signal indicative of the location of the delivery device in a root canal, and the controller activates the heating circuit in response to a location signal received from the apex locating circuit. The delivery device can comprise a probe of the apex locating circuit.

A method for heating a plug of filler material in situ in a root canal is disclosed wherein the filler material, in one embodiment, is coupled to the inner surface of a bed of a delivery device such that an outer surface of the delivery device bed remains exposed, and wherein the bed has a length at least substantially equal to the length of the filler material. The method comprises transferring heat from the bed to the filler material to transversely heat the filler material substantially along the length of the filler material to a temperature slightly above the molding temperature of the filler material. In accordance with one aspect of the method, the filler material comprises gutta-percha and the method comprising heating the filler material to between about 37° C. and about 65° C., or between about 39° C. and about 50° C. In one embodiment, the step of transferring heat from the bed to the filler material comprising activating a heat element located at the bed. In another embodiment, the step of transferring heat from the bed to the filler material comprising heating the bed, the bed being made of a heat conductive material. The heating step is carried out for less than 10 seconds, e.g., about 3-5 seconds. In accordance with an aspect, the heating step is electronically controlled by a controller, and the controller initiates the heating step in response to a signal received from an apex locating circuit confirming that the charge of filler material is at an apex of a prepared root canal.

A method of sealing at least the apical end of a prepared root canal is disclosed. The method, in one embodiment, comprises heating a biocompatible thermoplastic filler material in a prepared root canal to a moldable temperature. The heating step comprises heating the filler material from a side of the filler material and along substantially the full length of the filler material. The method further includes at least partially molding the heated filler material into the apical end of the root canal while the filler material is being heated to three-dimensionally seal the apical end of the root canal. Heating of the filler material comprises heating the filler material such that it is substantially of a constant temperature throughout the filler material, such that there are substantially no temperature gradients in the filler material, either from side-to-side or from top-to-bottom. In accordance with an aspect of the method, the filler material is a gutta-percha. Further, the filler material can be a cone-shaped plug of gutta-percha. If the filler material is gutta-percha, gutta-percha filler material is heated to a temperature of between about 37° C. and about 65° C., or between about 39° C. and about 50° C., or between about 39° C. and about 45° C. The method can further comprise a step of monitoring the temperature of the filler material and controlling the heating of the filler material in response to the monitored temperature of the filler material.

In accordance with an aspect of the method, the method includes a step of confirming that the filler material is within a predetermined distance of the apical end of the root canal prior to commencement of the step of heating the plug of filler material. Stated differently, the heating step is not initiated unless it is determined that the end of the plug of filler material is within a determined distance of the apical end of the root canal.

In accordance with one aspect of the method, the filler material is mounted to a delivery device, and the step of applying heat to the filler material comprises heating a distal end of the delivery device. The method further includes a step of withdrawing the delivery device from the filler material after the filler material has been heated to a desired temperature for a predetermined period of time, which can be about 2 to about 10 seconds. In accordance with an aspect of the method, the delivery device is automatically moved axially in the canal to separate the delivery device from the filler material.

In one embodiment, the step of molding the filler material comprises inserting a plugger into the root canal prior to commencement of the step of heating the filler material. In an embodiment, the method can include vibrating a working end of the plugger while the plugger is molding the filler material.

A holder for a delivery device for delivering filler material into a prepared root canal is disclosed. The holder, in one embodiment, comprises a body, a mounting portion adapted to removably receive the delivery device; and a heating circuit having a heating device wherein the heating device is positioned to be in thermal communication with the delivery device when the delivery device is mounted to the holder.

In a first illustrative embodiment of the holder, the mounting portion comprises a pair of arms extending from the body; the arms being deflectable to be urged together under a squeezing pressure. In this embodiment, the arms each have a grasping portion at a distal end of the arms which is adapted to grasp the delivery device when the arms are squeezed together.

In an alternative illustrative embodiment of the holder, the mounting portion comprises an elongate nose extending from the body. The nose can be comprised of a heat conductive material, in which case, the heating device is operable to transmit heat to the nose. In accordance with another aspect of this second embodiment, the nose is at least in part electrically conductive.

In a further illustrative embodiment of the holder, the mounting portion comprises a channel in the holder body which is sized to removably receive a distal end of the delivery device. In this embodiment, the heating device is proximate the channel. In one aspect, the holder can comprise a retracting member in the channel which is movable axially relative to the chamber and which is adapted to be removably connected to the delivery device when the delivery device is received in the mounting portion.

In accordance with a further aspect of the holder, the holder can include a plugger which is axially movable relative to the channel. The holder includes a plugger driver operable to axially move the plugger between an extended position and a relaxed position.

In accordance with another aspect of the holder, the holder can include at least a portion of an apex location circuit.

An endodontic plugger is disclosed which comprises, in one embodiment, a handle and a shaft extending from the handle. The shaft has a proximal end and a distal end, and the plugger defines a working end at the distal end of the shaft. The working end of the plugger comprises a plurality of movable plates that are independently operably connected to the shaft. The plurality of moveable plates, in combination, defines at least a portion of a variable plugging surface. The moveable plates are independently movable relative to each other, enabling the circumferential size and/or shape of the plugging surface to be varied substantially instantaneously due to contact with the wall of a root canal during an obturation procedure.

In accordance with an aspect of the plugger, the endodontic plugger can further include a stationary surface spaced from the distal end of the shaft by means of a post. The stationary surface can be generally circular. The movable plates surround at least a portion of the stationary surface and are movable relative to the stationary surface. In an embodiment, the stationary surface can be defined by a plate mounted to a distal end of the post.

In accordance with an aspect of the plugger, the moveable plates are movable in two degrees of freedom.

In accordance with an aspect of the plugger, the moveable plates are generally parallel to each other.

In accordance with an aspect of the plugger, the moveable plates overlap each other in part.

In accordance with an aspect of the plugger, the moveable plates each have an arced outer edge.

In accordance with an aspect of the plugger, the moveable plates are independently connected to the shaft by a connector, there being at least one connector for each moveable plate. The connector is made from a material which will deflect to allow the moveable plates to move in planes generally parallel to each other, and will return to a normal position upon release of deflection forces. The connectors are made from a material which can withstand typical compression forces to which the connectors will be subject during an obturation procedure without buckling. In accordance with an aspect of the connectors, the connectors buckle if a load of more than a predetermined amount is applied to the plugger. The predetermined amount of load is up to about 7 lbs. In accordance with a further aspect of the connectors, the connectors each extend generally downwardly and outwardly from the distal end of the shaft to the moveable plates.

In accordance with another aspect of the plugger, the plugger comprises a retraction button on the handle which is operably connected to the connectors; whereby when the retraction button is pressed, the moveable plates will move inwardly toward each other such that the area of plugger surface is reduced.

In accordance with an aspect of the plugger, the plugger can comprise a temperature sensor on the plugger surface and an associated display. The temperature sensor is in operative communication with the display, such that the display displays the temperature of the material which is contacted by the plugger surface. The display can be located on the handle of the plugger or remote from the plugger handpiece. The temperature sensor can be located on the stationary plate. The temperature sensor can be a thermocouple.

In accordance with an aspect of the plugger, the plugger can further comprise a pressure transducer which is positioned on the plugger so as to generate a signal indicative of the force applied to an object by the moveable plates. The pressure transducer can be in communication with an associated display, such that the display displays the pressure or force applied to the material which is contacted by the plugger surface. The display can be on the plugger handle or remote from the plugger.

In accordance with an aspect of the plugger, the plugger can comprise a vibration generator. The vibration generator is positioned on the plugger and is adapted to induce vibrational energy in the movable plates.

In accordance with an aspect of the plugger, the endodontic plugger comprises a handle and a shaft extending from the handle. The shaft comprises a proximal end and a distal end, wherein the distal end of the shaft defines a plugger surface. A temperature sensor is located on the plugger in a position to place it in heat transfer relationship with a material to be contacted by the plugger surface and is configured to emit a signal indicative of a temperature of the material contacted by the plugger surface. The plugger additionally includes a display in operative communication with the temperature sensor; the display being configured to display the temperature of the material contacted by the plugger surface. In an embodiment, the temperature sensor is located on the plugger surface. The display is located on the handle of the plugger or is remote from the plugger handpiece. The display operatively communicates wirelessly with the temperature sensor. The temperature sensor can be a thermocouple.

A method of obturating a root canal that has been shaped, cleaned and dried is disclosed. The method comprises, in one embodiment, the steps of engaging a plug of heated filler material placed in the root canal with a working surface of a plugger, applying a molding/packing force to the plug of filler material while the filler material is above a predetermined temperature, monitoring the temperature of the filler material while the surface of the plugger is in contact with the filler material, and stopping the application of the compressive force to the filler material after it is determined that the temperature of the filler material has fallen below a predetermined temperature.

In accordance with one aspect of the method, the plugger comprises a handle and a temperature sensor at the working surface of the plugger. The temperature sensor is in operative communication with a display and transmits a temperature signal. The display displays the temperature of the filler material based on the signal from the temperature sensor. The method comprises displaying the temperature of the filler material while the surface of the plugger is in contact with the filler material. The temperature sensor can provide data to a controller to regulate the temperature delivered to the filler material.

In accordance with an aspect of operating the plugger, the method comprises displaying a temperature of a root canal filling material while the plugger is in contact with the root canal filling material. The plugger can comprise a handle with a display on the handle, in which case, the method comprises displaying the temperature of the filling material on the display.

In accordance with a method of operating the plugger defining a plugger surface during an obturation procedure, the method comprises, in one embodiment, automatically and substantially instantaneously adjusting the size and/or shape of the plugger surface in response to the cross-sectional size and/or shape of a root canal as the plugger surface passes along the root canal.

BRIEF DESCRIPTION OF THE DRAWINGS

FIGS. 6A and 6B are basic electrical schematics for the apex locating circuit and the heating circuit, respectively, used in the holder;

FIG. 7A is a perspective view of an alternative embodiment of the obturation system showing a delivery device and holder therefore, a plugger and a lip clip, with the delivery device and plugger shown in a root canal;

FIG. 7B is a side perspective view showing connection of cords for the lip clip and holder;

FIGS. 7C-E are perspective, side elevational and front elevational views, respectively of a base unit of the obturation system of FIG. 7A;

FIGS. 8A-B are perspective and elevational views of a delivery device of the obturation system of FIG. 7A;

FIGS. 9A-C are horizontal cross-sectional views of the delivery device taken at lines A-A, B-B and C-C of FIG. 8A;

FIG. 9D is an enlarged view of the distal end of the delivery device showing the position of a heat sensing element on a plug/cone of filler material;

FIG. 12 is a plan view of the bed portion of the delivery device of FIG. 10A, showing two types of retentive features which can be applied to the bed portion;

FIG. 13 is a schematic vertical cross-sectional view of the distal end of the delivery device of FIG. 10A;

FIGS. 14A-B are horizontal cross-sectional views through the bed portion of the delivery device of FIG. 10A, showing two alternative retentive features FIGS. 15 and 16 are enlarged perspective views showing the connecting portion of the delivery device of FIG. 10A;

FIG. 17A is a perspective view of a second illustrative embodiment of the holder;

FIGS. 17B-D are rear, front, and side elevational views, respectively, of the holder of FIG. 17A;

FIG. 17E is a schematic cross-sectional view of the holder of FIG. 17A;

FIG. 18 is a schematic cross-sectional view of a variation of the holder of FIGS. 17A-E;

FIG. 19 is a perspective view of a plugger for use with the obturation system;

FIG. 20 is a cross-sectional view of the plugger taken along line A-A of FIG. 19;

FIG. 21 is an enlarged side elevational view of the working end of the plugger taken at circle B of FIG. 19, showing the individually adjustable plates of the plugger in an opened or expanded configuration;

FIG. 22 is an enlarged perspective view of the working end of the plugger;

FIG. 23 is a plan view of the working end of the plugger with the moveable plates in an open or expanded configuration;

FIG. 24 is a plan view of the working end of the plugger with the moveable plates of the plugger in oval configuration;

FIG. 25 is a plan view of the working end of the plugger with the moveable plates in a closed or retracted configuration;

FIG. 26 is a view of the plugger similar to that of FIG. 22, but showing the position of a temperature sensor on the plugger;

FIG. 27 is a view of a plugger with a standard end and provided with a temperature sensor;

FIG. 28 is a view of the working end of the plugger with an alternative configuration of the moveable plates, wherein gaps exist between the moveable plates and a stationary plate when the moveable plates are in the expended position;

Corresponding reference numerals will be used throughout the several figures of the drawings.

DETAILED DESCRIPTION

Figure 1:
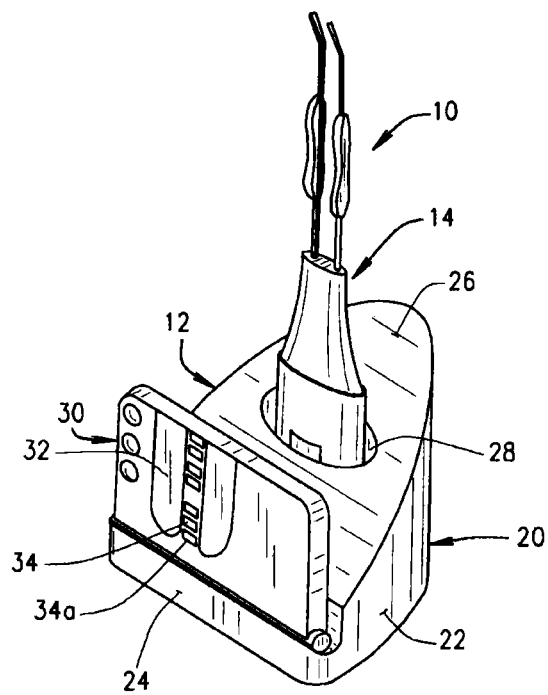
FIG. 1 is a perspective view of an illustrative embodiment of an obturation system.

In a root canal procedure, the practitioner prepares an access cavity through the crown of the tooth to the pulp chamber in the canal(s). The practitioner then removes the pulp from the canal(s) and shapes the canal(s). Shaping of the canal(s) is typically performed with a series of metal files. Chemical reagents are used to disinfect, dissolve and clean all aspects of the root canal system. Root canals do not define a single smooth path. Canals are often curved, rather than straight. In addition the root canal system may include fins, webs, cul-de-sacs and lateral canals. Ideally, the shaping, cleaning and disinfecting stage removes the pulp, bacteria and other irritants from all aspects of the root canal system, including any fins, webs, cul-de-sacs and lateral canals that may be part of the root canal system, not just from the main canal.

After the canal system has been shaped, cleaned, disinfected and dried, the root canal system is ready to be sealed with a filler/sealing material. Gutta-percha is (and has been) the most common material used for sealing the root canal system. Once the root has been filled and sealed, the access cavity formed in the crown is restored with a bonded restoration.

There are several methods employed to seal root canal systems. The oldest and still most common way to seal a root canal system is referred to cold lateral condensation. This technique places a piece of filler material in a prepared canal that roughly matches the shaped canal. Subsequent pieces of filler material are jammed in the canal after an instrument laterally jams the material to the side. This technique has downfalls in its ability to three-dimensionally seal the vast array of random internal anatomy present. Another common technique is to simply place a single cone-shaped plug of filler material into the canal. Although most techniques discussed here utilize a sealer material as well, this technique relies more heavily on the sealer to fill in the three-dimensional spaces of the canal. This technique has limitations in its ability to accurate and densely seal root canal systems.

In some cases, filler material is commonly provided as a generally cone-shaped plug, and the filler material plugs are provided in varying diameters and tapers. The practitioner selects the filler material plug based on its diameter and taper, and cuts the filler material plug to length so that it fits the shape of the apical end of the prepared canal. This technique of fitting a so-called "master cone" can be time consuming and subject to error. Typically, the filler material plug is adjusted (trimmed and sized) based on information the practitioner gains in the shaping procedure. For example, the practitioner attempts to match the instrument/file used to shape the canal during preparation for obturation. The practitioner typically must utilize knowledge of the length of the canal gained in the preparation of the canal (so that the practitioner knows how long the filler material plug should be). During the shaping of the canal the practitioner can use an apex locator. This apex locator is able to give the practitioner information as to the length of the main canal by analyzing changes in resistance and impedance measured with the use of files during the shaping procedure. This apex locator is a separate tool, and used in conjunction with electrically conductive devices, such as files, that extend to the end of the root canal. Currently, to the best of Applicant's knowledge, apex locator technology is not used in conjunction with filler materials. The practitioner also determines that the filler is properly fitted to the apical extent of the canal through a tactile feeling of "tug back". This arbitrary feeling aims to confirm that the filler material fits well at the estimated length of the canal. Once the filler material plug has been appropriately sized, it is heated from the top of the filler material and pressed to mold the filler material plug to seal the root canal. This technique has limitations in the ability to directly deliver heat to deep levels of the filler material. For instance, gutta-percha does not have the capacity to transfer heat past a few millimeters. Therefore, in an attempt to heat the entire plug, the top of the plug is typically heated to high temperatures (e.g., 200-300° C.) even though gutta-percha has been shown to be moldable at temperatures as low as 39° C. A further complication of such high temperature is that gutta-percha's temperature mediated phase transition has been shown to occur at levels as low as 42° C. (depending on formulation and brand) with an additional amorphous temperature mediated phase change that occur at levels reported as low as 53° C. Again, the actual temperatures at which gutta-percha goes through these phase transitions are within a range and reported differently based on the variation of gutta-percha evaluated. When gutta-percha is heated beyond these temperature mediated phase transition temperatures, the gutta-percha will shrink as it cools. This shrinkage can cause gaps to form between the gutta-percha filler and the root canal wall. As can be appreciated, the formation of gaps in a filled root canal is undesirable. Hence, the temperatures used by such heating devices are well in excess of temperatures needed for molding gutta-percha and they are far above gutta-percha's temperature mediated phase transition temperatures which lead to shrinkage. Several embodiments of the present system are particularly advantageous because moderate to low temperatures (e.g., in the range of about 39° C. to about 65° C., and up to about 100° C.) may be used. Higher temperatures may be used in one embodiment, but are typically not needed.

Another device commonly used to seal root canal systems, which utilizes very high temperatures, is a filler material extrusion device. Extrusion devices necessitate heating the filler material, namely gutta-percha, to high enough temperatures (e.g., above 160° C.) to allow for the filler material to flow through a chamber. These devices are most commonly used to fill coronal aspects of a canal once the apical end of the canal is sealed in an effort to not inadvertently flow excessive material beyond the canal.

Additionally, delivery devices have been developed that allow for a "carrier" to deliver the filler material into the root canal. Once the fit is estimated to be appropriate the device is heated in an oven, and then inserted into the canal. Although this technique allows for a more thorough heating of the filler material there are many downfalls to this technique. First, the material is in two different states from when it is estimated for fit to when it is put in for final placement; that is, it is cold and solid when initially estimated to fit and then warm and more liquid (or more fluid) when inserted into the canal. A common complication is the filler material coming off during the final placement. Second, this final placement is a one shot deal. There is little or no room for adjustment if the final placement ends short or long of the desired position. Third, as can be appreciated, when a heated plug is inserted in the canal, there is no other source of heat, and the filler material plug must be molded into the canal before it cools. Fourth, there are disadvantages related to the retention of the carrier, which include, but are not limited to being in the way of other restorative materials use to bond within and over the sealed root canal.

Finally, removable heat delivery devices have been mentioned. These removable delivery devices are theorized to allow for placement of the filler as well as for delivery of heat to the filler. These devices are centrally placed within the filler material and do not extend to the tip. Although this would allow for a more controlled delivery of heat while the device and filler material are within the root canal, they do not allow for molding to occur while the delivery device is in place; that is, a molding device, such as a plugger, cannot be brought into the root canal until the centrally placed delivery device is withdrawn. Moreover, since this type of system does not position the delivery device at the outer border of the filler material and as it does not extend to, or near to, the tip of the filler material the use of the apex locator during placement and at the beginning of the molding/sealing of the root canal is not possible.

Several embodiments of the invention are particularly advantageous because the delivery device enables the practitioner to perform an apex location when the filler plug is in the canal, enabling the practitioner to be more certain of the position of the plug in the canal prior to molding of the plug. Several embodiments provide a system that allow for molding at the time of the heat delivery and at the time the delivery device is withdrawn. Some embodiments comprise a device that allows for a direct temperature delivery along the entire length, or substantially along the length, of the filler material, thereby eliminating the need for the high heat used by currently available heating devices. In one embodiment, the invention is beneficial because it has some or all of the advantages described above.

In one embodiment, the device (i) can be used to confirm that the filler material is properly positioned in the root canal at the time of molding of the filler material, and (ii) enables for a thorough and precise heating of the filler material along the entire length, or substantially the entire length, of the plug of filler material in situ and which would avoid the need for high temperatures.

In addition to a delivery device system which allows for these functions, it would be advantageous, in some embodiments, to increase the functionality of pluggers currently employed. During filling and sealing of the root canal, the practitioner positions filler material in the canal and attempts to mold the filler material into the canal so that the filler material fills and conforms to the canal space. Often an instrument, such as a plugger, is used to mold the filler material into the root. The plugger typically has a flat end so that it can press the filler material in place into the prepared, cleaned/disinfected and dried canal. The plugger has an end with a set or fixed diameter which is typically round and which is smaller in diameter than the diameter of the root canal, and smaller in diameter than the coronal-most end of the filler material plug. As can be appreciated, when the heated filler material is compressed in the root canal, the filler material will not be constrained axially. That is, nothing prevents the filler material displaced by the plugger from moving coronally axially (i.e., toward the tooth crown) in the canal around the plugger. This coronally-directed axial flow of the filler material in the root canal makes proper filling and sealing of the root canal difficult.

A prepared canal is tapered, and has a diameter that decreases from top to bottom. Pluggers, as noted, have ends that are of a determined diameter, and come in different diameter sizes (e.g., 1 mm, 0.9 mm, 0.5 mm, etc.) Because the diameter of the plugger is set, a specific plugger cannot be pushed too far into the canal. If the plugger is pushed too far into the canal, the plugger will engage the wall of the root canal and exert lateral forces against the root canal wall, which can lead to a fracture of the root canal. The practitioner therefore selects a series of pluggers of different sizes to compress the filler material, and monitors the depth to which the pluggers are inserted into the canal in an effort to avoid inadvertent locking of the plugger into the root and excessive application of lateral forces to the root canal wall.

Several embodiments of the present invention provide a plugger that facilitates a safer method for molding filler material. In one embodiment, the plugger universally adapts/conforms to the various root canal shapes/sizes present in the prepared root canal. This may also increase forces of safe compaction by reducing the amount of filler material moving axially and coronally around the plugger as the filler material is pressed into the canal. In one embodiment, the plugger would also simplify the obturation process in that the practitioner could use a single plugger, rather than the multiple pluggers which are currently used.

Referring now to the drawings, an illustrative embodiment of an obturating system 10 is shown generally in FIG. 1. The system 10 comprises a base 12 and a holder 14 for a filler material delivery device 16. The base 12 comprises a body 20 having a side surface 22, a front surface 24 and a top surface 26. The base 12 is shown to have a sloping top surface and a side surface which curves from one end of the front surface to the other, to give the base a pleasing aesthetic appearance. The base 12 can be given virtually any desired shape. A receptacle 28 is formed in the top surface of the base and extends into the base 12. The receptacle 28 is shaped to receive the holder 14, and sized such that the holder 14 can stand on its own when inserted in the receptacle 28. Optionally, a display 30 is mounted to the front of the base 12. The display 30, as shown, is pivotable about the bottom of the display, such that the angle of the display relative to the vertical can be altered, to enable a practitioner to adjust the viewing angle of the display. The display 30 may include an image 32 of a tooth with a lighted scale 34 in the canal of the tooth. As will be explained below, the lighted scale indicates how far into the root canal the delivery device has been inserted. The scale 34 may include a "green" or "go" section 34a proximate the apex of the root canal which will be activated when the system senses that the apex or distal end of the delivery device 16 is in a "favorable zone", that is, when the distal end of the delivery device is within a predetermined distance of the apex (or apical foramen) of the canal (about ¼ mm-½ mm from the apical foramen) and not extending through the apical foramen or otherwise in contact with tissue.

Although not shown, the base 12 includes an electrical cord to enable the base to be plugged into an electrical wall socket. Alternatively, the base could be battery powered (so as to be cordless). Internally, the base includes a circuit board having a controller 36 (FIG. 5) which is in electrical communication with the display 30 to drive the display 30. The base controller 36 is also in communication with the holder 14 to receive at least location data from an apex location circuit in the holder, which is described below. This location data will be used by the controller 36 to drive the display 30. The connection between the holder 14 and the base unit 12 (and hence the controller 36) can be a corded connection or a wireless connection. If the connection is wireless, the base unit 12 and holder 14 will each be provided with a transceiver to enable the controller 36 to transmit commands to, and receive data from, the holder 14. In addition, if the holder is wireless, the base 12 will include a charging circuit to charge batteries contained within the holder 14. Such a charging circuit can include appropriate contacts in the receptacle 28.

Figure 2:
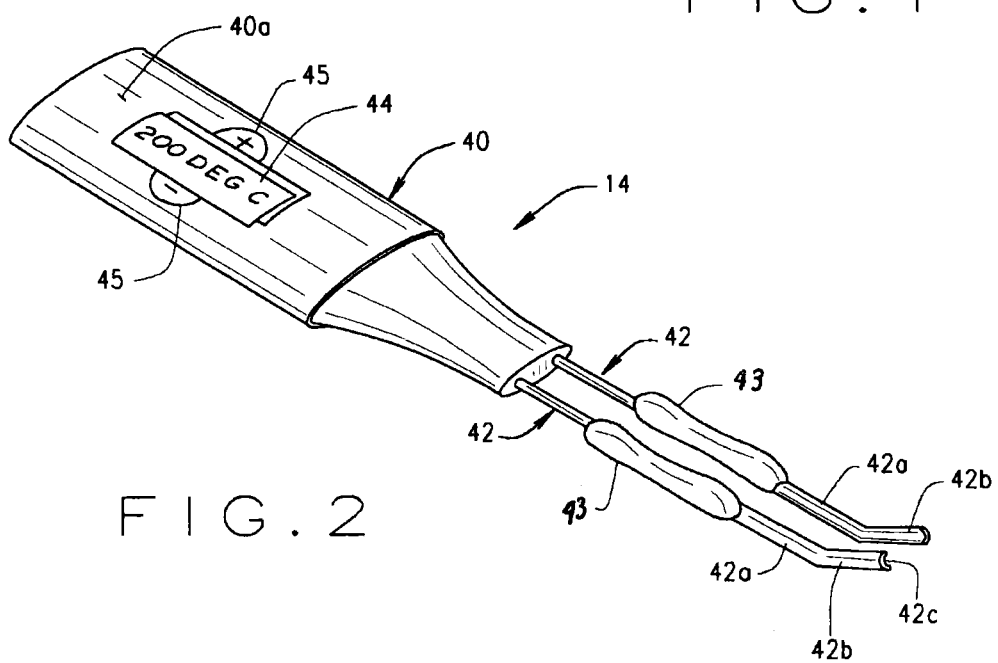
FIG. 2 is a perspective view of an illustrative embodiment of a holder of the obturation system FIGS. 3A-C comprise a perspective, cross-sectional schematic and elevational schematic views of an illustrative embodiment of a disposable filler material delivery device of the obturation system.

The holder 14 is shown generally in FIG. 2. As seen, the holder 14 comprises a body 40 with two arms 42 extending from the forward end of the body 40. The arms 42 are flexible and/or moveable such that they can be urged toward each other to be used like a tweezers or forceps. When released, the arms 42 will spring back to a rest position in which the arms are generally normal to the end of the holder body 40. The body 40 is shown to be generally oblong in cross-section, such that it has a generally flat surface 40a. A display 44 formed in the surface 40a displays data regarding the obturation procedure, such as the temperature of the filler material cone or plug proximate the end of the filler material (e.g., cone/plug), as will be explained in more detail below. The holder body 44 is also provided with input means 45, in the form of buttons, to program a set temperature for a heating circuit and/or a time limit for a timer.

Figure 4:
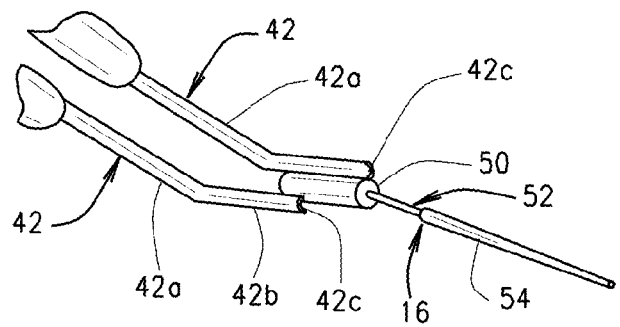
FIG. 4 is an enlarged fragmentary view of the holder in the process of grasping the delivery device.

The holder arms 42 each include an elongate portion 42a with a finger or grasping member 42b extending from the end of the elongate portion 42a. The fingers 42b each have a concave inner surface 42c (as best seen in FIG. 4) to facilitate grasping of the delivery device 16. To this end, the concave inner surfaces 42c of the arms 42 face each other. The fingers 42b are shown to be angled relative to the elongate portions 42a. The angle defined by the fingers 42b and the elongate portions 42a of the arms 42 is formed to facilitate insertion of the delivery device 16 into a tooth canal while holding the holder 14 in a comfortable manner. The holder 14 can be provided with finger rests or grips 43 partway along the length of the arm. One of the grips 43 may be provided with a switch 46 (FIG. 6B), such as a pressure switch which can be used to activate a heating circuit and/or an apex location circuit, or a complete obturation cycle, as will be described more fully below.

The system 10 also includes a lip clip 48 (FIG. 6A) which forms part of the apex locating circuit. The lip clip 48 can be connected (preferably, removably connected) to the holder by means of a cord. Alternatively, the lip clip can be connected to the base unit 12 by a cord.

Turning to FIGS. 3A-C, the delivery device 16 comprises a cylindrical body or connecting portion 50 and a shaft 52 extending from the body or connecting portion 50. The shaft 52 comprises a stem portion 52a extending from the connecting portion 50 and a mounting or bed portion 52b at the distal end of the shaft to which a plug or cone 54 of filler material (such as a gutta-percha) is mounted. The filler material 54 is comprised of a biocompatible thermoplastic in one embodiment. For example, the filler material can be comprised of a gutta-percha (e.g., polyisoprene). Other biocompatible thermoplastic sealing compositions could be used instead of, or in addition to, gutta-percha. The connecting portion 50 is shown to be generally cylindrical (but can be differently shaped if desired), and is sized to be grasped by a practitioner. The shaft 52 is shown to comprise a generally circular rod, but this could take on any configuration. For example, the shaft 52 could be circular and thin in configuration so as to not get in the way of a plugger also coming into position for molding when the device is positioned in the tooth. As seen, the filler material 54 is mounted to the distal end or bed portion 52b of the shaft, and the bed portion 52b extends along the exterior of the of filler material 54 (e.g., a cone/plug) the full length of the cone/plug 54, such that at least a portion of the bed portion 52b is exposed. Preferably, the end of the bed portion 52b is generally even with the end or apex or distal end 54a of the filler material 54. As seen in FIG. 3B, the bed portion 52b is embedded into the side of the filler material 54 such that about one-half the diameter of the bed portion 52b extends from the side of the filler material 54. As such, when the delivery device is inserted in a root canal, the shaft will be substantially against the wall of the root canal, rather than in the center of the root canal. This will allow for the introduction of a plugger, as just noted above, to allow the practitioner to at least start molding the filler material while the delivery device is still in the root canal.

As seen in FIG. 3A, the stem portion 52a can be bent as at 52d to define an upper short portion 52c which is concentric with the connecting portion 50 and angled relative to a main or lower part of the stem portion 52a. The angle 52d is sized to facilitate insertion of the delivery device into a root canal by a practitioner. If desired, the shaft 52 (and thus the stem portion 52a) could be provided straight. If straight, the shaft 52 could be bendable so that the practitioner could form the shaft to a desired configuration. The shaft 52 is, at least at its distal end, sufficiently thin, so that the end of the shaft 52 can reach to the apex of the root canal with the filler material (e.g., cone/plug) adhered thereto. Additionally, root canals are not typically straight. Thus, the shaft 52 is made from a material that is sufficiently flexible to enable the shaft to navigate turns and curves in 3 dimensions in the root canal, while at the same time, to be sufficiently rigid to support the filler material 54 so that the practitioner can insert the filler material 54 into a prepared tooth root canal while grasping the delivery device connecting portion 50.

A temperature sensor 56 (FIG. 3C), such as a thermocouple, thermistor, micro temperature probe, micro-chip sensor, etc., can be mounted to the bed portion 52b rearwardly of the apex 54a of the filler material 54 to provide an indication of the temperature of the bed portion 52b and of the filler material proximate the apex of the filler material 54. Importantly, the temperature sensor 56 is in thermal communication with the filler material 54 so that the temperature sensor will transmit a signal indicative of the temperature of the filler material. For example, the temperature sensor can be positioned about 3 mm (about 0.1") above the apex of the filler material 54. Although this would allow for a very precise measurement of the apical temperature, temperature sensors could be placed in other areas of the delivery system and allow for similar high level calibrations of the apical temperatures. Temperature sensors other than those disclosed above and which can be made small enough to fit into a root canal can be used as well.

As will be discussed in more detail below, the obturation system 10 is designed to better control the placement of the filler material in relation to the end of the root at the time of obturation as well as directly establish and control temperature delivery to the apical filler material. This will establish better molding parameters in deep levels of the root canal system and therefore allow for a better seal of the distal or apical end of the root canal. However, because canals are of varying length, this system may seal the entire canal in some cases. This would occur, for example in shorter canals. Therefore, in addition to better controlling the parameters in the apical ⅓ of the root canal, the system could be utilized to seal an entire canal. In an alternative embodiment, the system could also fill the remaining canal directly after or upon the sealing the apical end if the holder was also equipped with a filler material extrusion device. Such filler material extrusion devices are common, but are typically only used after the apical end of a root canal is sealed, as discussed above.

The filler material 54 is about 4 mm-12 mm long, preferably about 8-10 mm (about 0.3") long, as supplied and will be provided in various sizes/tapers. In other dental and non-dental embodiments, the filler material may be smaller or significantly larger. In some embodiments, the apical size of the filler material will be designed to match the main shape of the prepared canal (or other desired target site, whether in dental or non-dental tissue cavities). Said differently, the filler material will be made to match the size/taper of various files used to prepare the canal or other desired location, and the filler material will be provided in different sizes to facilitate matching the filler material to the shape of the prepared canal.

The connecting portion 50 of the delivery device will be about 8-12 mm long in one embodiment. The shaft 52 can vary in length to allow for various overall lengths corresponding to the various lengths of individual canals. Therefore, the length of various the sizes of delivery devices 16 will vary mainly in the length of the shaft 52. The overall length of the various sizes of the delivery device 16 will be in a range of 20-45 mm. The shaft 52 is, at least at its distal end, sufficiently thin, so that the end of the shaft 52 can reach to the apex of the root canal with the filler material cone/plug mounted thereto.

Additionally, root canals are not typically straight. Thus, the shaft 52 is made from a material (including, but not limited to platinum, silver, gold, copper, aluminum and alloys thereof or other thermally conductive and/or electrically conductive metals or alloys) that is sufficiently flexible to enable the shaft to navigate turns and curves in 3 dimensions in the root canal, while at the same time, to be sufficiently rigid to support the filler material 54 so that the practitioner can insert the filler material 54 into a prepared tooth root canal while grasping the delivery device connecting portion 50. Further, the shaft could be made from a composite which is coated with, platinum, silver, gold, copper, aluminum and alloys thereof or other thermally conductive and/or electrically conductive metals or alloys. In this manner, the device may be particularly beneficial for non-dental applications with tortuous pathways. The connecting portion 50 can be made in many configurations. For instance, the connecting portion 50 could be hollow, to define a path through which a plugger can extend. Ultimately, the configuration of the connecting portion 50 will allow for proper completion of circuitry discussed herein, a good connection for heat transfer, and for securing the delivery device 16 to the holder for withdrawal from the root canal.

Figure 5:
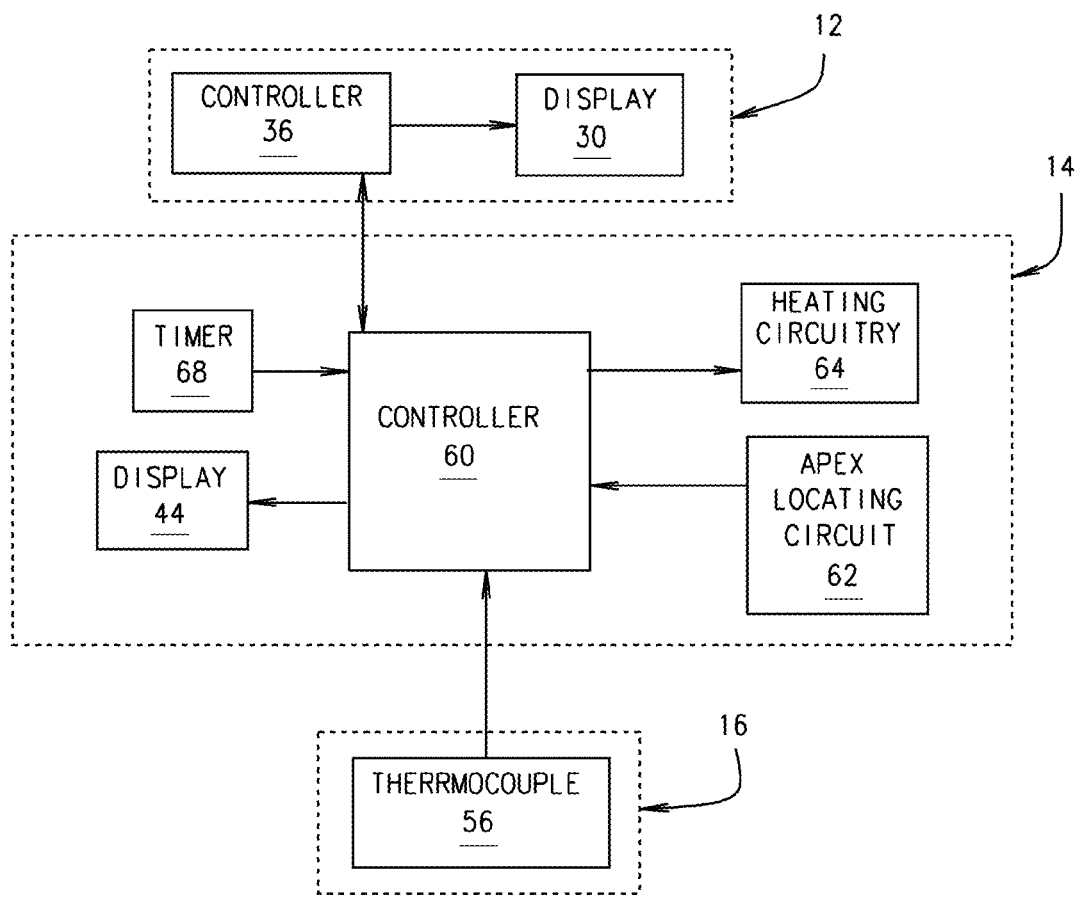
FIG. 5 is a block diagram of the control system of the obturation system.
Figure 7D:
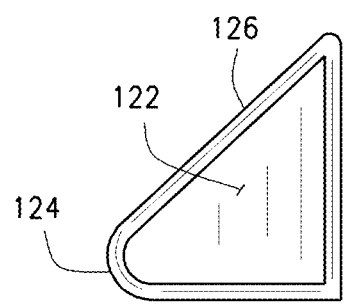
Figure 7E:
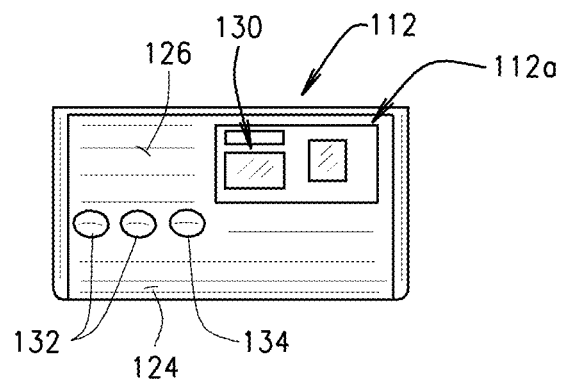
Figure 8A:
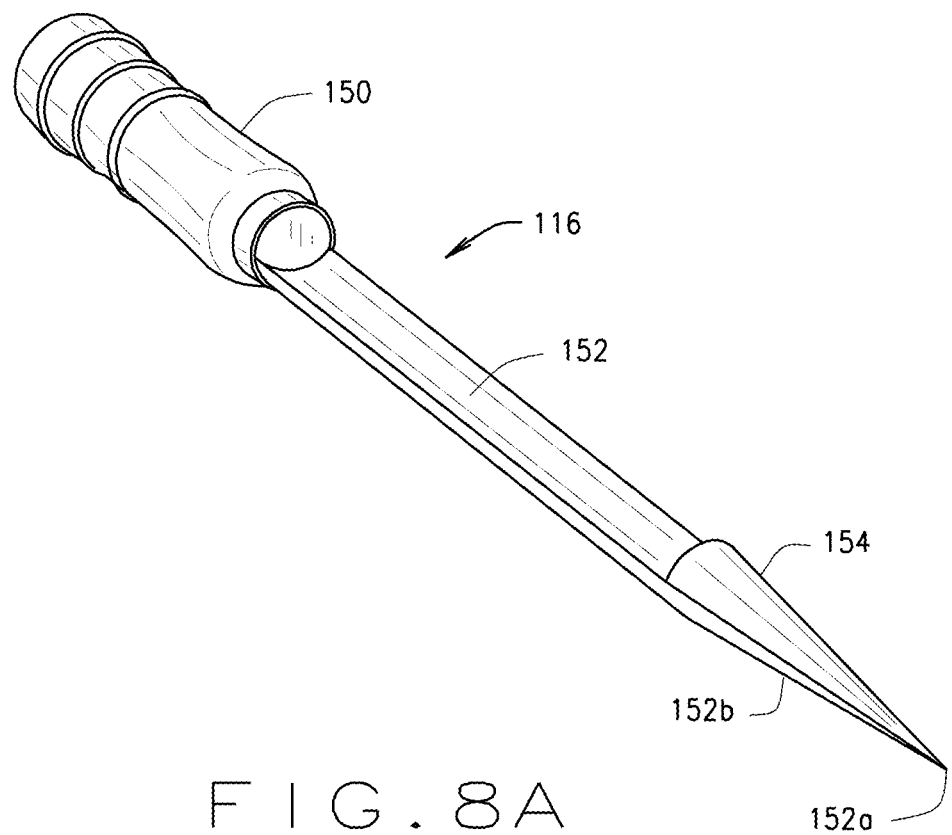

A schematic for the obturating system according to one embodiment is shown in FIG. 5. As seen therein, the system includes a main controller 60, an apex locating circuit 62 and a heating circuit 64, all of which are in the holder 14. The apex locating circuit 62 includes the delivery device 16, the lip clip 48, and a resistance/impedance monitoring circuit 66 (FIG. 6A). At least the outer or exposed surface of the bed portion 52a (which will contact the wall of the root canal when inserted into a prepared root canal) is made from, or is coated with, an electrically conductive metal or alloy. For example, the surface of the bed portion 52a (and of the shaft 52 has a hole) can be made from, or coated with, a NiChrome alloy, or silver or a silver alloy. The shaft 52 of the delivery device 16 is placed in electrical communication with the resistance monitoring circuit 66 by way of the connecting portion 50 of the delivery device 16 through the fingers 42b of the holder arms 44. As noted above, the shaft bed portion 52b extends the full length of the filler material cone/plug 54 and is positioned along the side of the filler material cone/plug 54. When the shaft 52 with the filler material cone/plug 54 is inserted in a prepared root canal, the shaft 52 will contact the surface of the root canal. As is known, the resistance of the apex locating circuit 62 varies as the end of the shaft approaches the end of the root canal (e.g., as the shaft 52, and hence the filler cone/plug 54, are inserted further into the root canal). Stated differently, the position of the end of the shaft 52, and therefore the filler plug 54 in a root canal can be determined by the measured or determined resistance/impedance of the apex locating circuit 62.

As noted above, the shaft 52 may be placed in electrical communication with the resistance monitoring circuit 66 of the apex locating circuit 62 by way of the delivery device connecting portion 50 and the holder arms 42. The holder arms 42 (or the surfaces thereof) can themselves be conductive, or an electrical conduit can extend along or through the arms 42a to the fingers 42b. The electrical conduit can be defined by a wire which extends along (or through) the arms 42a to the fingers 42b or by a printed trace which extends along (or through) the arms 42a to the fingers 42b. At least the inner surface 42c of the fingers 42b are electrically conductive.

The connecting portion 50 of the delivery device 16 can be made of a metal or metal alloy, or other material. Alternatively, the connecting portion 50 can define an electrical path which extends from the surface of the connecting portion 50 to the shaft 52. Thus, when the practitioner holds a delivery device 16 between the fingers 42b of the holder 14, as shown in FIG. 4, the shaft 52 will be placed in electrical communication with the resistance monitoring circuit 66 of the apex locating circuit 62. The resistance monitoring circuit produces a signal, indicative of the depth or location of the end of the shaft 52 (e.g., location information), based on the varying resistance of the apex locating circuit 62 as the shaft 52 of the delivery device 16 is inserted into the canal. Hence, the signal from the resistance monitoring circuit 66 is indicative of the location of the apex or end of the filler cone/plug 54 relative to the working end or apical foramen of the prepared root canal. This signal is received by the main controller 60 in the holder 14 and transmitted to the controller 36 in the base 12. This signal can be transmitted either wirelessly or through a wire which extends between the holder 14 and the base unit 12. Alternatively, the signal can be sent directly to the controller 36 of the base 12 (in which case, the holder would not have a controller). The controller 36 in the base unit 12 then drives the display 30 to illustratively show the practitioner on the scale 34 of the display 30 where in the root canal the end of the shaft and the apex or end of the filler cone/plug are located, as the delivery device is inserted into the canal. As can be appreciated, the system 10 informs the practitioner of the location of the plug in the root canal.

In one embodiment, the scale 34 is comprised of a plurality of segments of varying colors. Illustratively, the colors can vary from red to yellow to green. In one illustrative embodiment, the segments at the bottom of the scale 34 are green, and in particular, the bottom segment 34a is of a different green than the segment or two immediately above the bottom segment 34a. When this bottom segment 34a is lit, the practitioner will know that the bottom of the shaft 52 and the apex of the cone/plug 54 are at the apex of the root canal, or just shy of the apex of the root canal (e.g., within about ½ mm-¼ mm from the apex of the root canal). The practitioner can then compare this reading with the tactile fit of the filler material. When the bottom segment 34a of the scale 34 is lit, as will be discussed more fully below, it is safe to operate the heating circuit 64 to seal the apex of the root canal. Although a graph or bar chart 34 is used in the display 30 to inform the practitioner of the location of the end of the shaft 52 in the root canal, the display 34 could take on many other forms. The display could, for example, be a needle graph (such as a typical speedometer). Alternatively, the display could simply be a numeric display, which shows depth in millimeters, for example. In addition, the system can provide an audible signal when the end of the shaft 52 is at the apex of the root canal. Further, audible signals can be provided when the shaft 52 extends too far (e.g., is in danger of extending through, or does extend through, the apical foramen of the root canal) and/or is still shy of the root canal apex. If audible signals are provided, the sound indicating that the filler material is in an acceptable location will be different from the sound indicating that the delivery device has been extended through the apical foramen of the root canal. Such audible signals can be provided by a speaker (or other sound generator) provided on either the holder 14 or the base unit 12. Alternatively, or in addition, the holder can provide a tactile feedback (in the form of vibrations) to inform the practitioner when the distal end of the shaft (and hence the filler material) is properly positioned in the root canal or if the shaft has extended through the apical foramen into tissue surrounding the tooth root. As with the audible signals, the tactile signal for an acceptable (or "go") position in the canal will be different from the tactile signal for a "no-go" position in the canal. If a sound generator is provided, it would be activated by either the base unit controller 36 or the holder controller 60, depending on where the sound generator is located. The tactile feedback would be activated by the holder controller 60.

The heating circuit 64 (FIG. 6B), according to one embodiment, includes a heating device or element (not shown in the drawings) and the switch 46. The heating device is activated by pressing on the switch 46. The activation of the heating device can be automatically controlled by the main controller 60 in response to the signal from the apex locating circuit 62. Accordingly, if the controller 60 determines that the end of the shaft 52 is not at the apex of the root canal (e.g., is either still shy of an appropriate distance from the end of the root canal or has is extended through the apical foramen of the root canal), the controller 60 will not allow the heating circuit to be activated. Thus, the controller 60 will allow the heating circuit to be activated (or will activate the heating circuit) only when the end of the shaft 52 is within a predetermined range at the apex of the root canal. If the delivery device is determined to extend beyond or through the apical foramen of the root canal, the controller 60 can activate a visual and/or audible warning device informing the practitioner of that fact. In this more automatic system, wherein the controller activates the heating circuit, the switch 46 would be an activation switch for the control system.

In one embodiment, the heating device can be located in the handpiece body 40, in which case, the heat is conducted through the arms 42 to the delivery device connecting portion 50 and then to the shaft 52 of the delivery device 16. Alternatively, the heating device can be located in the fingers or grips 42b or the holder arms 42. As another alternative, the heating device can be located in the connecting portion of the delivery device. Finally, the heating device can be located in bed portion of the delivery device, in which case, the heating device will be adjacent the filler material. The heating device can be of several different types, depending on where it is located. If the heating device is located in the body of the handpiece or in the delivery device connecting portion, the heating device can be, for example, an inductive heater which utilizes an electrical coil, a piezoelectric heating device, a magnetic heating device, or a resistance wire. If the heating device is located in the grips 42b of the holder arms, or the shaft of the delivery device, the heating device is preferably a resistance wire or circuit that could extend down the delivery device. It will be appreciated that the heating device can be any heating device and it could be positioned at various levels of the delivery system. Therefore, the location and the type of heating device are not limited by the list just set forth.

In one embodiment, the filler material 54 is heated along its entire length (or along substantially its entire length) and is heated from its side (and is thus heated transversely). This allows for heat to be applied directly to the filler material substantially along the length of the filler material, as opposed to a method of attempting to heat the filler material longitudinally from the top (or coronal-most end) of the filler material. Because the filler material 54 is being heated from its side, and along substantially the entire length of the filler material 54, the high temperatures used by current devices are not necessary for the filler material to be heated to the point where substantially the entire plug of filler material becomes moldable. Further, the filler material is relatively small in diameter in one embodiment. Although gutta-percha (the most commonly used filler material in obturation) is a poor conductor of heat, with the short distance the heat must travel (at its widest, in one embodiment, the filler material is about 0.4 mm to about 2 mm in diameter at its upper end and about 0.1 mm-0.5 mm at its apex), the heat will be conducted through the gutta-percha relatively quickly, and the entire gutta-percha cone/plug will be substantially at a uniform temperature. That is, in several embodiments, the filler material is heated to a substantially uniform temperature, such that there will be no substantial temperature gradients, either from side-to-side or from top-to-bottom in the filler material (e.g., the gutta-percha cone/plug) 54. In some embodiments, the vertical and/or horizontal temperature gradient will vary by up to about 5° C., up to 10° C., up to 15° C., up to 20° C., and up to 25° C., etc. For example, the top part of the filler material in one embodiment will be about 50° C.-60° C., the apical most part may be about 40° C.-45° C. The consistency of temperature is advantageous in several embodiments because it facilitates more even and consistent heating and molding. Further, tighter temperature ranges from the proximal to the distal ends of the filler material permit a lower temperature to be delivered, which increases safety and may allow for enhanced precision.

Gutta-percha has been shown to be moldable at temperatures as low as 39° C.-40° C. (about 102° F.-104° F.), and changes from its β phase to its α phase around 42° C.-49° C., depending on the filler materials used in the particular gutta-percha formulation. In several embodiments, the heating circuit will heat the filler material (e.g., gutta-percha cone/plug) to between about 37° C. and about 65° C., (e.g., about 42° C.-50° C. in one embodiment, and between around 42° C.-46° C. in another embodiment). Thus, the filler material is heated to a temperature that is not greater than about 26° C. above a molding temperature for the filler material (i.e., 65° C.-39° C.). When gutta-percha formulations and manufacture processes are controlled, the temperature mediated phase transitions should be in a known range. The ability of this system, in several embodiments, to directly delivery heat will allow for a better control of temperature delivery. This will allow for the system to be programmed in a way to attempt to avoid the temperature mediated phase transitions and hence avoid complication related to shrinkage According to some embodiments, the temperature sensor 56, which is located on the bed portion 52b of the delivery device 16, is placed in communication with the controller 60 via the electrical conductivity of the shaft 52 and connecting portion 50, as noted above; and the signals from the temperature sensor 56 are received by the main controller 60 in the holder 14. The controller 60 will control the holder display 44 to display the temperature of the filler material. This information can be relayed to the base unit controller 36 to show the temperature on the base display 30. In one variation, the holder can be made without a display, and the temperature of the filler would be displayed on the base unit display 30.

In some embodiments, an optional holder is provided. In one embodiment, the holder controller 60 will control the heating circuit 64 and its associated heating element in response to signal received from the temperature sensor 56 to heat the filler material to the desired temperature. The system can be provided with a timer 68. The timer can be activated either when the heating circuit is activated, or when the controller determines the filler material is at the desired temperature. For example, if the filler material is gutta-percha, it need only be heated for not more than about 10 seconds, and preferably about 2-5 seconds. After the desired temperature has been achieved for a programmed time period, the controller will deactivate the heating circuit. During the heating cycle, the controller will control the heating circuit based on the continuing signals received from the temperature sensor so that the temperature of the filler material will be accurately and precisely controlled. The controller can also give an audible and/or visible and/or tactile indication that the heating cycle is over. Thus, the filler material will be precisely heated to a desired temperature and for a desired period of time. When the practitioner receives the signal that the temperature parameters have been reached he/she can manually remove the delivery device (or the delivery device can be automatically withdrawn, as discussed in an alternative embodiment below). The end of the heating cycle will occur once the shaft 52 has been removed from the canal, leaving the filler material in the canal. Because the shaft 52 of the delivery device 16, and particularly the distal end 52b of the shaft, are along the side of the filler material and adjacent the canal wall, a plugger can be used to not only ensure that the position of the filler material is not adversely affected as the shaft 52 is removed but also to allow for simultaneous molding as the filler material is being heated. When the shaft is removed, the source of heat will also be removed.

During an endodontic procedure, use of the obturation system 10 begins after a canal has been shaped, cleaned/disinfected and dried. To use the system 10 according to one embodiment, the practitioner will select a delivery device 16 and grasp it with his/her fingers or an instrument, such as with pliers or forceps or the holder 14. Again, as can be appreciated, because canals are of different tapers and diameters, the delivery device 16 will be selected such that the filler material 54 corresponds with the final files used to shape the canal. The practitioner will insert the selected delivery device 16 with the filler material 54 into the canal, and trim and fit the filler material 54, as is generally done currently, so that the filler material 54 will have a good fit in the apical portion of the root canal. However, unique to this system in several embodiments, the practitioner will be able utilize apex locator technology to compare this tactile feeling to the position of the filler material as determined by the system 10. In this case, the practitioner compares the reading of the apex locator to the sensation perceived when the practitioner fits the delivery device. From the feeling of a "tug back" while fitting the filler material 54 in the canal at the determined canal length (e.g., pulling back from the cone's most downward position), the practitioner can be fairly certain that the filler material (e.g., cone/plug) has a good apical fit. In one embodiment, if the temperature sensor is provided on the delivery device 16, the temperature sensor can be positioned proximal to the apex of the filler material (e.g., about 3 mm from the apex). This allows the practitioner to trim up to about 3 mm from the end of the filler material and without affecting the temperature sensor. Although the temperature sensor is disclosed as being 3 mm from the apex of the filler material 54, the distance of the temperature sensor from the apex of the filler material 54 can be varied. In several embodiments, the temperature sensor 56 can be spaced from the apex/end of the filler material 54 a distance sufficient to allow a practitioner to trim the filler material without cutting the temperature sensor from the delivery device 16. In one embodiment, to facilitate precise heating of the filler material 54, the position of the temperature sensor relative to the filler material can be accounted for in the controller for the heating circuit.

When the filler material 54 has been trimmed and fitted, the practitioner will withdraw the delivery device 16 with the filler material 54 from the root canal, apply a sealer to the filler material 54 and reinsert the delivery device 16 into the root canal. The practitioner will then grasp the delivery device at the delivery device connector portion 50 with the holder arms 42, as shown in FIG. 4. Alternatively, the practitioner can grasp the delivery device 16 with the holder 14, and use the holder 14 to insert the delivery device into the root canal. In one embodiment, the practitioner grasps the delivery device with the holder (similar to pliers), and then holds the delivery device (similar to a dagger) with the holder to insert the delivery device into the canal. When the arms 42 grasp the delivery device connector portion 50, the delivery device becomes part of the apex locating circuit, and the controller can confirm that the apex of the filler material (e.g., cone/plug) is in the correct position, e.g., within about ¼ mm-½ mm of the apical foramen of the root canal. The position of the apex of the filler material will be displayed on the display 30. If it is determined that the apex of the filler material is in the proper position in the root canal, the holder controller 60 will allow the heating circuit to be activated. The practitioner activates the heating circuit by pressing the switch 46. If the practitioner presses the switch 46 when the delivery device is not in an acceptable position in the root canal, as determined by the controller based upon feedback from the apex locating circuit, the controller will not activate the heating circuit 64. Although the switch 46 is disclosed to be on the arms 42 of the holder 14, the switch could be located elsewhere on the holder, or even on the base unit 12.

Activation of the heating circuit will directly deliver heat to the filler material 54 along the length of the filler material, as described above. The holder controller 60 will monitor the temperature of the filler material (in this example, gutta-percha) by means of the signals from the temperature sensor. When the controller 60 determines that the gutta-percha has reached a desired temperature, the controller will start the timer 68, and based on the output from the temperature sensor, will maintain the gutta-percha at the set temperature for a predetermined period of time (about 2-10 seconds), as noted above. When the heating period has ended, the controller 60 will prompt the practitioner to remove the shaft 52 of the delivery device and will deactivate the heating circuit. This prompt can be in the form of an audible and/or visible and/or tactile prompt.

In several embodiments, the shaft 52 extends along the side of the filler material (e.g., cone/plug) 54, rather than through the center of the filler material. The shaft 52 thus will not be in the way of placing a plugger in the root canal while the shaft is in the canal. In one embodiment, the plugger can be placed in the canal during heating (e.g., before the heating cycle is initiated). The system can include either a visual or audible indicator to let the practitioner know that the filler material is at its molding temperature, and that the practitioner can thus begin molding of the filler material by pressing on the filler material with the plugger. This will allow for molding of the gutta-percha (in this example) in the canal during heating. Additionally, by pressing on the filler material 54 while the bed 52b is being removed from the heated gutta-percha and the canal the possibility that the position of the filler material left in the canal will be adversely affected during removal of the shaft 52 from the canal is reduced. Due to the mechanical properties of the gutta-percha at its molding temperature, the gutta-percha will not adhere too tightly to the shaft bed portion 52b, and the shaft 52 can be separated from the gutta-percha fairly easily without materially affecting the position of the gutta-percha in the root canal. To facilitate the removal of the shaft 52 from the canal, the shaft can be provided with a release agent which is activated at the temperature to which the filler material 54 is heated. The release agent can be a material which has adhesive properties when cool (to help secure the filler material 54 to the shaft bed portion 52b) and which loses its adhesive properties upon heating to allow for the shaft 52 to be slipped from the filler material 54.

In some embodiments, the filler material 54 is about 8-10 mm in length and shaped as a cone. Other dimensions and shapes may also be used for dental and non-dental applications (e.g., cylindrical, triangular, rectangular, etc.). In one embodiment, once the filler material 54 is trimmed to fit into the canal, the filler material will be about 5-10 mm in length. When the heated filler material 54 is pressed using the plugger, the filler material will be molded to three-dimensionally fill the apical end of the root canal in an attempt to seal most, if not all aspects of the apical end of the root canal. In one embodiment, the 5-10 mm long filler material will thus seal and fill approximately 3-8 mm of the apical end of the root canal.

Further, because the gutta-percha is not heated substantially above 65° C. in several embodiments, the gutta-percha filler material will not be heated substantially above its higher temperature mediated amorphous phase change melting temperature. The high temperatures used by currently available heating devices can lead to shrinkage as the gutta-percha cools. Further, depending on the type of gutta-percha used and the temperature parameters programmed within this system, the gutta-percha can be heated for molding, yet heated below its lower beta to alpha phase transition temperature (about 42° C.-49° C.). This would not only allow for decreased chances of potential shrinkage, it has been shown that this can result in an overall expansion of gutta-percha by about 1%. Although a very small amount, this would be advantageous for densely sealing the canal in three-dimensions. Moreover, this controlled, direct delivery of lower heat as compared to other systems which heat the gutta-percha substantially above these temperature mediated phase transition temperatures is very advantageous. Stated differently, the shrinkage that occurs with the high heat systems will be reduced or even avoided according to several embodiments of the invention.

The obturation system 10, when used according to several embodiments described herein, will densely and three-dimensionally seal at least the bottom ⅓ of a prepared root canal. The proper sealing of the apex is vital to a successful endodontic procedure. This method allows for a better seal of the apex of the root canal, by not introducing high heat into the root canal, as is required using currently available heating instruments. As noted above, the gutta-percha cone/plug is heated along, or substantially along, it's full length (e.g., to the apex of the filler material), to allow substantially the full extent of the filler material (e.g., gutta-percha cone/plug) to be heated, and heated generally evenly. Thus, several embodiments of the invention provide for smaller temperature ranges along the filler material. In one embodiment, this more even heating of the filler material, along with the fact that the filler material is not heated substantially above its phase change temperature, will allow for a better and tighter seal of the apical end of the root canal. Once the root canal is sealed, the remainder of the canal can be filled with gutta-percha or other filler material in a conventional manner. That is, the remainder of the root canal can be filled via a hot vertical, cold vertical, or cold lateral method. Alternatively, the remainder of the root canal can be filled using heated filler which is extruded into the canal (e.g., like hot glue). Additionally, although not shown, the system disclosed herein could also employ an extrusion component to allow for the delivery of additional filler material at the time of or directly after the apical plug 54 has been activated (heated), and the shaft 52 has been withdrawn.

In a variation of the system 10, the switch 46 can be eliminated. In this variation, when the controller determines that the apex or distal end of the filler material is in the proper position in the root canal, the controller 60 will automatically start the heating cycle. Such a system could, however, include an activation switch (such as an on/off switch) to activate the system. In addition, the system can include the timer, and the controller can then automatically stop the heating cycle when the filler material has been heated to its desired temperature for a predetermined period of time (e.g., 2-10 seconds) and the shaft has been removed.

An alternative embodiment of the obturation system 110 is shown in FIGS. 7A-E The obturation system 110 includes a base unit 112, a holder 114, a filler material delivery device 116, a plugger 117, and a lip clip 148. In the obturation system 110, the holder 114 removably receives the delivery device 116 (albeit in a different manner than the holder 14 receives the delivery device 16), and the holder 114, the plugger 117 and the lip clip 148 are all connected to the base unit 112 by way of electrical cables 170, 171 and 172. In the obturation system 110, the components for the control system 180 (FIG. 30) are contained largely in the base unit 112, and the cables 170-172 place the holder (and hence the delivery device 116), the plugger, and the lip clip 148 in electrical communication with the control system 180. The communication between and among the components of the system 110 allows for precise controlling of the heating of the filler material delivered to the apical end of the root canal.

In several embodiments, the base unit 112 (shown generally in FIGS. 7A-E) includes a body housing 112a having a top surface 126, side surfaces 122, front surface 124, a back surface and a bottom. The base unit 112 is shown to be generally triangular in side elevation with the front surface 124 forming a curved connection between the top surface 126 and the bottom. The base unit 112 can have any desired shape or configuration. Externally, the base unit includes a display 130, control buttons 132 and a power or activation button 134. The cord 170 extends from one side 122 of the base unit 112 to electrically connect the holder 114 to the base unit and to place the holder 114 in communication with the base unit. In addition, second and third cords 171 and 172 (only cord 172 is shown) extend from the base unit to electrically connect the lip clip 148 and plugger 117 to the base unit 112. The cords 170-172 place the holder, the plugger and the lip clip in electrical communication with the controller in the base unit 112. If either the holder 114 or plugger 117 communicates with the base unit wirelessly, then their respective cords can be omitted. If the plugger 117 is not provided with a temperature sensor (in which case the temperature sensor would be located on the delivery device 116), then plugger need not be placed in communication with the base unit 112, and its cord can be omitted. The lip clip 148 and delivery device 114 are both part of the apex locating circuit 186. The lip clip could be connected directly to the holder 114, in which case, the holder could communicate wirelessly with the base unit. However, if the lip clip is directly connected to the base unit, there will need to be a corded connection between the holder 114 and the base unit 112, so that the apex locating circuit will be complete.

In one embodiment, the display 130, like the display 30, includes a portion that displays the temperature of the filler material (e.g., cone/plug) and an image of a root canal to graphically display where in the canal the delivery device, and hence the filler material, is located. The control buttons 132 can be used to adjust the set temperature (e.g., the temperature to which the filler material is programmed to be directly heated). The control buttons 132 can also be used to adjust the duration of the heating cycle.

One example of the delivery device 116 is shown in FIGS. 8A-9D. The delivery device 116, like the delivery device 16, includes a cylindrical body, grip or connecting portion 150 which is sized to be grasped by a practitioner. Again, this connecting portion 150 can take on any configuration. Ultimately the configuration of the connecting portion 150 will allow for proper completion of circuitry discussed herein, and securing the delivery device for withdrawal from the canal. In addition, this connection may be used for heat transfer, and in this case the configuration of the connecting portion 150 would allow for a good connection for heat transfer. In this embodiment, the shaft 152 is in the form of a strip of heat conductive material, which is shown to be curved or arced along its length. This strip of material will be sufficiently thin and flexible so that the shaft will be able to navigate curves in the root canal to reach to the apical end of the root canal, yet be sufficiently rigid to drive the filler material to the apical end of the root canal. In this embodiment, because the shaft 152 is in the form of a curved or arced strip, the shaft 152 will effectively blanket or wrap around a portion of the side surface of the filler material 154, as best seen in FIG. 9A. This will allow the heat that is transmitted to (or generated on or in) the shaft bed portion 152b to be applied to a greater surface area of the filler material 154. This will lead to more even heating of the filler material. In addition, the thin strip of the shaft material will occupy a small amount of space which will need to be filled in with molded/packed filler material upon removal of the shaft from the root canal. As best seen in FIGS. 9A and 9B, the shaft bed 152b to which the filler material 154 is mounted is curved and tapered, with the curvature and taper generally matching the curvature and taper of the filler material, as seen in FIGS. 8B and 9A. The filler material 154 can be adhered (e.g., molded) to the bed portion 152b of the shaft 152 such that the outer surface of the shaft 152 is generally flush with the outer surface of the filler material 154, to provide a generally smooth transition between the filler material of the filler material and the shaft, as shown in FIG. 9A. Because the shaft 152 extends to the apex of the filler material 154, the bed portion 152b of the shaft which overlays the filler material 154 has diagonal edges which meet, such that the shaft 152 comes to a point at its distal end 152a (e.g., the end remote from the body 150).

In the delivery device 116, according to one embodiment, a temperature sensor 156 (FIG. 9D) can be secured to, or could even be embedded in, the shaft bed portion 152b. Leads 156a (FIG. 9A) for the temperature sensor 156 can extend along, or be embedded in, the shaft 152. Heat can be delivered to the filler material 154 through the shaft 152 in the same manner as discussed above with the shaft 52. That is, the heating device is located in the holder 114, in the delivery device grip 150 or in the shaft bed portion 152b. As with the delivery device 16, because the shaft bed portion 152b extends along, or substantially along, the full length of the filler material 154 in some embodiments, the heat transmitted by or through the shaft bed portion is delivered directly to the filler material 154 along the length of the filler material 154. If a heating element is positioned at the level of the filler material (e.g. if the heating element is located in or on the shaft bed portion 152b), the leads 157 for the heating element can extend along (or be embedded in) the shaft 152. As seen in FIG. 9C, the leads 156a and 157 for the temperature sensor 156 and the heating device, respectively, extend into the body or grip 150 of the delivery device 116. Additionally, the wires/leads for the temperature sensor 156 may serve the additional purpose(s) of delivering a heating current to the shaft and/or serving as the effective probe (the varying resistance of which is measured) by the apex locating circuitry to determine when the end of the shaft is at the apex of the root canal.

In one embodiment, to facilitate the apex locating function of the delivery device 116, the shaft 152, itself, can be electrically conductive (in which case the shaft itself will form the probe of the locating circuit, as with the shaft 52 of the delivery device 16). Alternatively, the varying resistance of the leads 156*a* for the temperature sensor 156 can be monitored to confirm that the apex of the filler material 154 is at the apical end of the canal. This would require that the leads be exposed along the outer surface of the shaft 152 so that the leads could contact the wall of the prepared root canal during use. If the temperature sensor leads 156*a* are used as part of the apex locating circuit, the controller system 180 would alternatively switch between monitoring the temperature output data of the temperature sensor 156 and monitoring the resistance of the leads 156*a*, so that the controller can then monitor both the temperature of the filler material and the location of the apex of the filler material 154 and the end of the material strip 152 and then control the heating circuit based on the information from the apex locating circuit and the temperature sensor. Alternatively, because the shaft 152 in strip form presents a larger surface area than the shaft 52, if the shaft 152 (or at least its outer surface) is not electrically conductive (and thus does not itself define the apex locating probe), an electrically conductive strip can be provided which extends along the outer surface of the shaft. Such a conductive strip can be in the form of a wire adhered to the outer surface of the shaft 152 or as a printed trace or track on the outer surface of the shaft 152. In this instance, this conductive strip will define the probe for the locating circuit.

Figure 10A:
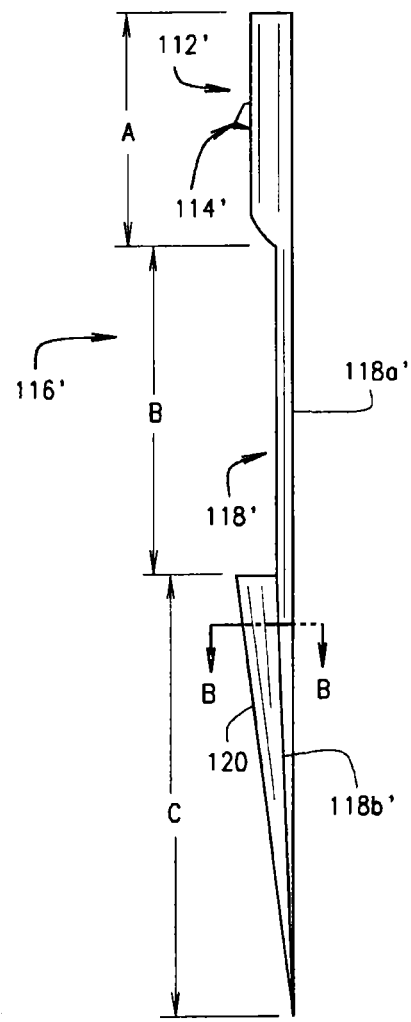
FIGS. 10A and B are side elevational and perspective views of an alternative delivery device for use with the system of FIG. 7A.
Figure 10B:
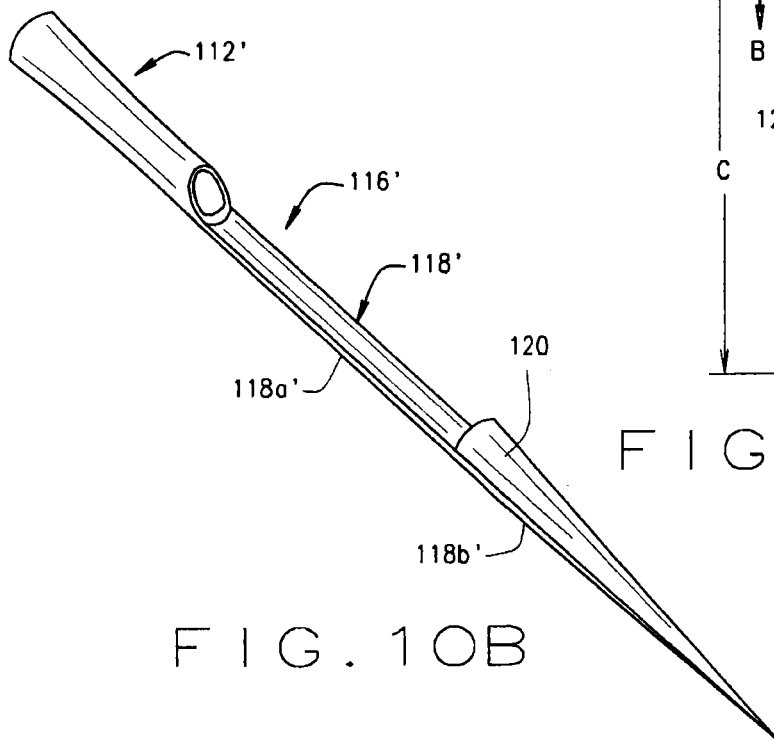

An alternate delivery device 116' is shown in generally in FIGS. 10A-B. The delivery device 116' includes an upper connecting portion 112' which contains a locking means 114' for removably connecting the delivery device 116' to a holder or heating chamber. This locking means (which is not shown in FIG. 10B) can include a spring biased member which engages a dimple in the holder or a pin which engages a bayonet slot (as shown in FIGS. 15-16). In the drawings, the spring biased member is shown on the delivery device, however, it could be contained in the holder. Similarly, the bayonet slot could be formed in the holder, and the delivery device connecting portion could be provided with a pin which engages the slot.

As seen in FIG. 10B, the connecting portion 112' can define a tube. The connecting portion 112' is shown to be generally cylindrical in FIG. 10A, and to be flared slightly at its top in FIG. 10B. The holder can be a currently available holder, such as System B (available from Sybron Dental Specialties, Inc. of Orange, Calif.), Touch-n-Heat™ (available from Sybron Dental Specialties), DownPack (available from Hu Friedy), Calamus Pack (available from Dentsply International), and Hot Tip (available from Discus Dental). Alternatively, the holder can be the holder 14 (FIGS. 2 and 4) or a holder such as is shown in FIGS. 16 and 17, and which is described below. Other holders described herein may also be used. The upper connecting portion 112' is illustratively shown to define an elongate cylinder which is open at both its opposite ends. However, this connecting portion can have other shapes and configurations if desired. A shaft portion 118' extends from the bottom of the connecting portion. The shaft portion 118' is shown to be arced, but could be formed to have other shapes. A bed portion 118*b*' is defined at the distal end of the shaft portion 118'. The portion 118*a*' of the shaft 118' between the bed portion 118*b*' and the connecting portion 112' defines a stem portion. The bed portion 118*b*' has an inner surface 119*a*, an outer surface 119*b*, and edges 119*c*. The inner surface 119*a*, as described below, is adapted to receive a plug of filler material 120 and to retain the filler material until the filler material is heated, at which point, the filler material will be released from the bed portion 118*b*' of the delivery device 116' to allow for 3-dimensional molding of the filler material to fill and seal at least the apical end of the root canal.

In some embodiments, the bed portion 118*b*' is generally triangular in elevation, as seen in FIG. 12, and thus the side edges 119*c* are inwardly sloping and define an apex 119*d* at the bottom of the bed portion 118*b*' (and the bottom of the delivery device 116'). Further, the bed portion 118*b*' may not be co-linear with the shaft portion 118*a*'. Rather, the bed portion 118*b*' may define a slight angle with respect to the shaft portion 118*a*', such that the apex 119*d* is generally coaxially aligned with the cylinder of the connecting portion 112', as seen in FIG. 10A. Stated differently, the outer surface 119*b* of the bed portion 118*b*' is tapered to correspond generally to the taper of the plug of filler material. The delivery device 116' can be formed in different sizes and with different tapers to accommodate differently sized root canals. The taper of the bed portion can correspond to the taper of the instrument/file used by the practitioner in preparing the canal. Preferably, the filler material 120 is mounted to the bed portion 118*b*' such that the bed portion and filler material, in combination, define a diameter and taper that corresponds to the diameter and taper of the finishing file used in preparation of the canal.

Figure 11:
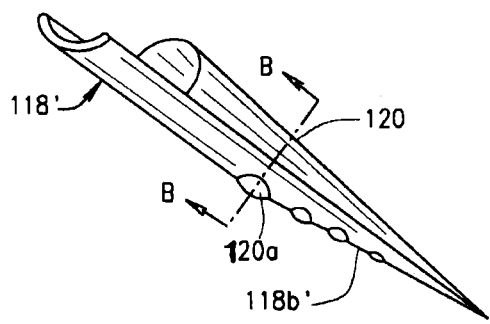
FIG. 11 is an enlarged perspective view of a bed portion of the delivery device of FIG. 10A.

As best seen in FIGS. 11 and 14A-B, the bed portion 118*b*' defines an arc in horizontal cross-section. The arc can be up to about 180° (e.g., being generally semi-circular in cross-section). The curvature or arc of the bed portion 118*b*' corresponds generally to the curvature or arc of the shaft portion 118*a*' and to the curvature or arc of the filler material 120. Hence, there is a generally smooth transition between the surface of the bed portion and the surface of the filler material, such that the filler material and bed portion generally define a circle in horizontal cross-section, as illustrated in FIG. 14B Further, the width of the bed portion 118*b*' between the inner surface 119*a* and outer surface 119*b* varies along the length of the bed portion. The bed portion 118*b*' is thickest at the top of the bed portion (proximate the shaft portion 118*a*'), where the bed portion can have a thickness of 0.1 mm, for example, and is thinnest at the apex 119*d* where the bed portion can have a thickness of 0.05 mm, for example. Additionally, the filler material 120 is positioned on the bed portion 118*b*', such that the apex of the filler material 120 is proximate the apex 119*d* of the bed portion 118*b*'. That is, the apex of the bed portion is at or within a few millimeters of the apex of the filler material.

In accordance with one aspect, the bed portion 118*b*' is provided with at least one retentive feature to enable the bed portion 118*b*' to help physically retain the filler material 120 on the bed portion until the filler material is activated (e.g., heated) in a root canal to be released or separated from the delivery device bed portion 118*b*' for molding of the filler material in the root canal. The retentive features can take several forms. The bed portion 118*b*' can be provided with just one of the retentive features or any combination of two or more of the retentive features. Upon heating of the filler material during obturation, the filler material softens and the delivery device 116' can be easily slipped from the plug 120 of filler material while the filler material remains in the canal for 3-dimensional molding. This molding process may be enhanced by a plugger, to allow for molding at the time of (i.e., during) heat delivery and to help retain the filler material in position during withdrawal of the delivery device 116' from the canal.

The retentive feature can include holes 122 which are formed in the bed portion. The holes 122 can be formed by punching them through the bed 118*b*'. In doing so, the flashing (not shown) formed by the punching process can be left in place or removed, as may be desired. If the flashing from the punching operation is left in place, the flashing will form a retentive feature. Further, a rim (not shown) can be formed around the hole. This rim can be a raised rim or an indented rim, and can completely or only partially surround the hole. The holes 122 are shown to be circular, but could be any desired shape. For example, the hole could be a slot, and the slot could be provided with a rim at one end of the slot. Additionally, the holes are shown to be of increasing diameter from the end or apex of the bed portion 118b' towards the upper end of the bed portion 118b', however; the holes 122 could be of constant diameter. Further, although the holes are shown to be generally aligned, the holes can be formed in any desired pattern.

The retentive feature can also be formed as cutouts or indents 124 in the side edges 119c of the bed portion 118b'. The cutouts or indents are shown to have a lower edge which is generally perpendicular to the side edge 119c of the bed portion 118b', an upper edge which slopes downwardly from the side edge 119c, and an inner edge which is generally parallel to an axis of the bed portion 118b'. Thus, the cutout/indent 124 defines a trapezoid with essentially three right angles. Of course, the cutouts 124 could be of any desired shape. For example, the cutouts 124 could be arced, v-shaped, rectangular, etc. In FIG. 11, the bed portion is shown with only the holes 122; and in FIG. 12, the bed portion is shown with both holes 122 and cutouts 124. As can be appreciated, the bed portion can be formed with only cutouts 124.

As another example, the retentive feature can include the bed surface 118b' being roughened. The bed inner surface 118b' can be roughened, for example, by etching or abrasive blasting to give the surface the texture of, for example, sandpaper. In addition, the surface texture could be accomplished through a plating process. Alternatively, the roughened surface can be defined by a pattern of lines, ridges, or shapes which are formed in the bed surface 118b'. The lines of the retentive feature can be formed, for example, in a crisscross pattern. Such a pattern can be stamped into the bed surface or plated on the bed surface.

As a further example, the retentive feature can include the side edges 119c of the bed 118b' being bent inwardly to form inwardly extending flanges 125 (FIG. 14B). The flanges can extend substantially the length of the bed, or be defined by discrete elements or fingers (e.g., have a plurality of cutouts).

Additionally, the retentive feature can include an adhesive which is applied to the bed and which will adhere to the filler material plug to the bed. The adhesive can be an adhesive that when heated will lose its adhesive properties which will enable the filler material plug 120 to separate from the bed portion 118b'.

In several embodiments, when the filler material 120 is applied to the delivery device bed 118b during manufacture or production of the delivery device 116', the filler material can be heated, molded and pressed/compacted against the bed inner surface 119a. Conditions such as heat, pressure and vacuum/suction will assist the filler material to engage the retentive feature(s) of the bed. Additional manufacture processes may allow for high levels of results in the application of the filler material 120 to the delivery device bed 118b'. This could include the use of such things as solvents to soften the filler material 120 for application to the delivery device bed 118b'. For example, the filler material can be dipped in a solvent (such as chloroform or orange solvent). The solvent softens the gutta percha filler material to allow it to be compressed against and molded to the delivery device bed. When the gutta percha filler material is adhered to the delivery device bed in this manner, the gutta percha adheres fairly well even without the retentive features. However, the use of the retentive features is preferred. Further, an adhesive may be used to enhance the connection of the filler material 120 to the delivery device bed 118b', particularly at the most terminal/distal end. Adhesive can be used as a retentive feature by itself, or in combination with any of the other retentive features. If the delivery device is provided with holes 122, the filler material will protrude through the holes 122 as the filler material is molded to the delivery device bed to form a small button 120a on the back side of the bed portion, as seen for example in FIGS. 11 and 14A. The button 120a can have a diameter greater than the diameter of the hole 122, so that the button 120a overlaps the back surface 119b of the bed 118b'. If the delivery device is provided with cutouts or indents 124, the filler material, when pressed on to the bed 118b', will overlap the back surface of the bed 118b' in a similar fashion. This overlapping will facilitate retention of the filler material plug 120 on the bed portion 118b' of the delivery device 116' during packaging and shipping, for its shelf life, and during positioning of the delivery device 116' (and filler material 120) in a prepared root canal. If the delivery device is provided with flanges 125, the filler material 120 will be molded around the flange, such that the flange extends into the filler material 120.

Although the delivery device 116' is provided with the filler material attached in some embodiments, an alternative embodiment may allow for the delivery device to be provided without the filler material 120 attached. In such an embodiment, the practitioner could apply a filler material to the delivery device. For example, in one embodiment, the delivery device is configured to receive a wide range of filler materials selected by a user. Separate coupling devices may be provided to facilitate the coupling of the delivery device and the filler material. Alternatively, the delivery device and/or the filler material may be comprised of coupling features to facilitate pairing. In this instance, the practitioner can adhere the filler material to the bed of the delivery device using adhesives and/or the retentive features noted above. In addition, the filler material can be softened prior to attachment to the delivery device by heating the filler material or exposing the filler material to solvents (i.e., by dipping the filler material in solvents or brushing solvent on the filler material).

As a variation on the method described above, when using a delivery device provided without the filler material, the practitioner can insert the delivery device into the prepared canal without the plug of filler material. The desired filler material plug can then be inserted into the canal. In this instance, the shape of the delivery device will act as a guide to facilitate insertion of the plug of filler material into the prepared root canal. When the filler material is inserted into the canal, the filler material will contact the delivery device at least along the bed of the delivery device, so that the delivery device can heat the filler material in situ in the canal, as described above.

In one embodiment of the delivery device, the connecting portion 112' can have a length A of about 10 mm, the stem portion 118a' can have a length B of about 18-20 mm, and the bed portion 118b' can have a length of about 8-10 mm. As discussed herein, the delivery device can be provided in different sizes, as are, for example, loose gutta-percha plugs. In this way the bed portions 118b' can be of different diameters and tapers. This will accommodate root canals of varying dimensions and tapers. In one embodiment, the taper of the bed portion will correspond to the taper of the file/instrument used to prepare the canal. Canals also vary in length. Thus, as discussed herein, the delivery device 116' may be provided with stem portions 118a' of various lengths to accommodate various tooth lengths. The delivery device 116' (less the filler plug 120) can be formed in any desired fashion. For example, the delivery device 116' can be formed by a stamping, molding, casting, machining, or grinding operation or any other desired manufacturing procedure. The filler plug 120 will be adhered to the delivery device after the delivery device 116' is formed. Again, delivery devices can be provided without the filler material attached.

An embodiment of the holder 114 is shown in FIGS. 17A-E. The holder 114 removably receives the connecting portion of the delivery device 116,116'. The holder 114 is generally cylindrical in end view (as seen in FIGS. 17B-C), and is generally pen-like in shape in side view (as seen in FIGS. 17A and D). Although shown to be generally straight, the holder 114 could define a bend or angle at its forward end, such that the holder is generally contra-angled. However, the holder 114 is relatively short, for example, being only about 50 mm (about 2") long. Hence, the holder 114 is only slightly longer than the overall length of the delivery device 116, 116'.

In some embodiments, the holder 114 includes a channel 160 which opens at the front of the holder and extends rearwardly from the front of the holder. The channel 160 is sized and shaped to receive the connecting portion of the delivery device 116, 116'. The channel 160 can be contained in an axially movable receptacle 160*a*. The receptacle 160*a* can completely surround the delivery device connecting portion. Alternatively, the receptacle can define an arc of greater than 180°, and the delivery device connecting portion will snap or click into the receptacle, or be connected to the receptacle by way of locking elements, as discussed above.

In some embodiments, the receptacle 160*a* can include contacts which make electrical connections with the contacts on the connecting portion 150 of the delivery device 116, such that the leads 156*a* and 157, and hence the heat sensor 156 and heating device (if the heating device is in the shaft bed portion 152*b*) will be placed in electrical communication with the controller. For both the delivery device 116 and 116', the receptacle electrically connects to the electrically conductive outer surface of the delivery device, to enable the delivery device to operate as the probe of the apex location circuit 186.

In several embodiments, the holder 114 can be provided with a retraction device 164 which is operatively connected to the receptacle 160*a* to move the receptacle axially along the channel 160 of the holder. The retraction device 164 is activated by a controller 166 in the holder. The controller 166 of the holder, in turn, is in communication with the main controller 182 in the base unit 112. The retraction device moves the receptacle 160*a* (and hence the delivery device 116, 116') axially rearwardly along the holder channel from an extended position to a retracted position. The extent of axial movement is at least enough to withdraw the delivery device bed portion from the filler material. This retraction process can be programmed to be part of the obturation process, in that when all parameters have been met, as discussed herein, the delivery device will be withdrawn from the filler material. The retraction device can be, for example, a spring, an electric motor, a solenoid, a piston or any other device that can move the receptacle 160*a* axially within the channel 160. After an obturation cycle is completed, the retracting device 164 can be operated to move the receptacle 160*a* back to its extended position for its next use. This return to the extended position can be automatic, or can happen upon the pressing of a reset button.

Figure 29:
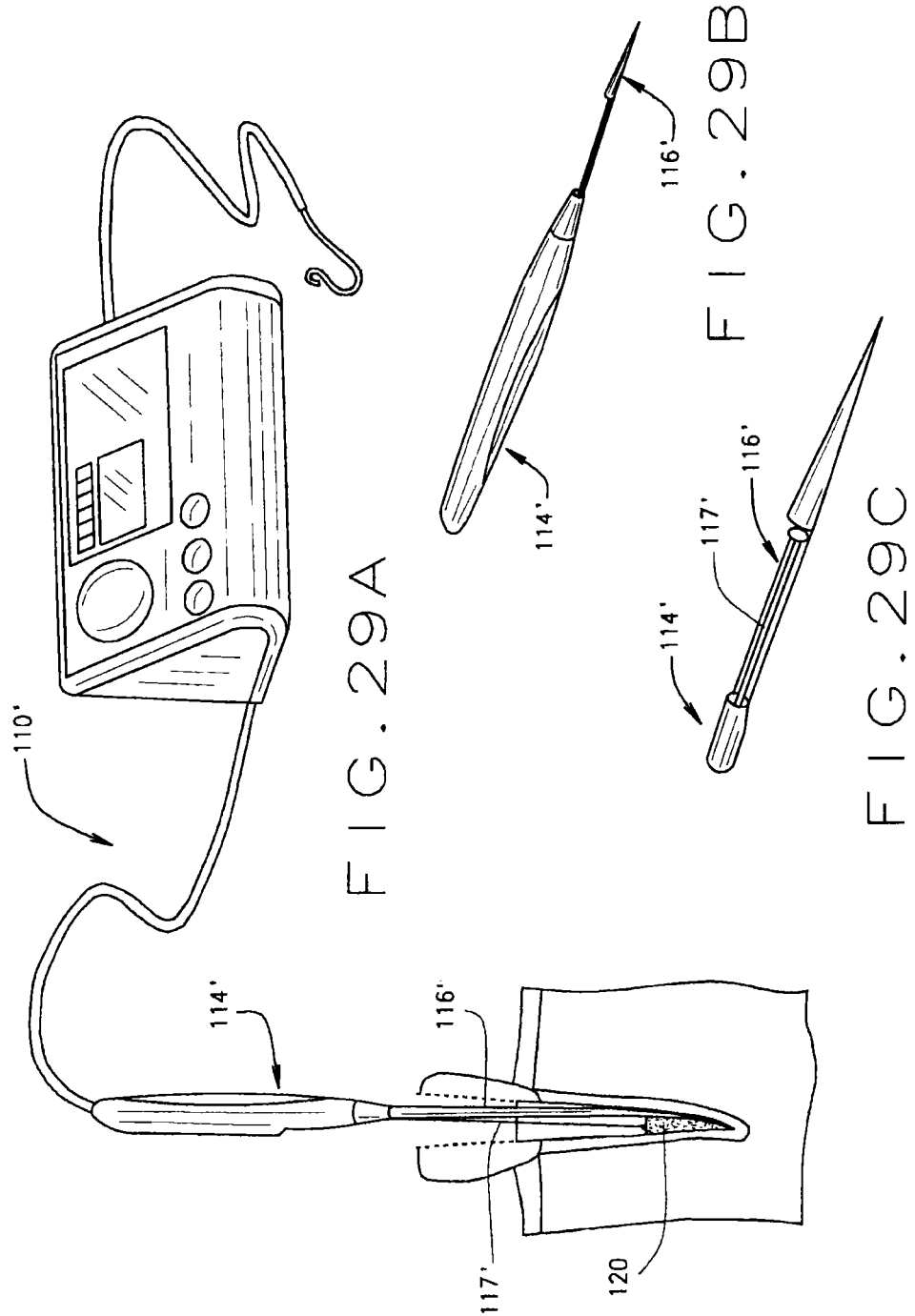
FIG. 29A is a schematic drawing of a further embodiment of the obturation system.
FIG. 29B is a perspective view of the holder and delivery device of the system of FIG. 29A.
FIG. 29C is an fragmentary, enlarged perspective view of the holder of FIG. 29B showing the tip of the holder with an automatic plugger extending from the holder toward the filler material on the delivery device.

In some embodiments, the delivery device 114' shown in FIG. 18 is substantially similar to the delivery device 114. However, the delivery device 114' incorporates a plunger 117'. The plunger 117' is preferably similar to the plunger 117 (described below) in that it will have a working surface which will vary in shape and size as the plunger 117' passes through the canal to mold the filler material. The plunger 117' is operatively connected to a plunger driver 167 which moves the plunger 117' axially. This is shown in FIGS. 29A-C. As shown therein, the system 110' does not include a separate plugger, as does the system of FIG. 7A. Rather, the plugger 117' is contained within the holder 114' and extends through the tube-shaped connecting portion of the delivery device 116' to engage the filler material 120 as shown in FIG. 29A. As with the retractor 164, the plunger driver 167 can be any mechanism which can axially move the plunger relative to the holder. Thus, for example, the plunger driver can be a spring, an electric motor, a solenoid, or a piston. The plunger 117' is sized and shaped to be able to move axially through the channel 160 and to extend along or through the hollow tube of the connecting portion 112' of the delivery device 116'. The plugger 117' is sufficiently long such that the distal end of the plugger can engage, and press against filler material 120. If the system 110 is provided with the holder 114', the full obturation cycle can be automated, and the controller can control the molding of the heated filler material using the plugger 117' and can control the extraction of the delivery device 116', as discussed herein. Hence, all the practitioner would need to do, in some embodiments, is properly position the delivery device 116' in the root canal and to activate the obturation cycle. The plugger may be disposable or reusable. In this embodiment, the plugger 117' can be provided with a pressure transducer. The pressure transducer will generate a signal indicative of the force being applied to the filler material. The pressure signal will be received by the controller, and the controller will control the plugger driver such that the force applied to the filler material does not exceed a determined about (such as about 7-10 lbs).

An alternative embodiment 114" of the holder is shown in FIG. 33D. The holder 114" is designed for use with the delivery device 116', and includes a nose 160' which is sized to be received in the tube defined by the connecting portion 112' of the delivery device 116'. The connection between the delivery device and the holder nose can be merely a frictional connection. This frictional connection can be enhanced, for example, by a rubber ring around the connection portion 112'. Alternatively, a mechanism, such as a lock, can be provided for a positive interlocking connection between the delivery device 116' and the holder nose 160'. The interlocking connection can be a connection such as discussed above in conjunction with the delivery device 116. That is, the interlocking connection can include a spring biased member on the delivery device which engages a dimple on the holder nose or a pin on the delivery device which engages a bayonet slot on the holder nose. The two portions of the connection can be reversed. That is, the spring biased member can be on the holder nose 160' and the dimple can be on the delivery device; similarly, the bayonet slot can be on the delivery device and the pin can be on the holder nose.

As discussed above, in several embodiments, the heating device can be located within the holder 114, 114', 114". With the connecting portion of the delivery device 116, 116' being received by the holder receptacle 160*a* of the holder 114', the heating device can include, for example, an induction coil that surrounds the chamber 160 to heat the delivery device connecting portion and hence the delivery device shaft. Alternatively, a piezo electric element or a rotational magnetic heating device can be provided which generates heat which is delivered to the delivery device. The heating circuit (which contains the heating device) is in communication with, and controlled, by the control board 166 in the holder 114 based upon commands from the main controller 182.

The plugger 117, according to some embodiments, is shown generally in FIGS. 19-22. This universal plugger 117 includes, in one embodiment, a handpiece or handle 212 having a shaft 214 extending from the handpiece/handle. The shaft 214 is shown in FIG. 19 to be contra-angled, and comprises a working end 216 which engages and molds the filler material. The working end 216 (shown in detail in FIGS. 21 and 22) comprises a stationary plate 218 which is spaced from the distal end 214a of the shaft 214 by means of a post 220. The post 220 extends from the center of the distal end 214a of the shaft 214 and is secured to the stationary plate 218 at the approximate center of the plate 218, as seen in FIG. 20. In an alternative embodiment, this central plate/post can simply be a post with a shaft and a "stationary plate" of the same diameter. That is, the stationary plate would be defined by the bottom surface of the post. During an obturation procedure, the post 220 will be subjected to compression forces. The post 220 is thus made from a material (such as a metal, metal alloy, or composite material) which will be able to withstand typical compression forces applied to it, such that the post 220 will not buckle during a procedure.

In some embodiments, a plurality of moveable plates 222 is provided which are moveable independently of each other relative to the post 220 and stationary plate 218. Illustratively, each moveable plate 222 is connected to the working end 216 of the shaft 214 by means of at least one connector 224. The connector 224 can be a wire, cable, filament or the like. The connectors 224 are made from a material which will allow the moveable plates 222 to move horizontally relative to the stationary plate 218 and the post 220. As illustrated, the movable plates 222 are shown to be behind the stationary plate 218. However, if the central plate is simply a post, then the moveable plates 222 would be positioned distal to the central post (not shown). The material from which the connectors 224 are made will facilitate inward movement upon relatively passive horizontal forces as well as return of the moveable plate 222 to their original (expanded) position once the horizontal deflecting force is removed. In addition, the connectors 224 can resist compressive forces, such that the distance between the moveable plates 222 and the working end 216 of the shaft will not be substantially changed when the wires 224 are subject to compressive forces. The connectors 224 can be made from a metal, metal alloy, composite or plastic material.

In one embodiment, each moveable plate 222 has its own connector 224, such that the moveable plates 222 are individually connected to the distal end 214a of the shaft 214. The plates 222 can be moved from an expanded or open position (shown in FIGS. 21-23) to a closed position shown in FIG. 25. However, because the plates are movable in two axes independently of each other, the overall configuration of the plates is not limited to a generally circular configuration. Stated differently, the moveable plates can move in two degrees of freedom; that is, each moveable plate can move along an x-axis and a y-axis relative to the stationary plate. The x-axis for each moveable plate would be defined by a line extending from the center of the stationary plate to bisect the moveable plate; and the y-axis is perpendicular to the x-axis.

As seen in FIG. 24, this freedom of movement allows the plates to attain an overall oval configuration, for example. The ability of each of the moveable plates to move in two axes and independently of each other enables the moveable plates 222 to define an infinite array of geometric shapes and of different sizes.

Illustratively, in one embodiment, the moveable plates 222 are shown be generally semicircular, having a curved outer edge and a straight inner edge. The stationary plate 218 is shown to be generally circular. In combination, the plates 218 and 222 define a plugger or working surface 226 (as seen in FIGS. 23-25), in which the moveable plates 222 overlap each other as well as the stationary plate 218. The movable plates 222 can be arranged such that one side of the each moveable plate overlies the moveable plate, for example to the right, and the other side of the moveable plate is overlaid by the moveable plate to the left. While this overlapping arrangement of the moveable plates provides for a small degree of slope to each moveable plate 222, the moveable plates 222 are generally parallel to each other and to the stationary plate 218. In use, the moveable plates 222 are pressed up against each other under an axial force as the plugger surface is pressed against filler material. The connectors 224 are sufficiently strong to resist this axial force, so that the moveable plates can still move passively in a generally horizontal plane relative to each other and the stationary plate 218 as the movable plates engage the wall of the root canal. Thus, the use of the moveable plates provides for the application of axial forces over an area that is substantially equal to the cross-sectional diameter of the canal. The axial force applied by the plugger against the filler material to mold the filler material may still allow a small amount of filler material to pass outside of the working or plugging surface and/or even between adjacent plates when the molding/packing forces are applied to the heated filler material. A small amount of filler material may escape axial/apical molding in this regard in some cases. However, more effective forces of three-dimensional molding will nonetheless be accomplished. Several embodiments of the invention are particularly advantageous because the working ends are not fixed and allow for the application of an axial force over an equivalent area. Hence, use of the plugger 117 will provide for improved obturation results.

The stationary and moveable plates 218 and 222 could be provided in other shapes, as desired. For example, the inner edge of the moveable plates 222 could be curved, rather than straight; the outer edge could be polygonal, sinusoidal, or any other desired shape. Alternatively, the moveable plates 222 could be petal or generally tear shaped. The central stationary plate or post could be polygonal, flower shaped (e.g., a stationary area with petals extending from the stationary area), or any other desired shape. Depending on the size and shape of the moveable plates, the stationary plate 218 and its attendant post 220 could be omitted.

A connector 224 is shown to be secured to each moveable plate 222 along an outer edge of the moveable plate. However, if desired, the connection point of the connector 224 to the moveable plate 222 can be altered to most any desired location on the moveable plate. For example, the connector 224 could be connected at the approximate center of the moveable plate 222 or the connector 224 could be connected to the moveable plate along its inner edge. The connector 224 is shown to be generally in the shape of an elongated or stretched "S". However, the configuration or shape of the connector 224 could be changed to be any desired shape. For example, the connector 224 could be straight, rather than generally S-shaped. In this instance, the connector 224 would define a slope. The degree of the slope would be defined by the connection point of the connector 224 to the plate 22. Alternatively, the connector could be ⌐-shaped or arced (e.g., curved with a generally constant radius).

The connector 224, like the post 218, will be subjected to compression forces during an obturation procedure. Hence, the connector 224 must be made from a material which will be sufficiently strong to resist the compression forces (e.g., avoid buckling under typical compaction pressures) yet allow for horizontal translation of the plates relative to each other and the stationary plate 218. That is, the connector will have a shape and length such that the movable plates 222 have a normal position in the open position (FIG. 23). During obturation, as will be described below, the position of the moveable plates 222 relative to each other and to the stationary plate 218 will change (for example, to the orientations shown in FIG. 24 or 25). When the plugger is withdrawn from the root canal, the connectors 224 will return the plates to the normal open position of FIG. 23. As will be apparent, the shape of the connector, as discussed above, may affect the ability of the wire to withstand the compression forces.

Typical loads applied by a practitioner to the plugger's working end can be in the range of 30,000 lbs/in$^2$, whereas the corresponding pressures read at the filler material—root interface upon typically warm gutta-percha compaction techniques are about 2,333 lbs/in$^2$. Said differently, forces generated during typical warm gutta-percha packing procedures are about 4.2 lbs. That is, practitioners have been shown to apply about 4.2 lbs. of load when molding/packing the filler material which, in turn causes about 2,333 lbs/in$^2$ of pressure to the root surface. This level of force has been shown to safe as a prepared root canal has been shown to be able to safely withstand 2500 lbs/in$^2$ However, if the load to the root canal wall exceeds the 2500 lbs/in$^2$ range, root fracturing becomes a concern. As stated above, lateral forces to root canal walls generated by currently available pluggers easily exceed this threshold if inadvertently locked into the canal. According to several embodiments of the invention, the plugger (e.g., plugger 117) will decrease this type of locking to the canal as discussed below; however, compaction of the filler material will still generate lateral forces on the root surface. The knowledge of these parameters can influence the tolerances of the materials used to construct the plugger 117. As an example, so that the post 220 and connectors 224 will not buckle under proper loads, the post 220 and connectors 224 can withstand loads of at least 4.2 lbs. In addition, the post 220 and connectors 224 could be allowed to buckle if the load applied to the plugger exceeds 4.2 lbs. Buckling of the post and connectors at loads in excess of 4.2 lbs would help prevent transmission of excess lateral forces to the root canal wall (through molding/packing of the filler material), in an effort to help prevent fracturing of the root canal wall.

Additionally, in several embodiments, the connection of the post 220 and the connectors 224 to the stationary plate 218 and the moveable plates 222, respectively, are able to withstand the forces to which they will be subject during an obturation procedure, thereby minimizing the risk of the stationary plate 218 or the moveable plates 222 separating from the post 220 or connectors 224, respectively. In addition, the individual plates can be retained in lateral orientation. To this end, as seen in FIG. 20, the distal end 214a of the shaft 214 is provided with circumferential, axially extending holes 228 which receive one end of the connectors 224. Hence, the connectors 224 are embedded in the distal end 214a of the shaft 214. Similarly, the post 220 is embedded at the distal end 214a of the shaft 214 in the approximate center of the shaft distal end 214a. Although not shown, the plates 218 and 222 can be provided with receptacles which receive the opposite ends of the post 220 or connectors 224.

In some embodiments, the connectors 224 position the moveable plates 222 so that the moveable plates 222 are vertically close in proximity to the stationary plate 218. The moveable plates 222 are shown to be slightly vertically above the stationary plate 218, however, they could be configured to be slightly vertically below the stationary plate 218. In operation, as noted above, the stationary plate 218 in combination with the individual moveable plates 222 define the plugger surface 226 which engages the filler material to mold/pack the filler material into the root canal to fill and seal the root canal. Further, as illustratively shown, the moveable plates 222 overlap each other, such that there are no axially visible gaps between the plates (e.g., such that the plates, in combination, define an uninterrupted surface in plan view, as seen in FIGS. 23-25). If desired, the moveable plates 222 can be positioned relative to each other and/or the stationary plate 118 such that horizontal gaps are formed between the plates, such as shown in the plugger surface 226' of FIG. 28. As noted above, despite the fact that some heated filler material may pass between adjacent plates as the plugger surface exerts axial forces on the heated filler material, because the plugger surface 226 has an area that approximates the cross-sectional area of the root canal at substantially all levels of the root canal during which the plugger surface is in contact with the filler material, use of the plugger 117 will provide better filling and sealing than currently available pluggers.

In an embodiment for sealing the apex of a root canal, the diameter of the distal end 214a of the shaft 214 has a diameter D of about 0.5 mm. The size and number of moveable plates 222 enables the plugger surface 226 to define an approximate circle in the open position (as in FIG. 23) that is about 1.0 mm in diameter, and to define a circle in the closed position (as in FIG. 25) of slightly greater than 0.5 mm. It is anticipated that the plugger will be provided in different sizes (e.g., small, medium and large), so that different pluggers can be used for different teeth or different purposes. For example, the illustrated plugger can be a small plugger which could be used to seal the apex of a root canal or to mold/pack filler material in a tooth with a narrow root canal. A medium plugger may have a shaft with a diameter of 0.8 mm and a large plugger could have a shaft with a diameter of 2.0 mm. The oval, shown in FIG. 24, can have a minor axis as small as the diameter of the stationary plate 218 (which has a diameter that can be less than the diameter D of the shaft distal end 214a), and a major axis that can exceed the illustrative 1.0 mm diameter of the generally circular plugger surface 226 of FIG. 23. As can be appreciated, the variation in size of the plugger surface 226 can attain will be dependent on the size and shape of the stationary plate 218 and the moveable plates 222. Additionally, the complexity of the circumference of the plugger surface 226 that can be attained will be determined by the number and shape of the moveable plates 222. In the illustrative figures, the plugger 117 includes five movable plates. This enables the plugger surface 226 to attain the generally circular or generally oval shapes shown in FIGS. 23-25. However, if additional moveable plates were provided, the plugger surface could attain move complex shapes. For example, the plugger surface could attain a generally hour-glass configuration. As noted above, the use of movable plates 222 which are movable relative to each other and to the stationary plate 218 allow the plugger surface 226 to achieve an infinite number of shapes to enable the plugger surface to generally approximate and generally conform to the cross-sectional size/shape of the root canal at virtually any level in the root canal. The complexity of the shapes that can be obtained and the ability for the plugger surface to approximate the cross-sectional shape of the root canal at a specific level in the root canal increases as the number of moveable plates increases and as the size of the moveable plates decrease. Although the moveable plates 222 are all shown to be generally the same size and shape, the moveable plates of a plugger could be provided in two or more shapes and sizes. This variation in size and shape of the moveable plates on a plugger may even further enhance the ability of the plugger surface to conform generally to the cross-sectional shape of the root canal.

In an obturation procedure, after the filler material (plug) has been fitted, sized and properly positioned in the root canal, the practitioner will insert the plugger 117 into the root canal to mold/pack the filler material plug. As the plugger 117 is inserted into the canal, the outer edge of the moveable plates 222 will engage the wall of the root canal, causing the moveable plates 222 to move relative to each other, such that the shape of the plugger surface 226 will be altered to conform generally to the cross-sectional shape of the root canal. The shape or configuration of the plugger surface 226 may be altered to define a smaller circle, or the configuration of the plugger surface 226 may be altered to be more oval than circular. In one embodiment, the moveable plates 226 provide for a plugger which defines a plugging surface 226 which will vary in shape throughout the length of the root canal such that the plugging surface 226 will approximate the cross-sectional shape and size of the canal at all levels of the root canal, such that substantially the full upper surface of the filler material plug will be covered by the plugger surface 226. In several embodiments, the plugger will be able to decrease in size as it moves down a tapered canal preparation. This will substantially reduce the amount of, or even prevent, the filler material from moving axially around the plugger 117 and toward the tooth crown, as occurs with currently available pluggers, as the plugger presses into and exerts an axial force on the filler material. In one embodiment, the filler material will not be forced toward the tooth crown as the plugger is urged into the warmed filler material. Stated differently, rather than being displaced upwardly, the warmed gutta-percha will be forced to move apically (toward the apex of the canal). By substantially preventing the filler material from moving toward the tooth crown, it will facilitate a better molding/packing of the filler material to thereby better mold the filler material to the full anatomy of the root canal. That is, the filler material will be better molded to fill lateral canals, fistulas, ledges, etc. of the root canal. This will ultimately create a better seal of the root canal.

In one embodiment, by enabling the shape of the plugger surface 226 to vary, and to vary instantaneously as the plugger passes through the canal to mold the filler material, the plugger 117 can adapt to the infinite number of potential cross-sectional shapes of the canal that may be present. While there may nonetheless be some gaps between the edge of the plugger surface 226 and the root canal wall, there will be greater surface area contact of the plugger surface 226 with the filler material than occurs with currently available fixed diameter pluggers. As can be appreciated, as the number of moveable plates 222 increases and the size of the plates decrease, the ability of the plugger surface 226 to more accurately conform to, or approximate, the cross-sectional shape of the root canal at any particular level in the root canal will improve. This will allow for greater molding/packing forces. Hence, the plugger 117 will facilitate a better filling of the root canal system with the filler material. Further, it is noted that because the moveable plates 222 are moved by contact with the root canal wall, the lateral forces applied by the plugger to the root canal wall will be minimal. Additionally, in one embodiment, by enabling the shape of the plugger surface 226 to vary automatically in response to the cross-sectional shape of the root canal wall, the practitioner may only need to use a single plugger for a complete obturation procedure. Stated differently, the practitioner will not need to use multiple fixed-diameter pluggers, as is currently required, to perform an obturation of a root canal.

In accordance with another aspect of the plugger 117, a button 230 (FIG. 19) can be provided on the plugger handle 212 proximate the forward end of the handle 212. The button 230 is operatively connected to moveable plates 222, such that when the button 230 is pressed, the moveable plates 222 will be drawn in to reduce the area or size of the plugger surface 226. This will allow for general maneuvering of the plugger within the root canal. For example, the plugger 117 can be provided with a loop that surrounds the connectors 224 proximate the distal end 214a of the shaft 214. This loop could reside in an annular channel at distal end of the shaft 214 and which surrounds the connectors 224. A control wire will extend through the shaft 214, to operatively connect the button to the loop. When the button is pressed, it will effectively pull the control wire to reduce the effective size of the loop. Reduction of the size of the loop will cause the loop to constrict around the connectors 224 within the shaft 214a, thereby pulling the moveable plates 222 inwardly to reduce the size of the plugger surface 226. In another embodiment, a distal chamber (not shown) can be formed at the working end 214a of the shaft 214. This chamber would internally contain what is illustrated in FIG. 20, and the connectors 224 and moveable plates 222 as well as the central post 220 and the stationary plate 218 would be operatively connected to button 230 through this chamber so that when the button 230 is pressed the chamber (again not shown) can be pulled back into the working end's outer tube 214a. This would also cause the circumferential size/shape of the working end to decrease.

In accordance with another embodiment, the plugger can be provided with a heat sensor 240 (FIG. 26), such as a thermocouple, which is illustratively shown to be on the stationary plate 218. The heat sensor 240 is operably connected to a display 242 in the handle 212 via a wire 244 which passes through the post 220 and shaft 214. The display 242 can be controlled by a microchip (not shown) which can be incorporated as part of the display and which will receive a temperature signal from the heat sensor 240. Based on the signal from the sensor, the temperature of the filler will be shown on the plugger display 242. Thus, with the plugger surface 226 in contact with the filler material, the temperature of the filling material (at least at the upper end of the filler material) will be shown on the display 242. Although the display 242 is shown to be on the handpiece 212 in FIG. 19, the temperature sensor could be place in communication with the control on the system base unit or the delivery device holder such that the temperature will be shown on the displays on the base unit and/or the holder. If the display is remote from the handpiece, the connection between the plugger and the display can be wireless or corded.

In one embodiment, display of temperature of the filler (either on the plugger hand piece 212, base unit or the holder) will provide the practitioner with needed information regarding the temperature of the filler material (e.g., plug) while it is being molded. Gutta-percha, when heated above a certain temperature (i.e., above about 42° C.-49° C.), typically changes between a beta phase and an alpha phase. As the gutta-percha in the alpha phase cools, the gutta-percha shrinks slightly. If molding pressure is removed from the gutta-percha plug too early (i.e., before shrinking ends), gaps may form between the molded gutta-percha plug and the wall of the root canal. However, by being able to monitor the temperature of the gutta-percha plug, the practitioner can maintain a molding/packing pressure on the gutta-percha plug until potential shrinkage of the gutta-percha has stopped. This will substantially reduce the likelihood that gaps will form between the molded gutta-percha plug and the root canal wall because of shrinkage, thus providing for a better seal of the root canal. If the temperature information is transmitted to a control system, the control system can control the heating of the filler material to precisely maintain the filler material at a desired temperature (e.g., below the temperature mediated phase transitions of the filler material). Additionally, the control system can use the temperature information to control an automatic obturation procedure also described above.

In accordance with another embodiment, the plugger can be provided with a pressure transducer which monitors the force applied to the filler material. This pressure transducer could be in communication with a controller to provide a warning (either auditory, visual, or tactile) if the desired pressure is exceeded). Such a pressure transducer can be located on one of the plates or at a junction between the plates and their respective posts/connectors or at the junction of the post/connectors with the shaft 214. The applied pressure could also be shown on the plugger display 242, on the base unit display or on a holder display.

FIG. 27 shows a plugger 117" having a "standard" plugger shaft 214". That is, the plugger shaft is not provided with a working end 216 as is the plugger 117. Rather the working end of the shaft 214" is of constant diameter. However, the plugger 117" is shown with a heat sensor 240 and display 242. The plugger 214" could also be provided with the noted pressure transducer. Thus, although the plugger 117" lacks the benefits of the variable shaped plugging surface 226 or 226', the plugger 117" will still display the temperature of the filler material, and thus facilitate the practitioner applying a molding pressure to the filler material until the temperature falls below a desired temperature. Also, this type of plugger could be utilized to regulate embodiments of the obturation method described herein. As previously described, precise temperature delivery can be controlled by having the temperature sensor in close proximity to the filler material at the time of heat delivery.

Modifications can be made to the plugger as shown and described. For example, rather than being connected to the shaft 214a, the moveable plates 222 could be connected to the stationary plate 218. For example, each moveable plate could move along a path in the stationary plate defined by a slot. This would, however, allow the moveable plates to move in one axis rather than in two axes. Further, although the moveably plates are shown to fully surround the stationary plate, the stationary plate could only be partially surrounded by the moveable plates. Additionally, depending on the shape of the moveable plates, the stationary plate could be omitted. In this instance, the inner area of the movable plates would combine to replace and fill in the area where the stationary plate was located.

In another embodiment of this universal plugger, the plugger could be provided with a vibrational generator which is adapted to induce vibrations (such as sonic or ultrasonic vibrations) in the plates. Inducing vibrations would potentially enhance molding of the filler material in the root canal. The generator can be a sonic or ultrasonic vibration generator. Other types of generators to generate vibrations forces can be used as well.

Figure 30:
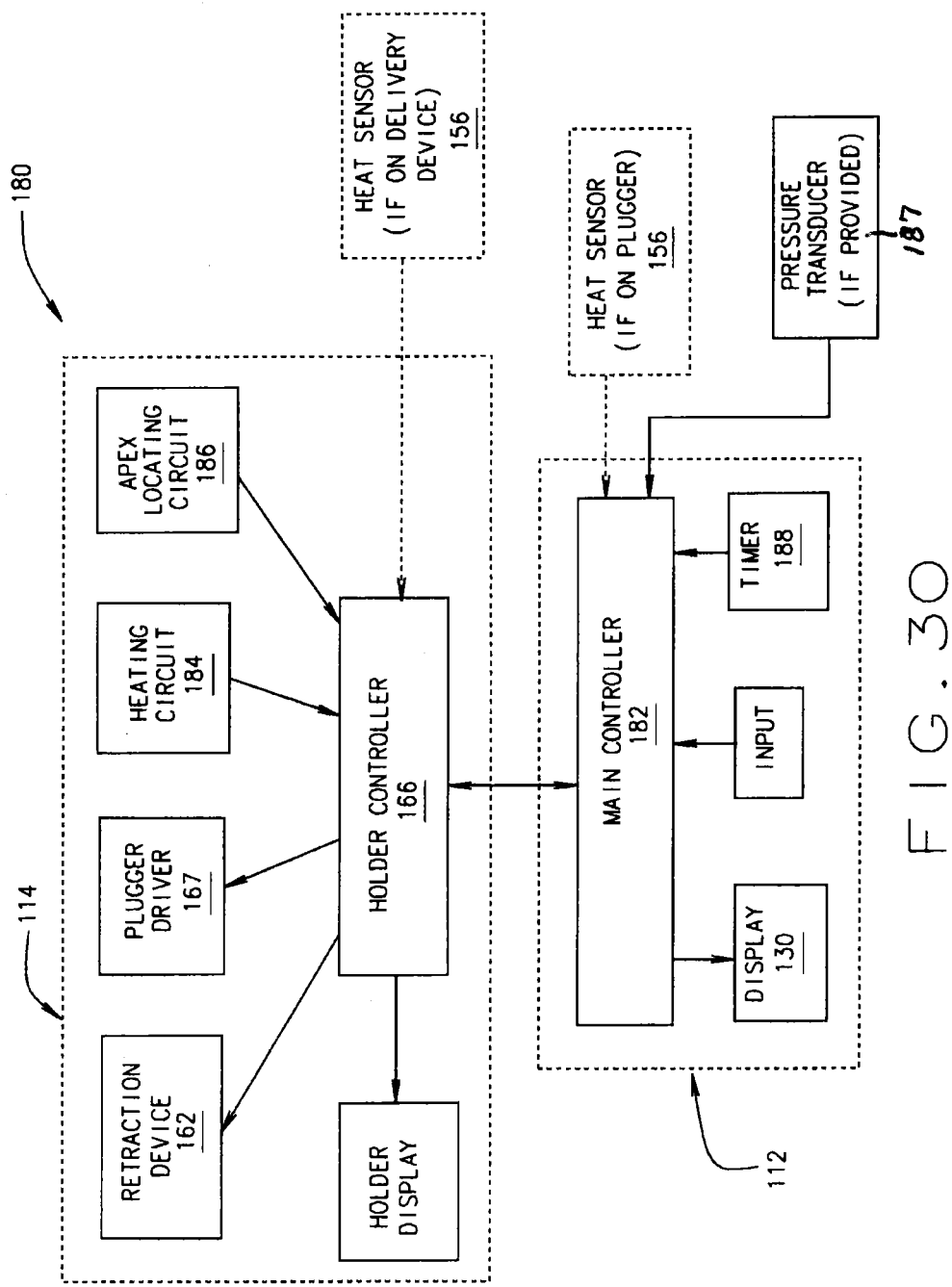
FIG. 30 is a schematic of a control system for the obturation system of FIG. 7A.

Turning to FIG. 30, the control system 180 of the system 110, 110' includes the main controller 182, an apex locating circuit 186, a heating circuit 184, the temperature sensor 156, and a timer 188. The main controller 182 is housed in the base unit 112, along with the base unit display 130 and the input buttons. The apex locating circuit 186, the heating circuit 184, the plugger driver 167, the retraction device 162, and the holder display are all on the holder and are in communication with the holder controller 166. In addition, a pressure transducer 187, if provided on the plugger, is in communication with the holder controller 166, such that the holder controller receives the pressure signal from the pressure transducer 187. Any of the retraction device 162, the plugger driver 167 and the holder display can be omitted from the holder, and hence from the system. Additionally, as noted above, the heat sensor can be located on or near the plugger working end, on the delivery device, or any other part of the system that will allow for an accurate determination of the temperature of the apical filler material or other desired site (e.g., tissue). The main controller 182 is in communication with the apex locating circuit 186, the heating circuit 184, the temperature sensor 156, and the pressure transducer 187 by way of the holder controller 166, and the timer 188. In the system 110 (FIG. 7A) where the plugger 117 is separate from the holder, the plugger is placed in communication with the base unit, and hence, the signal from the pressure transducer 187 would be received directly by the main controller 182, rather than by the holder controller 166.

In one embodiment, as with the system control system of FIG. 5, the main controller 182 receives signals indicative of the location of the delivery device (and hence the filler material) from the apex locating circuit 186, signals indicative of the temperature of the filler material from the temperature sensor 156, and signals indicative of the pressure exerted by the plugger from the pressure transducer 187. The controller 182 uses this information, as well as the information from the timer, to drive the display 130 (to display the filler temperature and the location of the filler plug/cone in the canal), and to control the heating circuit 184. In addition, if the holder 114 is provided with a delivery device retraction mechanism 162 and/or a plugger driver 167, the controller 182 uses the signals from the timer 186, the heat sensor 156, and the pressure transducer 187 to control the delivery device retraction mechanism and/or the plugger driver. The buttons 132 on the base unit 112 define an input device which is in communication with the main controller 182 to enable the practitioner to adjust the set temperature for the heating circuit and the heating cycle duration. Additionally, the base unit 112 can include a sound generator (not shown), as noted above, to provide sound signals to inform the practitioner of certain information, such as that the delivery device is in an acceptable location to begin heating, that the delivery device is extending through the apical foramen of the root canal, that the appropriate temperature has been reached and/maintained for the pre-set time, that the delivery device should be withdrawn from the tooth, and/or that the heating process should be inactivated.

In one embodiment, the apex locating circuit 186 includes the delivery device 116, 116' (which forms the probe of the circuit), the lip clip 148, and a resistance monitor 66 (as shown in FIG. 6A). The apex locating circuit produces an output which is received by the base unit controller 182 or the holder controller 166 (if the lip clip is connected directly to the holder). In the latter instance, the holder controller 166 transmits location information to the main controller 182.

In one embodiment, the heating circuit 184 includes the heating device which can be located either on the delivery device 116, 116' or on the holder 114, 114', 114".

As noted above, the optional temperature sensor(s) can be located either near the working end of the plugger, on the delivery device bed portion, or any other part of the system that will allow for an accurate determination of the temperature of the apical filler material, or other desired site. If the temperature sensor is located on the plugger, the temperature sensor information, in one embodiment, can be transmitted initially to the holder controller 166 (if the plugger is directly connected to the holder) or to the main controller 182 (if the plugger is directly connected to the base unit). If the control of the system 180 is centralized in the base unit, the controller 182 receives the temperature information (either directly from the temperature sensor or as transmitted by the holder controller 166) and controls the heating circuit 184 (and hence the heating device) in response to the temperature sensor output. The main controller 182 also drives the display 130 in response to the output from the temperature sensor to visibly show the temperature of the filler material in the canal.

Figure 34:
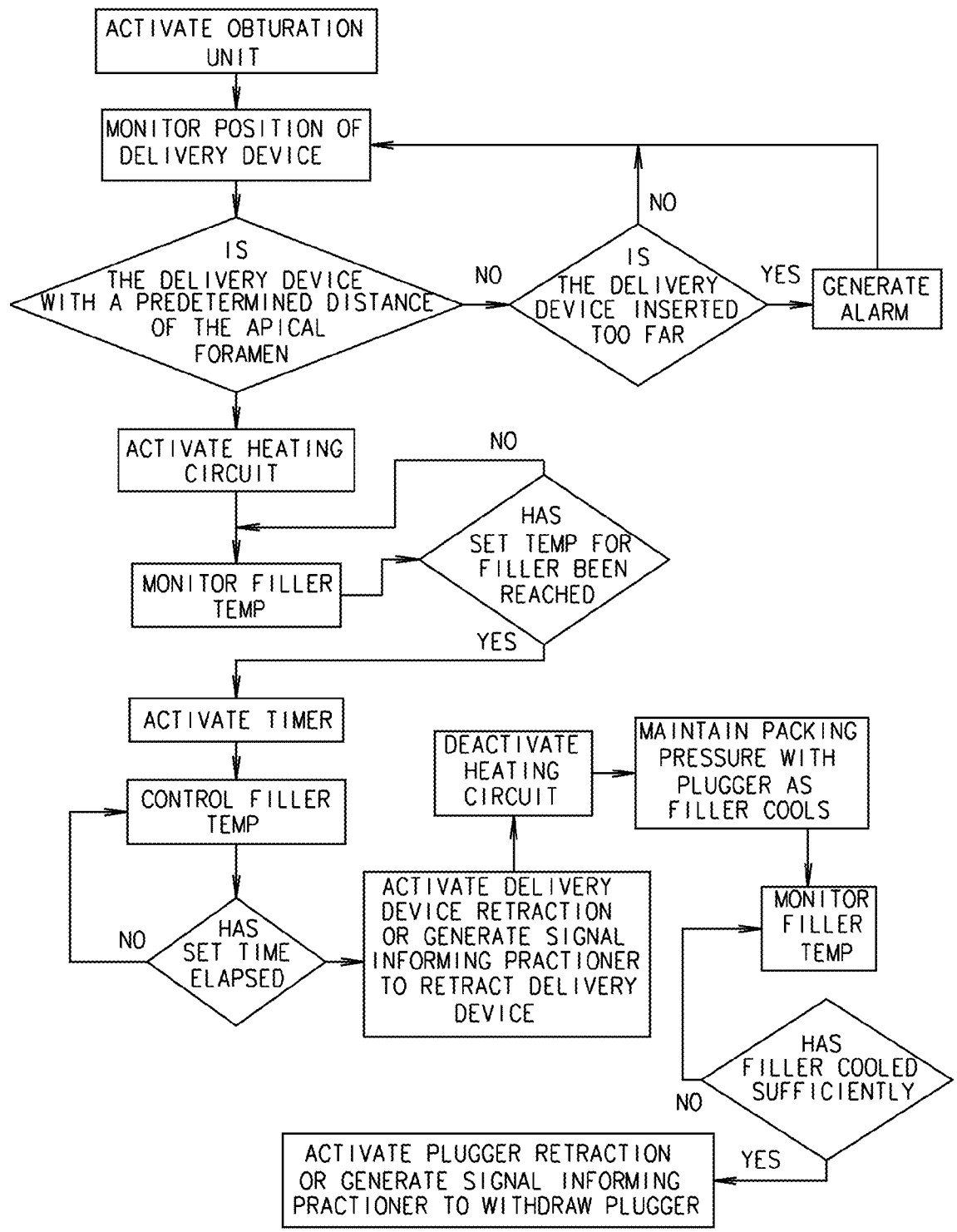
FIG. 34 is a flow chart of the process carried out by the control system of either FIG. 5 or FIG. 29.

In one embodiment, the heating circuit 184 is additionally controlled in response to the output from the apex locating circuit 186 and the timer 188. As noted above, the heating circuit 184 will not be activated unless the controller (holder controller 166 or main controller 182) determines that the end of the delivery device 116,116' (and hence the end of the filler material) is within a determined distance of the apical foramen of root canal. Further, the heating circuit will not be activated if the delivery device is extending through the apical foramen of the root canal. The timer 188 is activated once the control system determines that filler material 154 has been directly heated at its deepest level to the desired set temperature (between about, 37° C.-65° C., e.g., about 39° C.-47° C. or about 42° C.-45° C.). If the holder includes the plugger driver, the controller 182, in one embodiment, will send a signal to the holder controller 166 to activate the plugger driver to exert a molding pressure or load on the filler material. If the plugger 117 includes the temperature sensor, then, in one embodiment, the plugger surface will have been in contact with the filler material from the moment the obturation cycle is started. When the timer 188 has determined that the predetermined temperature has been achieved and held for the set time period (about 2-10 seconds), the controller 182 or controller 166 will deactivate the heating circuit 184. If the holder includes the retraction device 162, in one embodiment, the controller 182 will send a signal to the holder controller 166 to activate the retraction device to withdraw the delivery device 116, 116' from root canal just prior to the controller 182 sending the signal to deactivating the heating circuit 184. If the system is not provided with an automatic retraction device 162, the holder display and/or the main controller display 130 will prompted the practitioner to manually remove the delivery device just before the heating circuit is deactivated. Such a prompt can be a tactile, visual or audio prompt. Lastly, if the holder is provided with the plugger driver, in one embodiment, the system can maintain the molding force on the filler until the filler material drops to a predetermined value (such as about 37° C., i.e., normal body temperature). At that point, the plugger can be retracted by the plugger driver. The plugger driver will be controlled in response to the output from the pressure transducer, so that a predetermined force (i.e., not more than about 7 lbs) will not be exceeded as the plugger is urged against the filler material to mold the filler material. If the temperature sensor is on the plugger, then the plugger driver can be activated to retract the plugger in response to the temperature signal. However, it the temperature sensor is located on the delivery device, activation of the plugger driver to retract the plugger may be based on an average time for the filler material to cool from the set temperature to the desired "cool" temperature, such as around body temperature. The above method is shown in flow chart form in FIG. 34.

Figure 31B:
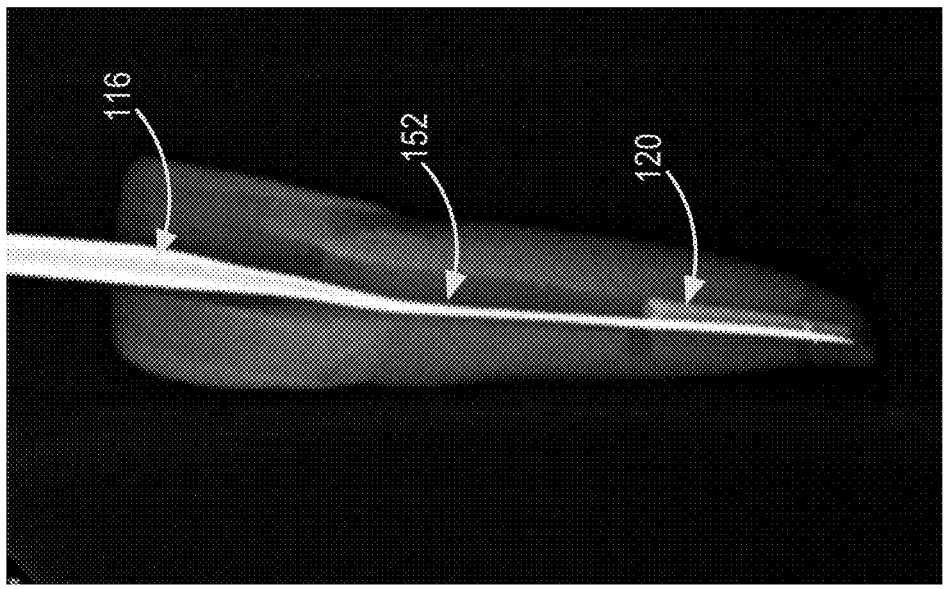
FIG. 31B is an x-ray similar to that of FIG. 31A, but without the plugger.
Figure 31A:
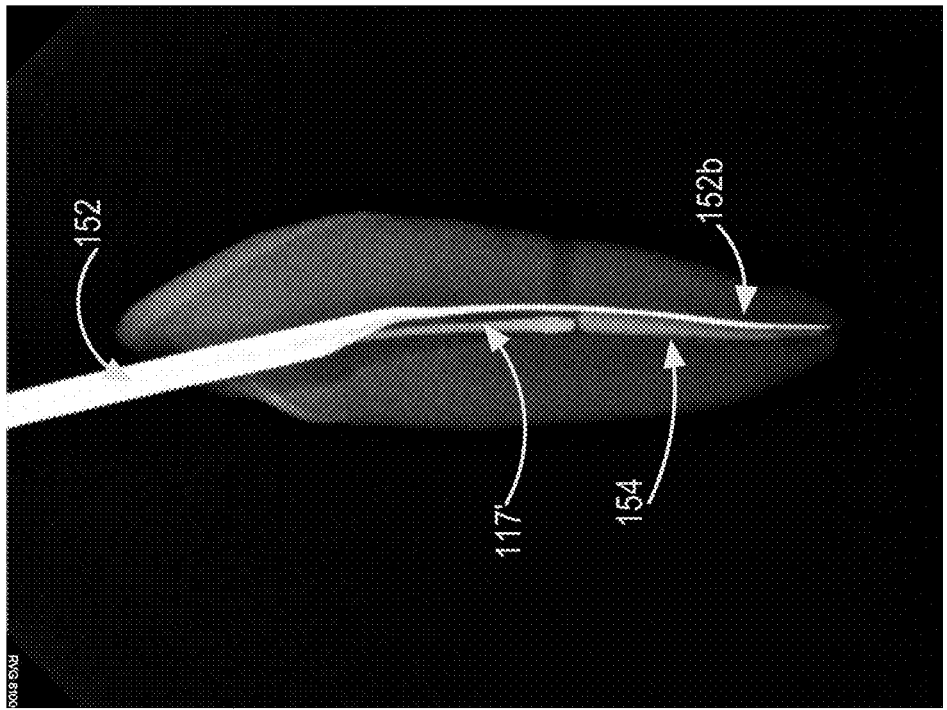
FIG. 31A is an x-ray showing the delivery device of FIG. 10 in a root canal with an associated plugger in engagement with a plug of filler material.
Figure 32:
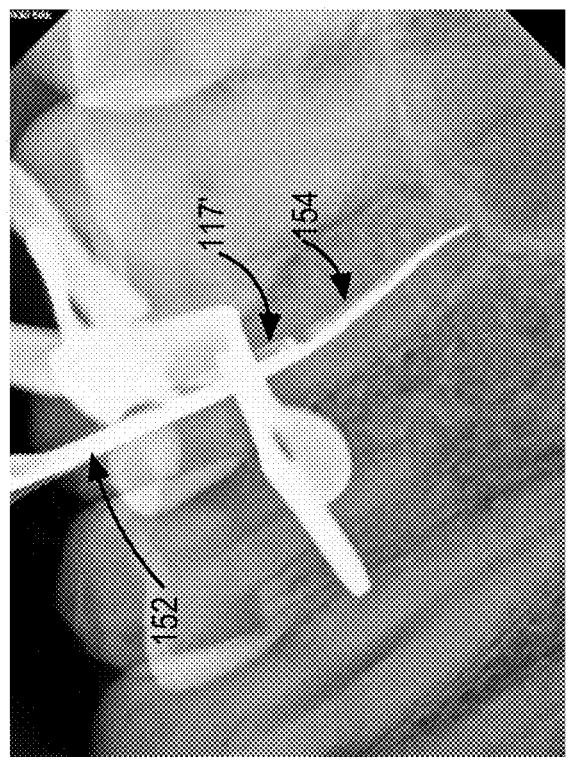
FIG. 32 is another x-ray showing the delivery device and plugger in a root canal during an obturation procedure FIGS. 33A-K contain a series of schematic drawings showing the progression of a filling/sealing procedure in a root canal using the delivery device of FIG. 10 connected to a further embodiment of the holder and the plugger of FIG. 19.
Figure 31C:
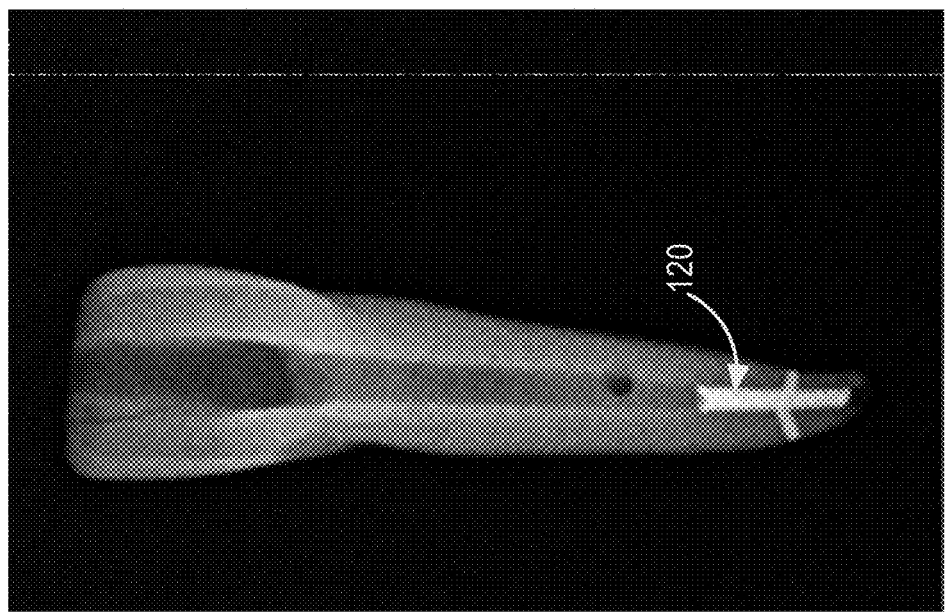
FIG. 31C is an x-ray of a tooth having the apex of the root canal filled using the obturation system.

The procedure is also shown with respect to a tooth in FIGS. 33A-K. In FIG. 33A, a prepared tooth is presented. In FIG. 33B-C, the delivery device with the filler material 120 is inserted into the canal. The X-ray of FIG. 31 shows the delivery device 116' positioned in the root canal. In FIG. 33D, of the nose 160' of the delivery device 114" is inserted into the connector portion 112' of the delivery device to connect the delivery device to the holder. Although the drawings of FIG. 33 show the holder 114", the holder 14, 114, or 114' could be used as well. In one embodiment, the delivery device could be mounted to the holder for the insertion of the delivery device into the root canal. With the delivery device connected to the holder, the delivery device will be connected into the apex locating circuit and will be in heat transfer communication with the heating device. In FIG. 33E, the plugger 117 is inserted into the root canal. Here, the plugger 117 is separate from the holder and delivery device. If the holder 114' (which has the internal plugger 117') is used, then the plugger will descend from the holder, as shown in FIGS. 29A-C. In FIG. 33F, the system has confirmed that the delivery device is in a proper location in the root canal, and has activated the heating circuit to heat the filler material. Because the delivery device shaft extends along the side of the filler material, the delivery device shaft will not interfere with the placement and use of the plugger while the delivery device is in place in the root canal. Hence, the obturation system allows for the practitioner to mold the filler material while the filler material is being heated and during the heating cycle. This is shown for example, in the x-ray images of FIGS. 31A and 32 and in FIG. 33G. In FIG. 31A, a temperature sensor, in the form of a thermocouple, can be seen at the end of the plugger.

FIG. 29A is one example of how an automated system may look as the top of the delivery device connects into a heating chamber, and the plugger (with the thermocouple at its working end) slides down the center. The system can be programmed to be automated in this embodiment: For example, clicking the delivery device into the holder channel completes the apex locating circuit to confirm location, the plugger allows for the feedback from the heating element to establish and control the temperature delivered to the filler material, and for feedback from the pressure transducer to control the plugger driver. The plugger can hold and mold the filler material, and the heating chamber can be programmed to remove the delivery device when all parameters have been established.

The molding pressure is continued through FIGS. 33H-J to mold the filler material to the root canal system. As can be seen, by comparing FIGS. 33H, I and J, the upper end of the filler material lowers from FIGS. 39H-J, and the lateral canals fill with filler material as the filler material is molded to 3-dimensionally seal the root canal. In FIG. 33J, the heating time has elapsed, and the delivery device is being withdrawn from the root canal. Once the delivery device is withdrawn from the canal, the source of heat (i.e., the delivery device) for the filler material will have been removed from the canal, and the heating circuit will be deactivated. As seen, in one embodiment, in FIG. 33K the plugger remains in the canal to continue to exert its molding pressure on the filler material to continue molding of the heated filler material, and to prevent the withdrawal of the delivery device from the canal from affecting the positioning of the filler material in the canal. Finally, in FIG. 33K, molding pressure is retained on the filler material as the filler material cools to reduce the possibility of voids or gaps forming between the filler material and the root canal wall as the filler material cools. A completed obturation is shown in the x-ray of FIG. 31C. As seen, the filler material 120 has been pressed or molded into the root canal so that the filler material fills and seals lateral canals which are visible.

In several embodiments, use of the delivery device 116, 116' will be substantially similar to the use of the delivery device 16, and need not be redescribed.

The obturation system, according to several embodiments, has one or more of the following advantages. First, the systems 10, 110, and 110' deliver heat directly to the filler material and along the entire length, or substantially along the length, of the filler material at a precise temperature, and are not limited to delivering heat only to the top of the filler material. As discussed above, applying heat from the top of the filler material does not allow for much heat to reach the apex of the filler material, as conventional filler materials (such as gutta-percha) are not good conductors of heat. Gutta-percha can only transmit heat well from about 1 mm, after which its heat conduction capacity drops sharply, and the gutta-percha cannot reliably transfer heat more than 2-4 mm. Thus, in some embodiments, the delivery device extends to the distal tip of the gutta-percha, or up to about 2 mm from the distal tip. In other embodiments, the delivery device extends more than 2 mm from distal tip (e.g., for use with filler materials that allow better conductivity). Another advantage of several embodiments of the system is the small temperature gradient from the top to bottom of the filler material. Yet another advantage of several embodiments of the system is the reduced temperature needed. Because heat is applied laterally (from the side) rather than only longitudinally (from the top) of the filler material, the temperatures that are delivered the filler material do not need to be as high as 200-300° C. Such temperatures are well in excess of the temperature mediated phase transitions of gutta-percha, and are even far in excess of the molding temperature of the gutta-percha that is needed to seal a root canal. Further, in several embodiments, the system 10, 110, 110' and especially the systems 110 and 110' of FIGS. 7A-12 and 29A-C, allows for packing and molding of the filler material during the heating cycle, rather than after the heating cycle.

Additionally, several embodiments of the system utilize apex locating technology at the time of obturation or sealing. Currently existing apex locating devices are used before final seating of the filler material in the canal, rather than at final seating of the filler material in the canal. Thus, although the practitioner can be fairly certain that the root canal has been prepared to the apical foramen of the root canal, without a device such as the obturation system 10, 110, or 110', the practitioner is less certain that the filler material is properly positioned in the canal at this stage of the obturation procedure.

Additionally, by controlling the temperature of the filler material and not heating gutta-percha filler material beyond the temperature mediated phase transitions according to some embodiments, shrinkage can be avoided or minimized, and the physical and mechanical properties of the filler material are able to be controlled and utilized.

As various changes could be made in the constructions herein without departing from the scope of the claimed invention, it is intended that all matter contained in the description or shown in the accompanying drawings shall be interpreted as illustrative and not in a limiting sense. For example, although the systems 10, 110, and 110' are shown to include controllers in their respective holders 14, 114, and 114' the holder controllers could be omitted, and the system could rely on a single controller in the base unit. In this instance, appropriate signals to and from the various components would travel through the cords connecting the holder, plugger and lip clip to the base unit. The holder 14 is described as being used with the delivery device 16; and the holder 114 is described as being used with the delivery device 116, 116'. However, any of the disclosed holders 14, 114, 114', 114" could be adapted to be receive any of the disclosed delivery devices 16,116, 116'.

In an alternate construction, the heating device can be contained within a chamber mounted on the plugger 117. In this variation, the delivery device 16, 116, 116' could connect or snap into to a retractable chamber on the plugger, and the plugger effectively becomes the holder. This retractable chamber could function as the heating chamber described herein. This connection of the delivery device to the retractable heating chamber would allow for the completion of the circuitry discussed herein. This includes the ability to confirm the correct position of the delivery device by analyzing the impedance and/or resistance in the apex locating circuit. If deemed in the correct position, this connection would then allow for direct heat transfer down the delivery device substantially along the entire length of the filler material. The working end of the plugger (which can contain a thermocouple) could be in contact with the filler material and feedback to the retractable heating chamber to confirm and regulate the establishment of the desired temperature for molding. Simultaneously as the heat is being delivered directly to the entire length of the filler material, three-dimensional compaction can occur. In addition, during this time of ideal molding conditions, the retractable chamber can be activated to remove the delivery device while the plugger secures and further molds the filler material. Once the plugger senses that the filler material has reached body temperature the plugger, containing the delivery device (minus the filler material) can be withdrawn and removed from the chamber mounted on the plugger for the next use.

The technology discussed herein was designed to enhance the sealing of root canal systems through a precise heat delivery and regulated three-dimensional molding/compaction. However, it is intended that these treatment modalities will carry over to other fields of use, particularly in medicine and the life sciences. Thus, although embodiments described herein are useful for obturation, they may also be used for other dental applications as well. In addition, non-dental medical applications are also well-suited for several embodiments. For example, the delivery device and plugger may be used to deliver, or facilitate insertion of, a variety of filler materials, including but not limited to, moldable biocompatible medical grade fillers into the body (such as bone cement for orthopedic applications, hydrogels, natural and synthetic grafts, etc.). The plugger, in some embodiments, is used to facilitate controlled insertion and stabilization of biomedical implants (such as stents, screws, and other temporary or permanent implants). In one embodiment, the distal end of the plunger is biocompatible and detachable and can, for example, serve as a barrier to extrusion for an implanted device. The use of pluggers described herein that are capable of adjusting to closely conform to changing diameters will be beneficial in several other applications. For example, this will allow for increased compaction forces when placing materials in arthroscopic surgery, such as the placement of stents through randomly changing ducts, arteries, veins, etc. In addition, precise heat and pressure measurements with related feedback systems will have benefit in this, as well as other treatment modalities. As a further example, measuring temperature and pressure within the tube/systems that drain blood in traumatic brain injuries, or other neurovascular or cardiovascular conditions, will aid in accuracy and precision.

The description herein illustrates various embodiments by way of example and not by way of claimed limitation. The non-limiting terms "embodiment" and "aspect" are used interchangeably. Additionally, it is to be understood that the claims are not limited in its application to the details of construction and the arrangements of components set forth in the following description or illustrated in the drawings. The claimed invention(s) is capable of other embodiments and of being practiced or being carried out in various ways. Also, it is to be understood that the phraseology and terminology used herein is for the purpose of description and should not be regarded as limiting.

What is claimed is:

1. An obturator for sealing an apical end of a prepared root canal, the obturator comprising a delivery device for delivering a plug of unheated filler material into a prepared root canal and a holder for the delivery device;

the holder comprising:

a body having a side surface, a forward end, a back end, and an internal channel extending inwardly from the forward end of said body; said channel being sized and shaped to removably receive at least an upper portion of a connecting end of shaft of said delivery device; and a heating circuit having a heating device; said heating device being contained in the holder proximate said channel; and a portion of an apex locating circuit;

the delivery device further comprising a bed at a distal end of said shaft; said shaft and said bed comprising heat conductive and electrically conductive material; said bed having an inner concave surface defining a filler material receiving surface and an outer convex surface opposite said inner surface; a plug of thermoplastic biocompatible filler material being mounted to said bed inner surface such that said bed outer surface opposite said filler material is substantially free of biocompatible filler material;

wherein said delivery device shaft is shaped to be received in said internal channel of said holder such that when said delivery device is mounted to said holder, at least a portion of said delivery device shaft is internal of said holder; and wherein, when said delivery device is received in said holder, said delivery device shaft is in heat transfer communication with said heating circuit such that upon activation of said heating circuit, heat will be transmitted along the delivery device shaft to heat the filler material mounted to the bed of the delivery device; and wherein when said delivery device is received in said holder, said delivery device shaft is in electrical communication with said portion of said apex locating circuit; such that said delivery device also forms a portion of said apex locating circuit.

2. The obturator of claim 1, wherein said holder comprises an electronically activatable retractor at least partially in said channel of said holder body; said retractor operatively and removably engaging the shaft of said delivery device; said retractor being operable to move said delivery device axially relative to said channel from an extended position to a retracted position.

3. The obturator of claim 1, wherein said holder comprises a plugger having a shaft with a plugger surface at an end of said shaft; said plugger surface being sized to be received within a prepared root canal; said plugger being axially movable relative to said channel between a retracted position and an extended position; said holder including a plugger driver operable to axially move said plugger between its said retracted and extended positions.

4. An obturator comprising; a delivery device comprising a shaft having a connecting portion and a bed portion at a distal end of said shaft and a plug of solid, unheated filler material mounted on the bed portion; and a holder for the delivery device comprising;

a holder body having a side surface, a forward end, a back end, and an internal channel extending inwardly from the forward end of said body; said channel being sized and shaped to removably receive at least an upper portion of the connecting portion of the shaft of said delivery device; whereby, when the delivery device is received in the internal channel, the delivery device bed and the filler material are external of, and spaced from, the forward end of the holder;

a heating circuit having a heating device proximate said internal channel; said heating device being positioned proximate said internal channel to be in thermal communication with said delivery device connecting portion when said delivery device connecting portion is received in said internal holder channel; and an electronically activated delivery device retractor internal of said holder body and at least partially in said channel of said internal holder body; said delivery device retractor operably and removably engaging said connecting portion of said delivery device when said delivery device connecting portion is received in said internal channel and being operable, when activated, to move said delivery device axially in said internal channel when the delivery device connecting portion is received in said internal channel from an extended position to a retracted position to withdraw said delivery device bed from the filler material during an obturation procedure.

5. The holder of claim 4, wherein said obturator comprises a plugger having a shaft with a plugger surface at an end of said shaft; said plugger surface being sized to be received in a prepared root canal; said plugger being axially movable relative to said internal channel from a retracted position in which plugger is contained within said holder and an extended position in which said plugger shaft extends forwardly of said forward end of said holder body and such that said plugger surface is external of and forward of said forward end of said holder body; said holder including a plugger driver operable to axially move said plugger between an extended position and a retracted position.

6. The obturator of claim 4 further including a controller; said controller being in communication with said heating circuit to control said heating circuit in response to a temperature signal; and said controller being in communication with said retractor to control the axial movement of said delivery device retractor.

7. The obturator of claim 6 wherein said holder further includes a timer; said controller being in communication with said timer; said controller controlling said retractor in response to a signal received from said timer.

8. The obturator of claim 6 wherein said holder further includes a timer; said controller being in communication with said timer; said controller controlling said heating circuit in response to a signal received from said timer.

9. The obturator of claim 6, further including a portion of an apex location circuit; said portion of said apex location circuit being in electrical contact with said delivery device when said delivery device is received in said holder, such that said delivery device forms a further portion of said apex location circuit; said controller being in communication with said at least a portion of the apex location circuit; said controller controlling said heating circuit in response to a signal from said apex location circuit.

10. The obturator of claim 1 further including a controller and a temperature sensor; said temperature sensor emitting a signal indicative of the temperature of said filling material; said controller being in communication with said heating circuit, said temperature sensor and said apex location circuit; said controller controlling said heater in response to signals from said apex location circuit and said temperature sensor.

11. The obturator of claim 10 wherein said controller activates said heating circuit only if it is determined via said apex location circuit that said delivery device is within a predetermined distance of an apex of a prepared root canal.

12. The obturator of claim 10 wherein said controller controls said heating circuit to heat the filler material to a substantially uniform temperature.

13. The obturator of claim 3 wherein said shaft of said delivery device is off-center relative to said plug of filler material, whereby, said plugger driver can insert said plugger into a prepared root canal while said delivery device is still in said root canal, such that said plugger can compress and/or mold said filler material while heat is being applied to said filler material.

14. An obturator for sealing an apical end of a prepared root canal, the obturator comprising a delivery device for delivering a plug of unheated filler material into a prepared root canal, a holder for the delivery device, and an apex locating circuit;

the delivery device comprising a shaft having a connecting end and a bed at a distal end of said shaft; said shaft and said bed comprising heat conductive and electrically conductive material; said bed having in inner concave surface and an outer convex surface; a plug of thermoplastic biocompatible filler material being mounted to said bed inner surface such that said bed outer surface opposite said filler material is substantially free of biocompatible filler material;

the apex locating circuit being defined in part by said delivery device; and the holder comprising:

a body having a side surface, a forward end, a back end, and an internal channel extending inwardly from the forward end of said body; said channel being sized and shaped to removably receive at least an upper portion of the connecting end of the shaft of said delivery device; and a heating circuit having a heating device; said heating device being contained in the holder proximate said channel such that said heating device is in thermal communication with said delivery device, whereby, when said heating circuit is activated, heat is delivered along the shaft of the delivery device to the bed of the delivery device to heat the filler material.

15. The obturator of claim 14 wherein said shaft of said delivery device is off-center relative to said plug of filler material.

16. The obturator of claim 12 wherein said controller controls the heating circuit to heat the filler material to a temperature that is not greater than about 26° C. above a molding temperature for the filler material.

17. An obturation system for facilitating filling of a root canal system, comprising:

a holder;

a delivery device removably receivable by the holder and comprising a shaft having a bed portion at a distal end thereof; said bed portion having an inner surface and an outer surface opposite said inner surface; said inner surface defining a filler material receiving surface; said bed portion being generally arcuate in shape and wherein said inner surface is concave and said outer surface is convex; said bed portion being at least partially electrically conductive along said bed outer surface; and said shaft being at least in part electrically conductive;

a plug of a biocompatible thermoplastic filler material comprising an upper surface, a side surface, and a distal end; wherein the delivery device bed portion has a greater thermal conductivity than the filler material, wherein the plug of filler material is mounted to the inner surface of the bed portion and the outer surface of the bed portion is substantially free of filler material such that said outer surface of said bed portion can contact a surface of the root canal at least at a distal end of said bed during use; the bed portion of the delivery device being shaped to wrap at least partially around the side surface of the plug of filler material and contacting the plug of filler material substantially along the length of the plug of filler material from the upper end of the plug of filler material to at or proximate the distal end of the filler material to facilitate direct heat transfer to the distal end of the plug of filler material, thereby facilitating heating of the filler material and delivery of the plug of filler material to the root canal system;

the holder comprising a heating circuit; the heating circuit comprising a heat sensor and a heating device configured to be in thermal communication with said bed portion when said delivery device is received by said holder; whereby, when said heating device is activated said bed portion is heated; the delivery device bed portion being configured to transfer heat to the filler material from the side surface of the filler material; said heat sensor generating a signal indicative of the temperature of the filler material;

an apex locating circuit, said delivery device being part of said apex locating circuit; said apex locating circuit generating a signal indicative of the location of the delivery device and the filler material plug on the delivery device within the root canal; and a controller, said controller being in communication with said heating device and said apex locating circuit; said controller controlling activating the heating device in response to the output of the apex locating circuit and controlling the heating device once activated in response to the output of said temperature sensor to uniformly heat the filler material to a temperature slightly above a molding temperature for the filler material.

18. The system of claim 17, wherein the filler material comprises gutta-percha.

19. The system of claim 17, further comprising a timer; said controller activating said timer when said heating device is activated or upon said filler material reaching a predetermined temperature; said controller deactivating said heating device after a predetermined period of time has elapsed.

20. The system of claim 19, wherein said predetermined period of time is about 2 to about 10 seconds.

21. The system of claim 17, wherein said controller prevents activation of said heating device unless said controller determines the apex of said filler material to be within a predetermined distance of an apex of a prepared root canal.

22. The system of claim 17, wherein said controller automatically activates the heating device to heat the filler material when it is determined that the apex of the filler material is at the apical end of a root canal or within a predetermined distance of the apical foramen of the root canal and wherein said controller prevents activation of the heating device if it is determined that the delivery device extends through an apical foramen of the root canal.

23. The system according to claim 17, wherein said controller controls the heating device to heat the filler material to a temperature of less than 75° C. at the upper surface of the filler material.

24. The system according to claim 17, further comprising a heating device configured to deliver heat to the filler material to heat the filler material to a temperature of between about 39° C. and about 65° C.

25. The system according to claim 17, wherein said heat sensor is located on said delivery device.

26. The system according to claim 17, further comprising a plugger having a plugger surface configured to contact the filler material.

27. The system of claim 26, wherein said plugger comprises one or more of a temperature sensor located on said plugger surface, a pressure transducer on said plugger surface, and a vibration generator positioned on said plugger to vibrate the plugger surface.

28. The system according to claim 17, wherein said apex locating circuit further comprises a lip clip; said delivery device comprising an electrically conductive portion extending along at least the outer surface of said delivery device bed portion and which will contact a surface of the root canal when the device is inserted in the root canal; said apex location confirming circuit generating a location signal indicative of the location of said delivery device in the root canal being treated.

29. The system according to claim 28 wherein said controller controls said heating device in response to the signal from said apex location circuit.

30. The system of claim 26, wherein the holder comprises said heating device.

31. The system of claim 17, wherein said holder comprises an axially movable retractor to which said delivery device is removably connectable; said retractor being operable to retract said delivery device from an extended portion to a retracted position; said retractor being adapted to move said delivery device axially within said root canal a distance sufficient to withdraw the delivery device from said filler material.

32. The system of claim 17, wherein said controller is in operative communication with said retractor; said controller emitting a command to automatically activate said retractor after said filler material has been heated to a predetermined temperature for a predetermined period of time.

33. The system of claim 26, further comprising a plugger driver,
wherein said controller is in operative communication with said plugger driver; said plugger driver being controlled by said controller to axially move said plugger, and
wherein said controller is configured to emit a command to activate said plugger driver to apply a molding pressure on said filler material while a heating device is activated.

34. The system of claim 33 wherein said plugger includes a pressure transducer; said transducer generating a signal indicative of the pressure or force applied by the plugger on the filler material; said controller being in operative communication with said pressure transducer to control said plugger driver in response to the signals from said pressure transducer.

35. The system of claim 17, wherein the filler material comprises a cone-shaped plug of gutta-percha and the delivery device is comprised of or is coated at least in part with platinum, silver, gold, copper, or aluminum or alloys thereof.

36. An obturation system for facilitating filling of a root canal system, comprising:
a delivery device comprising a shaft having a bed portion at a distal end thereof; said bed portion having an inner concave surface and an outer convex surface; said bed portion being at least partially electrically conductive along said bed outer surface; and said shaft being at least in part electrically conductive;
a plug of a biocompatible thermoplastic filler material comprising an upper surface, a side surface, and a distal end; wherein the delivery device bed portion has a greater thermal conductivity than the filler material; wherein the plug of filler material is mounted to the inner surface of the bed portion and the outer surface of the bed portion is substantially free of filler material; the bed portion of the delivery device wrapping at least partially around the side surface of the plug of filler material and contacting the plug of filler material substantially along the length of the plug of filler material from the upper end of the plug of filler material to at or proximate the distal end of the filler material to facilitate direct heat transfer to the distal end of the plug of filler material, thereby facilitating heating of the filler material and delivery of the plug of filler material to the root canal system;
a heating device in thermal communication with said bed portion; whereby, when said heating device is activated said bed portion is heated; the delivery device bed portion being configured to transfer heat to the filler material from the side surface of the filler material;
an apex location confirming circuit comprising said delivery device; said delivery device comprising an electrically conductive member extending along at least the outer surface of said delivery device bed portion and which will contact a surface of the root canal when the device is inserted in the root canal; said apex location confirming circuit generating a location signal indicative of the location of said delivery device in the root canal being treated; and
a controller, said controller being in communication with said heating device and said apex location confirming circuit to control said heating device; said controller controlling the heating device in response to signals received from said apex location circuit to heat the filler material to a temperature slightly above a molding temperature for the filler material; the bed portion contacting the filler material such that the plug of filler material is substantially uniformly heated to said temperature.

\* \* \* \* \*